US008853159B2

(12) United States Patent
Geigle et al.

(10) Patent No.: US 8,853,159 B2
(45) Date of Patent: *Oct. 7, 2014

(54) GLP-1 FUSION PEPTIDES

(75) Inventors: Peter Geigle, Alzenau (DE); Christine Wallrapp, Grossostheim (DE); Eric Thoenes, Budingen (DE)

(73) Assignee: Biocompatibles UK Ltd (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/482,354

(22) Filed: May 29, 2012

(65) Prior Publication Data

US 2012/0238497 A1 Sep. 20, 2012

Related U.S. Application Data

(63) Continuation of application No. 11/991,562, filed as application No. PCT/EP2006/009226 on Sep. 22, 2006, now Pat. No. 8,431,533.

(30) Foreign Application Priority Data

Sep. 22, 2005 (EP) ..................................... 05020718

(51) Int. Cl.
*A61K 38/26* (2006.01)
*C07K 14/605* (2006.01)
*A61K 39/00* (2006.01)

(52) U.S. Cl.
CPC .................... *C07K 14/605* (2013.01)
USPC .................... 514/11.7; 424/185.1; 424/192.1; 435/69.7; 530/308; 514/7.2

(58) Field of Classification Search
CPC ....................................................... A61K 38/00
See application file for complete search history.

(56) References Cited

U.S. PATENT DOCUMENTS

| | | | |
|---|---|---|---|
| 4,339,241 A | 7/1982 | Stocker | |
| 4,352,883 A * | 10/1982 | Lim .............................. | 435/178 |
| 4,687,529 A | 8/1987 | Wang | |
| 5,144,139 A | 9/1992 | Hillman et al. | |
| 5,861,284 A | 1/1999 | Nishimura et al. | |
| 6,165,739 A | 12/2000 | Clatch | |
| 6,267,954 B1 | 7/2001 | Abitbol et al. | |
| 6,849,708 B1 | 2/2005 | Habener | |
| 6,858,576 B1 | 2/2005 | Young et al. | |
| 6,922,578 B2 | 7/2005 | Eppstein et al. | |
| 2002/0130042 A1 | 9/2002 | Moerman et al. | |
| 2002/0168290 A1 | 11/2002 | Yuzhakov et al. | |
| 2003/0144206 A1 | 7/2003 | Knudsen et al. | |
| 2003/0195154 A1 | 10/2003 | Walker et al. | |
| 2003/0221201 A1 | 11/2003 | Prior et al. | |
| 2004/0143104 A1 | 7/2004 | Wadsworth et al. | |
| 2004/0146985 A1 | 7/2004 | Sun et al. | |
| 2004/0241451 A1 | 12/2004 | Clark et al. | |
| 2005/0016713 A1 | 1/2005 | Houck et al. | |
| 2005/0196820 A1 | 9/2005 | Zweig | |
| 2006/0030528 A1 | 2/2006 | Hathaway et al. | |
| 2006/0084604 A1 | 4/2006 | Kitaura et al. | |
| 2007/0050855 A1 | 3/2007 | Prior et al. | |
| 2010/0068289 A1 | 3/2010 | Geigle et al. | |
| 2010/0160556 A1 | 6/2010 | Wallrapp et al. | |
| 2010/0256332 A1 | 10/2010 | Wallrapp et al. | |
| 2011/0130329 A1 | 6/2011 | Geigle et al. | |

FOREIGN PATENT DOCUMENTS

| | | |
|---|---|---|
| DE | 224119 | 6/1985 |
| EP | 0018435 | 11/1980 |
| EP | 0215419 | 3/1987 |
| EP | 0503914 | 9/1992 |
| EP | 0757921 | 2/1997 |
| EP | 0891378 | 1/1999 |
| EP | 0941114 | 9/1999 |
| EP | 1454629 | 9/2004 |
| EP | 1529534 A2 | 5/2005 |
| EP | 1574858 | 9/2005 |
| EP | 1629534 | 3/2006 |
| EP | 1767545 | 3/2007 |
| EP | 1854455 | 11/2007 |
| EP | 2163243 | 3/2010 |
| WO | 94028141 | 12/1994 |
| WO | 9731943 | 9/1997 |
| WO | 9808871 | 3/1998 |
| WO | 9820895 | 5/1998 |
| WO | 9935255 A2 | 7/1999 |

(Continued)

OTHER PUBLICATIONS

Nikolaidis, 2004, Circulation, vol. 109, pp. 962-965.*
Kolchanov, 1988, Journal of Molecular Evolution, vol. 27, pp. 154-162.*
Pasquo, 2012, PLoS One, vol. 7, Issue 2, e32555.*
Drucker, et al, Glucagon gene expression in vertebrate brain, Journal of Biological Chemistry, 263(27): 13475-13478, 1988.
Anonymous: "Vascular Disease," XP002619794, Wikipedia 2011.
Bartsch, Evaluierange von aliginatverkapselten Endostatin Sezernierenden Stammzallen Zui, Behandlung des Glioolastoms, Dissertation, Hannover XP002549494.
During, et al., Glucagon-like Peptide-1 Receptor is Involved in Learning and Neuroprotection, Nature Medicine, 9 (9):1173-1179, 2003.

(Continued)

Primary Examiner — Elly-Gerald Stoica
(74) Attorney, Agent, or Firm — Quarles & Brady LLP

(57) ABSTRACT

The present invention provides fusion peptides having GLP-1 activity and enhanced stability in vivo, in particular resistancy to dipeptidyl peptidase IV. The fusion peptide comprises as component (I) N-terminally a GLP-1(7-35, 7-36 or 7-37) sequence and as component (II) C-terminally a peptide sequence of at least 9 amino acids or a functional fragment, variant or derivative thereof. Component (II) is preferably a full or partial version of IP2 (intervening peptide 2). A preferred embodiment comprises the sequence GLP-1(7-35, 36 or 37)/IP2/GLP-1(7-35, 36 or 37) or GLP-2. The fusion peptide may be produced in engineered cells or synthetically and may be used for preparing a medicament for treating various diseases or disorders, e.g. diabetes type 1 or 2, apoptosis related diseases or neurodegenerative disorders.

12 Claims, 23 Drawing Sheets
(14 of 23 Drawing Sheet(s) Filed in Color)

(56) References Cited

FOREIGN PATENT DOCUMENTS

| WO | 9946283 | 9/1999 |
|---|---|---|
| WO | 9953064 | 10/1999 |
| WO | 0166135 | 9/2001 |
| WO | 0246227 | 6/2002 |
| WO | 02067971 | 9/2002 |
| WO | 02076878 | 10/2002 |
| WO | 03002136 | 1/2003 |
| WO | 03010305 | 2/2003 |
| WO | 03011892 | 2/2003 |
| WO | 03020201 | 3/2003 |
| WO | 03058203 | 7/2003 |
| WO | 03083469 | 10/2003 |
| WO | 2003086444 | 10/2003 |
| WO | 2004022004 | 3/2004 |
| WO | 2005014048 | 2/2005 |
| WO | 2005014049 A2 | 2/2005 |
| WO | 2005035553 | 4/2005 |
| WO | 2005058958 | 6/2005 |
| WO | 2005077072 | 8/2005 |
| WO | 2005097175 A2 | 10/2005 |
| WO | 2006010143 | 1/2006 |
| WO | 2006015615 | 2/2006 |
| WO | 2006044063 | 4/2006 |
| WO | 2007018619 | 2/2007 |
| WO | 2007039140 | 4/2007 |
| WO | 2007128443 | 11/2007 |
| WO | 2005072216 | 8/2008 |

OTHER PUBLICATIONS

Erdogdu, et al, Exendin-4 stimulates proliferation of human coronary artery endothelial cells through eNOS-, PKA- and PI3K/Akt-dependent pathways and requires GLP-1 receptor, Molecular and Cellular Endocrinology, 325: 25-35, 2010.
Heile, et al., GLP-1 Secreting Encapsulated Human Mesnechymal Stem Cells for Neuropteoction, Cerebrospinal Fluid Research, 4: S47, 2007.
Heile, et al., Cerebral Transplantation of Encapsulated Mesenchymal Stem Cells Improves Cellular Pathology After Experimental Traumatic Brain Injury, Neuroscience Letters, 463: 176-181, 2009.
Kleinschmidt, Untersuchung von Endostatin Freisetzenden Stammzellimplantation zui Behandlung des GLioblastoms im Rattenmoddell, Dissertation, Hannover XP002549495.
Liu, et al., A Long-Acting GLP-1 Analogue Attenuates Induction of PAI-1 and Vascular Adhesion Molecules, Journal of endocrinology, 201: 59-66, 2009.
Malik, et al., Early evaluation of genetically engineered mesenchymal stromal stem cell therapy for prevention of left ventricular dysfunction in pigs, Heart, 95: A65-66, XP002619792.
Marneros, et al. Endogenous endostatin inhibits choroidal neovascularization, FASEB J. 21: 3809-3818, 2007.
Mcknight, Synthesis of Chitosan-Alginate Microcapsule Membranes, Journal of Bioactive and Compatible Polymers, 3: 334-355, 1988.
Nikolaidis, et al., Effects of Glucagon-Like Peptide-1 in Patients With Acute Myocardial Infarction and Left Ventricular Dysfunction After Successful Reperfusion, Circulation, 109: 962-965, 2004.
Takahashi, et al., Intraocular expression of endostatin reduces VEGF-induced retinal vascular permeability, neovascularization, and retinal detachment, The FASEB Journal, 17: 896-898, 2003.
Zhang, et al., Intraocular cell-based production of glucagon-like peptide-1 in the anterior chamber, Acta Ophthalmologica, 88: e348-349, 2010.
International Search Report issued on Apr. 11, 2008 in International Application No. PCT/EP2007/003775.
Ki M, S. et al. Long-term insulinotropic activity of glucagon-like peptide-1/polymer conjugate on islet microcapsules, • Tissue Engineering, 110(11-12): 1607-1616, 2004.
Kim, S., et al. Synthesis, bioactivity and specificity of glucagon-like peptide-1 (7-37) polymer conjugate to isolated rat islets, Biomatenals, Elsevier Science Publishers BV, 26(17): 3600, 2005.

Kim, S., et al (3), "Insulinotropic activity of sulfonylurea/pullulan conjugate in rate islet microcapsule",. Biomatenals, Elsevier Science Publishers BV, 24(26): 4843-4851, 2003.
Jork, A., et al., "Biocompatible alginate from freshly collected *Laminaria pallida* for implantation", Applied Microbiology and Biotechnology, vol. 53(2), pp. 224-229, 2000.
Winn, S. R., et al., "Managing chronic pain with encapsulated cell implants releasing catecholamines and endogenous opiods", Frontiers in Bioscience, vol. 10, pp. 367-368,2005.
Zimmerman, H., et al., "Towards a medically approved technology for alginate-based microcapsules allowing long-term immunoisolated transplantation", Journal of Materials Science: Materials in Medicine, vol. 16(6), pp. 492-501, 2005.
Chae, S. Y., et al., "Bioactive polymers for biohybrid artificial pancreas", Journal of Drug Targeting,vol. 9(6), pp. 473-484, 2001.
Brinker, T., Tennis: Tissue Engineering von Neuro—Implantation zur Schmerztherapie; Teilprojekt 1: In vivo Madelle fur gekapselte Zellen and in-vivo Validierung [Online], pp. 1-137, 2006.
Malpique, et at., "118. Cryopreservation of neuroblastoma N2a cells in an alginate environment: strategies to improve cell recovery and neuronal differentiation after thawing", Cryobiology, vol. 55(3),pp. 363-364, 2007.
International Search Report and Written Opinion issued on Nov. 17, 2008 in International Application No. PCT/EP2008/002414.
Busby et al., "Proglucagon (Fragment)", Uniprot, Q6RYB1, May 7, 2004.
Chen et al., "Glucagon precursor contains: Glicentin-related polypeptide (GRPP); Glucagon; Glucagon-like peptide 1 (GLP-1 ); Glucagon-like peptide 1 (7-37) (GLP-1 (7-37)); Glucagon-like peptide (7-36) (GLP-1 (7-36)); Glucaqon-like peptide 2(GLP-2)|", Uniprot, 012956, Jul. 1, 2007.
International Preliminary Report on Patentability issued on Oct. 8, 2009 in International Application No. PCT/EP2008/002414.
International Preliminary Report on Patentability issued on Jul. 24, 2008 in International Application No. PCT/EP2008/002278.
Dosch, M., et al., Fresenius Journal of Analytical Chemistry, vol. 361(2), pp. 174-178, 1998.
Heiss, C., et al., Analytica Chimica Acta, vol. 396(2/3), pp. 309-316, 1999.
Bass, D., Non-Final Office Action dated Dec. 2, 2009 issued in U.S. Appl. No. 11/073,254.
Bass, D., Notice of Allowance dated Aug. 27, 2010 issued in U.S. Appl. No. 11/073,254.
Kieffer, T.J. et al.: "The Blucagon-Like Peptides", Endocrine Reviews, Baltimore, Md., vol. 20(6), pp. 876-913, 1999.
Drucker, D.J.: "Glucagon-Like Peptides: Regulators of Cell Proliferation, Differentiation, and Apoptosis", Molecular Endocrinology, vol. 17(2), pp. 161-171,2003.
Perry, T.A. et al.: "Enhancing Central Nervous System Endogenous GLP-1 Receptor Pathways for Intervention in Alzheimer's Disease", Current Alzheimer Research, vol. 2(3), pp. 377-385, 2005.
English translation of Abstract of DD 224119 No Date Available.
Extended European Search Report dated Oct. 19, 2010.
Extended European Search Report dated Oct. 27, 2010.
Gundewar, et al., A Degradation Product of GLP-1 Confers Protection Against Acute Myccardial Ischemia Reperfusion Injury in Diabetes Mellitus, Journal of the American College of Cardiology, vol. 51(1)), p. A378 (XP002519012).
Heile, et al., Clinical Translation of Stem Cell Therapy in Traumatic Brain Injury: The Potential of Encapsulated Mesenchymal Cell Biodelivery of Glucagon-Like Peptide-1, Dialogues in Clinical Neuroscience, 2011, 13(3):279-286.
Kolchanov, et al., Single Amino Acid Substitutions Producing Instability of Globular Proteins. Calculation of Their Frequencies in the Entire Mutational Spectra of the a- and B-Subunits of Human Hemoglobin, Journal of Molecular Evolution, 1988, 27:154-162.
Pasquo, et al., Structural Stability of Human Protein Tyrosine Phosphatase p Catalytic Domain: Effect of Point Mutations, PLoS One, 2012, 7(2):e32555, pp. 1-11.
Zhang, et al., Microencapsulating and Banking Living Cells for Cell-Based Medicine, J. Healthc Eng., 2011, 2 (4):427-446.

* cited by examiner

C

A

B

SEQUENCE LISTING

```
<160> NUMBER OF SEQ ID NOS: 45

<210> SEQ ID NO 1
<211> LENGTH: 31
<212> TYPE: PRT
<213> ORGANISM: Artificial
<220> FEATURE:
<223> OTHER INFORMATION: Description of sequence:  synthetic peptide
      corresponding to GLP-1(7-37) (see description p. 36)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 15
<212> TYPE: PRT
<213> ORGANISM: Artificial
<220> FEATURE:
<223> OTHER INFORMATION: Description of sequence: full-length IP-2
      sequence having all 15 amino acids of the naturally occurring IP-2
      sequence, human; (see description p. 36)

<400> SEQUENCE: 2

Arg Arg Asp Phe Pro Glu Glu Val Ala Ile Val Glu Glu Leu Gly
1               5                   10                  15

<210> SEQ ID NO 3
<211> LENGTH: 15
<212> TYPE: PRT
<213> ORGANISM: Artificial
<220> FEATURE:
<223> OTHER INFORMATION: Description of sequence: full-length IP-2
      sequence having all 15 amino acids of the naturally occurring IP-2
      sequence, murine; (see description p. 36)

<400> SEQUENCE: 3

Arg Arg Asp Phe Pro Glu Glu Val Ala Ile Ala Glu Glu Leu Gly
1               5                   10                  15

<210> SEQ ID NO 4
```

```
<211> LENGTH: 35
<212> TYPE: PRT
<213> ORGANISM: Artificial
<220> FEATURE:
<223> OTHER INFORMATION: Description of sequence: murine isoform of GLP-
      2 (see description p. 36)

<400> SEQUENCE: 4

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Arg Lys
        35

<210> SEQ ID NO 5
<211> LENGTH: 35
<212> TYPE: PRT
<213> ORGANISM: Artificial
<220> FEATURE:
<223> OTHER INFORMATION: Description of sequence: human isoform of GLP-2
      (see description p. 36)

<400> SEQUENCE: 5

His Ala Asp Gly Ser Phe Ser Asp Glu Met Ser Thr Ile Leu Asp Asn
1               5                   10                  15

Leu Ala Thr Arg Asp Phe Ile Asn Trp Leu Ile Gln Thr Lys Ile Thr
            20                  25                  30

Asp Lys Lys
        35

<210> SEQ ID NO 6
<211> LENGTH: 79
<212> TYPE: PRT
<213> ORGANISM: Artificial
<220> FEATURE:
<223> OTHER INFORMATION: Description of sequence: SEQ ID No: 6 (ID6syn,
      CM1) corresponds to GLP-1(7-37)-IP2-RR-GLP1(7-37), 79 aa, 8,7 kD
      (see description p. 36)

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Arg Asp Phe Pro Glu Glu Val Ala Ile Ala Glu Glu Leu Gly Arg Arg
        35                  40                  45

His Ala Glu Gly Thr Phe Thr Ser Asp Val Ser Ser Tyr Leu Glu Gly
    50                  55                  60

Gln Ala Ala Lys Glu Phe Ile Ala Trp Leu Val Lys Gly Arg Gly
65                  70                  75

<210> SEQ ID NO 7
<211> LENGTH: 83
<212> TYPE: PRT
<213> ORGANISM: Artificial
<220> FEATURE:
<223> OTHER INFORMATION: Description of sequence: SEQ ID No: 7 (ID7rec,
      CM2) corresponds to GLP-1(7-37)-IP2-RR-GLP2, 83 aa, 9,4 kD
      (see description p. 36)

<400> SEQUENCE: 7

His Ala Glu Gly Thr Phe Thr Ser Asp Val Ser Ser Tyr Leu Glu Gly
1               5                   10                  15
```

```
Gln Ala Ala Lys Glu Phe Ile Ala Trp Leu Val Lys Gly Arg Gly Arg
            20                  25                  30

Arg Asp Phe Pro Glu Glu Val Ala Ile Ala Glu Glu Leu Gly Arg Arg
        35                  40                  45

His Ala Asp Gly Ser Phe Ser Asp Glu Met Ser Thr Ile Leu Asp Asn
 50                  55                  60

Leu Ala Thr Arg Asp Phe Ile Asn Trp Leu Ile Gln Thr Lys Ile Thr
 65                  70                  75                  80

Asp Lys Lys

<210> SEQ ID NO 8
<211> LENGTH: 46
<212> TYPE: PRT
<213> ORGANISM: Artificial
<220> FEATURE:
<223> OTHER INFORMATION: Description of sequence: SEQ ID No:8 (ID8 syn,
      CM3) corresponds to GLP-1(7-37)-IP2, 46 aa, 5,1 kD;

<400> SEQUENCE: 8

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly Arg
            20                  25                  30

Arg Asp Phe Pro Glu Glu Val Ala Ile Ala Glu Glu Leu Gly
        35                  40                  45

<210> SEQ ID NO 9
<211> LENGTH: 97
<212> TYPE: PRT
<213> ORGANISM: Artificial
<220> FEATURE:
<223> OTHER INFORMATION: Description of sequence: artificial

<400> SEQUENCE: 9

Met Ala Pro Ala Ala Trp Leu Arg Ser Ala Ala Ala Arg Ala Leu Leu
 1               5                  10                  15

Pro Pro Met Leu Leu Leu Leu Leu Gln Pro Pro Pro Leu Leu Ala Arg
            20                  25                  30

Ala Leu Pro Pro Asp Val His His Leu His Ala Glu Arg Arg Gly Pro
        35                  40                  45

Gln Pro Trp His Ala Ala Leu Pro Ser Ser Pro Ala Pro Ala Pro Ala
 50                  55                  60

Thr Gln Glu Ala Pro Arg Pro Ala Ser Ser Leu Arg Pro Pro Arg Cys
 65                  70                  75                  80

Gly Val Pro Asp Pro Ser Asp Gly Leu Ser Ala Arg Asn Arg Gln Lys
            85                  90                  95

Arg

<210> SEQ ID NO 10
<211> LENGTH: 79
<212> TYPE: PRT
<213> ORGANISM: Artificial
<220> FEATURE:
<223> OTHER INFORMATION: Description of sequence: SEQ ID No: 10
      (N-GLP-1(7-37)-IP2(human)-RR-GLP-1(7-37)-C, also designated human
      CM1), (see description p. 36)

<400> SEQUENCE: 10

His Ala Glu Gly Thr Phe Thr Ser Asp Val Ser Ser Tyr Leu Glu Gly
 1               5                  10                  15
```

```
Gln Ala Ala Lys Glu Phe Ile Ala Trp Leu Val Lys Gly Arg Gly Arg
            20                  25                  30

Arg Asp Phe Pro Glu Glu Val Ala Ile Val Glu Glu Leu Gly Arg Arg
        35                  40                  45

His Ala Glu Gly Thr Phe Thr Ser Asp Val Ser Tyr Leu Glu Gly
 50                  55                  60

Gln Ala Ala Lys Glu Phe Ile Ala Trp Leu Val Lys Gly Arg Gly
65                  70                  75

<210> SEQ ID NO 11
<211> LENGTH: 83
<212> TYPE: PRT
<213> ORGANISM: Artificial
<220> FEATURE:
<223> OTHER INFORMATION: Description of sequence: SEQ ID No: 11
      (N-GLP-1(7-37)-IP2(human)-RR-GLP-2-C), also designated human CM2
      herein), (see description p. 36)

<400> SEQUENCE: 11

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly Arg
            20                  25                  30

Arg Asp Phe Pro Glu Glu Val Ala Ile Val Glu Glu Leu Gly Arg Arg
        35                  40                  45

His Ala Asp Gly Ser Phe Ser Asp Glu Met Asn Thr Ile Leu Asp Asn
 50                  55                  60

Leu Ala Ala Arg Asp Phe Ile Asn Trp Leu Ile Gln Thr Lys Ile Thr
65                  70                  75                  80

Asp Arg Lys

<210> SEQ ID NO 12
<211> LENGTH: 46
<212> TYPE: PRT
<213> ORGANISM: Artificial
<220> FEATURE:
<223> OTHER INFORMATION: Description of sequence: SEQ ID No: 12, GLP-
      1(7-37) linked without any linker sequence via its C-terminus to
      human IP2 (see description p. 36)

<400> SEQUENCE: 12

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly Arg
            20                  25                  30

Arg Asp Phe Pro Glu Glu Val Ala Ile Val Glu Glu Leu Gly
        35                  40                  45

<210> SEQ ID NO 13
<211> LENGTH: 815
<212> TYPE: DNA
<213> ORGANISM: Artificial
<220> FEATURE:
<223> OTHER INFORMATION: Description of sequence: (SEQ ID No:13)
      represents the translated peptide sequence of the construct
      according to Fig. 1k (SEQ ID No: 14), (see description p. 37);
<220> FEATURE:
<221> NAME/KEY: CDS
<222> LOCATION: (11)..(118)
<220> FEATURE:
<221> NAME/KEY: CDS
<222> LOCATION: (387)..(809)
```

-continued

<400> SEQUENCE: 13

```
gatatccacc atg gcc ccc gcc gcc tgg ctg agg agc gcc gcc gcc agg       49
           Met Ala Pro Ala Ala Trp Leu Arg Ser Ala Ala Ala Arg
           1               5                   10 gcc ctg ctg cca ccc atg ctg ctg ctg ctg cag ccc cca cct ctg           97
Ala Leu Leu Pro Pro Met Leu Leu Leu Leu Leu Gln Pro Pro Pro Leu
 15                  20                  25 ctg gcc cgg gcc ctg ccc ccg gtgagtgccc gccactcgcc gtccgctcct         148
Leu Ala Arg Ala Leu Pro Pro
 30                  35 cgctgagggg cgccgggca cgcgggctgg gccagcggc gtatccggac gccaagaaac      208
cagagagcca gccagatgcc aaagggccct gccatgtgcc ggtgcccttt ccctctccat    268
ttgccctgcc acacagtggg ctggggttgc acgtgtgttt gctgacaggc cacatctcta    328
actgtgggcc atgtggacct aggcctgac cagacccctca tgtcttcctc cttcccag     386 gac gtg cac cac ctg cac gcc gag agg cgc ggc cct cag ccc tgg cac     434
Asp Val His His Leu His Ala Glu Arg Arg Gly Pro Gln Pro Trp His
                 40                  45                  50 gcc gcc ctg cca agc agc cct gcc cct gcc cca gcc acc cag gag gcc     482
Ala Ala Leu Pro Ser Ser Pro Ala Pro Ala Pro Ala Thr Gln Glu Ala
             55                  60                  65 ccc agg cct gcc agc agc ctg agg cca ccc agg tgc ggc gtg cct gat     530
Pro Arg Pro Ala Ser Ser Leu Arg Pro Pro Arg Cys Gly Val Pro Asp
 70                  75                  80 ccc tcc gat ggc ctg agc gct cgg aat cgg cag aag agg cac gcc gag     578
Pro Ser Asp Gly Leu Ser Ala Arg Asn Arg Gln Lys Arg His Ala Glu
 85                  90                  95                 100 ggc acc ttc acc tcc gac gtg agc agc tac ctg gag ggc cag gcc gcc     626
Gly Thr Phe Thr Ser Asp Val Ser Ser Tyr Leu Glu Gly Gln Ala Ala
                105                  110                 115 aag gag ttc atc gcc tgg ctg gtg aag ggc agg ggc cgc agg gac ttc     674
Lys Glu Phe Ile Ala Trp Leu Val Lys Gly Arg Gly Arg Arg Asp Phe
             120                 125                 130 cct gag gag gtg gcc atc gtg gag gag ctg ggc cgg cga cac gcc gag     722
Pro Glu Glu Val Ala Ile Val Glu Glu Leu Gly Arg Arg His Ala Glu
 135                 140                 145 ggc acc ttc acc tcc gac gtg agc agc tac ctg gag ggc cag gcc gcc     770
Gly Thr Phe Thr Ser Asp Val Ser Ser Tyr Leu Glu Gly Gln Ala Ala
         150                 155                 160 aag gag ttc atc gcc tgg ctg gtg aag ggc agg ggc tga gcgcgc          815
Lys Glu Phe Ile Ala Trp Leu Val Lys Gly Arg Gly
 165                 170                 175
```

<210> SEQ ID NO 14
<211> LENGTH: 815
<212> TYPE: DNA
<213> ORGANISM: Artificial
<220> FEATURE:
<223> OTHER INFORMATION: Description of sequence: DNA sequence of the construct according to Fig. 1k, (see description p. 37);

<400> SEQUENCE: 14

```
gatatccacc atggccccccg ccgcctggct gaggagcgcc gccgccaggg ccctgctgcc      60
acccatgctg ctgctgctgc tgcagccccc acctctgctg gccgggccc tgccccggt       120 gagtgcccgc cactcgccgt ccgctcctcg ctgaggggc gccgggcacg cgggctgggc      180
ccagcggcgt atccggacgc caagaaacca gagagccagc cagatgccaa agggccctgc     240
catgtgccgg tgccctttcc ctctccattt gccctgccac acagtgggct ggggttgcac     300
```

-continued

```
gtgtgtttgc tgacaggcca catctctaac tgtgggccat gtggacctta ggcctgacca     360
gaccctcatg tcttcctcct tcccaggacg tgcaccacct gcacgccgag aggcgcggcc     420
ctcagccctg cacgccgcc ctgccaagca gccctgcccc tgccccagcc acccaggagg     480 ccccaggcc tgccagcagc tgaggccac ccaggtgcgg cgtgcctgat ccctccgatg     540
gcctgagcgc tcggaatcgg cagaagaggc acgccgaggg caccttcacc tccgacgtga     600
gcagctacct ggagggccag gccgccaagg agttcatcgc ctggctggtg aagggcaggg     660
gccgcaggga cttccctgag gaggtggcca tcgtggagga gctgggccgg cgacacgccg     720
agggcacctt cacctccgac gtgagcagct acctggaggg ccaggccgcc aaggagttca     780
tcgcctggct ggtgaagggc agggctgag cgcgc                                 815
```

<210> SEQ ID NO 15
<211> LENGTH: 834
<212> TYPE: DNA
<213> ORGANISM: Artificial
<220> FEATURE:
<223> OTHER INFORMATION: Description of sequence: DNA sequence and
      sequence of the translated peptide according to the construct Fig.
      1h, (see description p. 38);
<220> FEATURE:
<221> NAME/KEY: CDS
<222> LOCATION: (11)..(118)
<220> FEATURE:
<221> NAME/KEY: CDS
<222> LOCATION: (387)..(821)

<400> SEQUENCE: 15

```
gatatccacc atg gcc ccc gcc gcc tgg ctg agg agc gcc gcc gcc agg          49
            Met Ala Pro Ala Ala Trp Leu Arg Ser Ala Ala Ala Arg
              1               5                  10 gcc ctg ctg cca ccc atg ctg ctg ctg ctg ctg cag ccc cca cct ctg        97
Ala Leu Leu Pro Pro Met Leu Leu Leu Leu Leu Gln Pro Pro Pro Leu
       15                  20                  25 ctg gcc cgg gcc ctg ccc ccg gtgagtgccc gccactcgcc gtccgctcct          148
Leu Ala Arg Ala Leu Pro Pro
 30                  35 cgctgagggg cgccgggca cgcgggctgg gccagcggc gtatccggac gccaagaaac        208
cagagagcca gccagatgcc aaagggccct gccatgtgcc ggtgcccttt ccctctccat     268
ttgccctgcc acacagtggg ctggggttgc acgtgtgttt gctgacaggc cacatctcta     328
actgtgggcc atgtggacct taggcctgac cagaccctca tgtcttcctc cttcccag      386 gac gtg cac cac ctg cac gcc gag agg cgc ggc cct cag ccc tgg cac        434
Asp Val His His Leu His Ala Glu Arg Arg Gly Pro Gln Pro Trp His
           40                  45                  50 gcc gcc ctg cca agc agc cct gcc cct gcc cca gcc acc cag gag gcc        482
Ala Ala Leu Pro Ser Ser Pro Ala Pro Ala Pro Ala Thr Gln Glu Ala
       55                  60                  65 ccc agg cct gcc agc agc ctg agg cca ccc agg tgc ggc gtg cct gat        530
Pro Arg Pro Ala Ser Ser Leu Arg Pro Pro Arg Cys Gly Val Pro Asp
   70                  75                  80 ccc tcc gat ggc ctg agc gct cgg aat cgg cag aag agg cac gcc gag        578
Pro Ser Asp Gly Leu Ser Ala Arg Asn Arg Gln Lys Arg His Ala Glu
85                  90                  95                 100 ggc acc ttc acc tcc gac gtg agc agc tac ctg gag ggc cag gcc gcc        626
Gly Thr Phe Thr Ser Asp Val Ser Ser Tyr Leu Glu Gly Gln Ala Ala
               105                 110                 115 aag gag ttc atc gcc tgg ctg gtg aag ggc agg ggc cgc agg gac ttc        674
Lys Glu Phe Ile Ala Trp Leu Val Lys Gly Arg Gly Arg Arg Asp Phe
           120                 125                 130
```

```
cct gag gag gtg gcc atc gtg gag gag ctg ggc cgg cga cac gcc gac    722
Pro Glu Glu Val Ala Ile Val Glu Glu Leu Gly Arg Arg His Ala Asp
        135                 140                 145 ggc agc ttc agc gac gag atg aac acc atc ctg gac aac ctg gcc gcg    770
Gly Ser Phe Ser Asp Glu Met Asn Thr Ile Leu Asp Asn Leu Ala Ala
    150                 155                 160 cgc gac ttc atc aac tgg ctg atc cag acc aag atc acc gat cgg aag    818
Arg Asp Phe Ile Asn Trp Leu Ile Gln Thr Lys Ile Thr Asp Arg Lys
165                 170                 175                 180 tga gcgcgctgat atc                                                 834

<210> SEQ ID NO 16
<211> LENGTH: 834
<212> TYPE: DNA
<213> ORGANISM: Artificial
<220> FEATURE:
<223> OTHER INFORMATION: Description of sequence: DNA sequence of the
      construct according to Fig. 1h, (see description p. 38);

<400> SEQUENCE: 16
gatatccacc atggccccccg ccgcctggct gaggagcgcc gccgccaggg ccctgctgcc     60
acccatgctg ctgctgctgc tgcagccccc acctctgctg gccgggccc tgccccggt     120 gagtgcccgc cactcgccgt ccgctcctcg ctgagggggc gccgggcacg cgggctgggc    180
ccagcggcgt atccggacgc caagaaacca gagagccagc cagatgccaa agggccctgc    240
catgtgccgg tgccctttcc ctctccattt gccctgccac acagtgggct ggggttgcac    300
gtgtgtttgc tgacaggcca catctctaac tgtgggccat gtggaccta ggcctgacca    360 gaccctcatg tcttcctcct tcccaggacg tgcaccacct gcacgccgag aggcgcggcc    420
ctcagccctg gcacgccgcc ctgccaagca gccctgcccc tgcccagcc acccaggagg    480 cccccaggcc tgccagcagc ctgaggccac ccaggtgcgg cgtgcctgat ccctccgatg    540
gcctgagcgc tcggaatcgg cagaagaggc acgccgaggg caccttcacc tccgacgtga    600
gcagctacct ggagggccag gccgccaagg agttcatcgc ctggctggtg aagggcaggg    660
gccgcaggga cttccctgag gaggtggcca tcgtggagga gctgggccgg cgacacgccg    720
acggcagctt cagcgacgag atgaacacca tcctggacaa cctggccgcg cgcgacttca    780
tcaactggct gatccagacc aagatcaccg atcggaagtg agcgcgctga tatc          834

<210> SEQ ID NO 17
<211> LENGTH: 780
<212> TYPE: DNA
<213> ORGANISM: Artificial
<220> FEATURE:
<223> OTHER INFORMATION: Description of sequence: DNA sequence sequence
      and translated peptide sequence of the construct according to Fig.
      1l, (see description p. 35, 38);
<220> FEATURE:
<221> NAME/KEY: CDS
<222> LOCATION: (11)..(118)
<220> FEATURE:
<221> NAME/KEY: CDS
<222> LOCATION: (387)..(776)

<400> SEQUENCE: 17
gatatccacc atg gcc ccc gcc gcc tgg ctg agg agc gcc gcc gcc agg       49
            Met Ala Pro Ala Ala Trp Leu Arg Ser Ala Ala Ala Arg
            1               5                   10 gcc ctg ctg cca ccc atg ctg ctg ctg ctg cag ccc cca cct ctg         97
Ala Leu Leu Pro Pro Met Leu Leu Leu Leu Gln Pro Pro Pro Leu
    15                  20                  25
```

```
ctg gcc cgg gcc ctg ccc ccg gtgagtgccc gccactcgcc gtccgctcct        148
Leu Ala Arg Ala Leu Pro Pro
 30              35 cgctgagggg gcgccgggca cgcgggctgg gcccagcggc gtatccggac gccaagaaac   208
cagagagcca gccagatgcc aaagggccct gccatgtgcc ggtgcccttt ccctctccat   268
ttgccctgcc acacagtggg ctggggttgc acgtgtgttt gctgacaggc cacatctcta   328
actgtgggcc atgtggacct taggcctgac cagaccctca tgtcttcctc cttcccag    386 gac gtg cac cac ctg cac gcc gag agg cgc ggc cct cag ccc tgg cac   434
Asp Val His His Leu His Ala Glu Arg Arg Gly Pro Gln Pro Trp His
             40                  45                  50 gcc gcc ctg cca agc agc cct gcc cct gcc cca gcc acc cag gag gcc   482
Ala Ala Leu Pro Ser Ser Pro Ala Pro Ala Pro Ala Thr Gln Glu Ala
 55                  60                  65 ccc agg cct gcc agc agc ctg agg cca ccc agg tgc ggc gtg cct gat   530
Pro Arg Pro Ala Ser Ser Leu Arg Pro Pro Arg Cys Gly Val Pro Asp
 70                  75                  80 ccc tcc gat ggc ctg agc gct cgg aat cgg cag aag agg cac gcc gag   578
Pro Ser Asp Gly Leu Ser Ala Arg Asn Arg Gln Lys Arg His Ala Glu
 85                  90                  95                 100 ggc acc ttc acc tcc gac gtg agc agc tac ctg gag ggc cag gcc gcc   626
Gly Thr Phe Thr Ser Asp Val Ser Ser Tyr Leu Glu Gly Gln Ala Ala
                105                 110                 115 aag gag ttc atc gcc tgg ctg gtg aag ggc agg ggc cgc agg gac ttc   674
Lys Glu Phe Ile Ala Trp Leu Val Lys Gly Arg Gly Arg Arg Asp Phe
                120                 125                 130 cct gag gag gtg gcc atc gtg gag gag ctg ggc cgg cga cac gcc gac   722
Pro Glu Glu Val Ala Ile Val Glu Glu Leu Gly Arg Arg His Ala Asp
                135                 140                 145 ggc agc ttc agc gac gag atg aac acc atc ctg gac aac ctg gcc gcg   770
Gly Ser Phe Ser Asp Glu Met Asn Thr Ile Leu Asp Asn Leu Ala Ala
150                 155                 160 cgc tga tatc                                                      780
Arg
165

<210> SEQ ID NO 18
<211> LENGTH: 720
<212> TYPE: DNA
<213> ORGANISM: Artificial
<220> FEATURE:
<223> OTHER INFORMATION: Description of sequence: DNA sequence of the
      construct according to Fig. 11, (see description p. 39);

<400> SEQUENCE: 18
gatatccacc atggccccg ccgcctggct gaggagcgcc gccgccaggg ccctgctgcc     60
acccatgctg ctgctgctgc tgcagccccc acctctgctg gccgggccc tgccccggt    120 gagtgcccgc cactcgccgt ccgctcctcg ctgaggggc gccgggcacg cgggctgggc   180
ccagcggcgt atccggacgc caagaaacca gagagccagc cagatgccaa agggccctgc   240
catgtgccgg tgccctttcc ctctccattt gccctgccac acagtgggct ggggttgcac   300
gtgtgtttgc tgacaggcca catctctaac tgtgggccat gtggacctta ggcctgacca   360
gaccctcatg tcttcctcct tcccaggacg tgcaccacct gcacgccgag aggcgcggcc   420
ctcagccctg gcacgccgcc ctgccaagca gccctgcccc tgcccagcc acccaggagg   480 cccccaggcc tgccagcagc ctgaggccac ccaggtgcgg cgtgcctgat ccctccgatg   540
gcctgagcgc tcggaatcgg cagaagaggc acgccgaggg caccttcacc tccgacgtga   600
```

```
gcagctacct ggagggccag gccgccaagg agttcatcgc ctggctggtg aagggcaggg      660
acggcagctt cagcgacgag atgaacacca tcctggacaa cctggccgcg cgctgatatc      720
```

<210> SEQ ID NO 19
<211> LENGTH: 716
<212> TYPE: DNA
<213> ORGANISM: Artificial
<220> FEATURE:
<223> OTHER INFORMATION: Description of sequence: DNA sequence and
      sequence of the translated peptide according to Fig. 1m., (see
      description p. 39, 40);
<220> FEATURE:
<221> NAME/KEY: CDS
<222> LOCATION: (11)..(118)
<220> FEATURE:
<221> NAME/KEY: CDS
<222> LOCATION: (387)..(710)

<400> SEQUENCE: 19

```
gatatccacc atg gcc ccc gcc gcc tgg ctg agg agc gcc gcc gcc agg          49
           Met Ala Pro Ala Ala Trp Leu Arg Ser Ala Ala Ala Arg
            1               5                  10 gcc ctg ctg cca ccc atg ctg ctg ctg ctg ctg cag ccc cca cct ctg         97
Ala Leu Leu Pro Pro Met Leu Leu Leu Leu Leu Gln Pro Pro Pro Leu
 15                  20                  25 ctg gcc cgg gcc ctg ccc ccg gtgagtgccc gccactcgcc gtccgctcct           148
Leu Ala Arg Ala Leu Pro Pro
 30                  35 cgctgagggg gcgccgggca cgcgggctgg gcccagcggc gtatccggac gccaagaaac      208
cagagagcca gccagatgcc aaagggccct gccatgtgcc ggtgcccttt ccctctccat      268
ttgccctgcc acacagtggg ctggggttgc acgtgtgttt gctgacaggc cacatctcta      328
actgtgggcc atgtggacct taggcctgac cagaccctca tgtcttcctc cttcccag       386 gac gtg cac cac ctg cac gcc gag agg cgc ggc cct cag ccc tgg cac        434
Asp Val His His Leu His Ala Glu Arg Arg Gly Pro Gln Pro Trp His
                 40                  45                  50 gcc gcc ctg cca agc agc cct gcc cct gcc cca gcc acc cag gag gcc        482
Ala Ala Leu Pro Ser Ser Pro Ala Pro Ala Pro Ala Thr Gln Glu Ala
         55                  60                  65 ccc agg cct gcc agc agc ctg agg cca ccc agg tgc ggc gtg cct gat        530
Pro Arg Pro Ala Ser Ser Leu Arg Pro Pro Arg Cys Gly Val Pro Asp
 70                  75                  80 ccc tcc gat ggc ctg agc gct cgg aat cgg cag aag agg cac gcc gag        578
Pro Ser Asp Gly Leu Ser Ala Arg Asn Arg Gln Lys Arg His Ala Glu
 85                  90                  95                 100 ggc acc ttc acc tcc gac gtg agc agc tac ctg gag ggc cag gcc gcc        626
Gly Thr Phe Thr Ser Asp Val Ser Ser Tyr Leu Glu Gly Gln Ala Ala
                105                 110                 115 aag gag ttc atc gcc tgg ctg gtg aag ggc agg ggc cgc agg gac ttc        674
Lys Glu Phe Ile Ala Trp Leu Val Lys Gly Arg Gly Arg Arg Asp Phe
                120                 125                 130 cct gag gag gtg gcc atc gtg gag gag ctg ggc tga gcgcgc                 716
Pro Glu Glu Val Ala Ile Val Glu Glu Leu Gly
                135                 140
```

<210> SEQ ID NO 20
<211> LENGTH: 716
<212> TYPE: DNA
<213> ORGANISM: Artificial
<220> FEATURE:
<223> OTHER INFORMATION: Description of sequence: DNA sequence of the
      construct according to Fig. 1m, (see description p. 40);

<400> SEQUENCE: 20

```
gatatccacc atggccccg ccgcctggct gaggagcgcc gccgccaggg ccctgctgcc    60
acccatgctg ctgctgctgc tgcagccccc acctctgctg gcccgggccc tgccccggt   120
gagtgcccgc cactcgccgt ccgctcctcg ctgaggggc gccgggcacg cgggctgggc   180
ccagcggcgt atccggacgc caagaaacca gagagccagc cagatgccaa agggccctgc   240
catgtgccgg tgccctttcc ctctccattt gccctgccac acagtgggct ggggttgcac   300
gtgtgtttgc tgacaggcca catctctaac tgtgggccat gtggacctta ggcctgacca   360
gaccctcatg tcttcctcct tcccaggacg tgcaccacct gcacgccgag aggcgcggcc   420
ctcagccctg gcacgccgcc ctgccaagca gccctgcccc tgccccagcc acccaggagg   480
cccccaggcc tgccagcagc tgaggccac ccaggtgcgg cgtgcctgat ccctccgatg   540
gcctgagcgc tcggaatcgg cagaagaggc acgccgaggg caccttcacc tccgacgtga   600
gcagctacct ggagggccag gccgccaagg agttcatcgc ctggctggtg aagggcaggg   660
gccgcaggga cttccctgag gaggtggcca tcgtggagga gctgggctga gcgcgc      716
```

<210> SEQ ID NO 21
<211> LENGTH: 31
<212> TYPE: PRT
<213> ORGANISM: Artificial
<220> FEATURE:
<223> OTHER INFORMATION: Description of sequence: artificial, (see description p. 40);

<400> SEQUENCE: 21

```
His Gly Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Arg Gly
            20                  25                  30
```

<210> SEQ ID NO 22
<211> LENGTH: 10
<212> TYPE: PRT
<213> ORGANISM: Artificial
<220> FEATURE:
<223> OTHER INFORMATION: Description of sequence: artificial, (see description p. 40);

<400> SEQUENCE: 22

```
Arg Arg Asp Phe Pro Glu Glu Val Ala Ile
1               5                   10
```

<210> SEQ ID NO 23
<211> LENGTH: 14
<212> TYPE: PRT
<213> ORGANISM: Artificial
<220> FEATURE:
<223> OTHER INFORMATION: Description of sequence: artificial, (see description p. 40);

<400> SEQUENCE: 23

```
Arg Arg Asp Phe Pro Glu Glu Val Ala Ile Val Glu Glu Leu
1               5                   10
```

<210> SEQ ID NO 24
<211> LENGTH: 14
<212> TYPE: PRT
<213> ORGANISM: Artificial
<220> FEATURE:
<223> OTHER INFORMATION: Description of sequence: artificial, (see

```
                      description p. 40);

<400> SEQUENCE: 24

Arg Arg Asp Phe Pro Glu Glu Val Ala Ile Ala Glu Glu Leu
1               5                   10

<210> SEQ ID NO 25
<211> LENGTH: 7
<212> TYPE: PRT
<213> ORGANISM: Artificial
<220> FEATURE:
<223> OTHER INFORMATION: Description of sequence: partial sequence
      derived from IP2

<400> SEQUENCE: 25

Asp Phe Pro Glu Glu Val Ala
1               5

<210> SEQ ID NO 26
<211> LENGTH: 10
<212> TYPE: PRT
<213> ORGANISM: Artificial
<220> FEATURE:
<223> OTHER INFORMATION: Description of sequence: sequence derived from
      SEQ ID NO: 22, wherein the first two alanines have been replaced
      by two arginines

<400> SEQUENCE: 26

Ala Ala Asp Phe Pro Glu Glu Val Ala Ile
1               5                   10

<210> SEQ ID NO 27
<211> LENGTH: 14
<212> TYPE: PRT
<213> ORGANISM: Artificial
<220> FEATURE:
<223> OTHER INFORMATION: Description of sequence: sequence derived from
      SEQ ID NO: 23, wherein the first two alanines have been replaced
      by two arginines

<400> SEQUENCE: 27

Ala Ala Asp Phe Pro Glu Glu Val Ala Ile Val Glu Glu Leu
1               5                   10

<210> SEQ ID NO 28
<211> LENGTH: 14
<212> TYPE: PRT
<213> ORGANISM: Artificial
<220> FEATURE:
<223> OTHER INFORMATION: Description of sequence: sequence derived from
      SEQ ID NO: 24, wherein the first two alanines have been replaced
      by two arginines

<400> SEQUENCE: 28

Ala Ala Asp Phe Pro Glu Glu Val Ala Ile Ala Glu Glu Leu
1               5                   10

<210> SEQ ID NO 29
<211> LENGTH: 15
<212> TYPE: PRT
<213> ORGANISM: Artificial
<220> FEATURE:
<223> OTHER INFORMATION: Description of sequence: sequence derived from
      SEQ ID NO: 2, wherein the first two arginines have been replace
      d by two alanines

<400> SEQUENCE: 29

Ala Ala Asp Phe Pro Glu Glu Val Ala Ile Val Glu Glu Leu Gly
```

```
<210> SEQ ID NO 30
<211> LENGTH: 15
<212> TYPE: PRT
<213> ORGANISM: Artificial
<220> FEATURE:
<223> OTHER INFORMATION: Description of sequence: sequence derived from
      SEQ ID NO: 3, wherein the first two arginines have been replace
      d by two alanines

<400> SEQUENCE: 30

Ala Ala Asp Phe Pro Glu Glu Val Ala Ile Ala Glu Glu Leu Gly
 1               5                  10                  15

<210> SEQ ID NO 31
<211> LENGTH: 46
<212> TYPE: PRT
<213> ORGANISM: Artificial
<220> FEATURE:
<223> OTHER INFORMATION: Description of sequence: sequence derived from
      GLP-1-IP2-fragment (murine)

<400> SEQUENCE: 31

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly Ala
            20                  25                  30

Ala Asp Phe Pro Glu Glu Val Ala Ile Ala Glu Glu Leu Gly
        35                  40                  45

<210> SEQ ID NO 32
<211> LENGTH: 46
<212> TYPE: PRT
<213> ORGANISM: Artificial
<220> FEATURE:
<223> OTHER INFORMATION: Description of sequence: sequence derived from
      GLP-1-IP2-fragment (murine)

<400> SEQUENCE: 32

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly Arg
            20                  25                  30

Arg Asp Phe Ala Glu Glu Val Ala Ile Ala Glu Glu Leu Gly
        35                  40                  45

<210> SEQ ID NO 33
<211> LENGTH: 46
<212> TYPE: PRT
<213> ORGANISM: Artificial
<220> FEATURE:
<223> OTHER INFORMATION: Description of sequence: sequence derived from
      GLP-1-IP2-fragment (murine)

<400> SEQUENCE: 33

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly Arg
            20                  25                  30

Arg Asp Ala Ala Ala Ala Val Ala Ile Ala Glu Glu Leu Gly
        35                  40                  45

<210> SEQ ID NO 34
```

```
<211> LENGTH: 46
<212> TYPE: PRT
<213> ORGANISM: Artificial
<220> FEATURE:
<223> OTHER INFORMATION: Description of sequence: sequence derived from
      GLP-1-IP2-fragment (murine)

<400> SEQUENCE: 34

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Ala
            20                  25                  30

Ala Asp Ala Ala Ala Ala Val Ala Ile Ala Ala Ala Leu Gly
        35                  40                  45

<210> SEQ ID NO 35
<211> LENGTH: 36
<212> TYPE: PRT
<213> ORGANISM: Artificial
<220> FEATURE:
<223> OTHER INFORMATION: Description of sequence: sequence derived from
      GLP-1-IP2-fragment (murine)

<400> SEQUENCE: 35

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Arg Asp Phe Pro
        35

<210> SEQ ID NO 36
<211> LENGTH: 40
<212> TYPE: PRT
<213> ORGANISM: Artificial
<220> FEATURE:
<223> OTHER INFORMATION: Description of sequence: sequence derived from
      GLP-1-IP2-fragment (murine)

<400> SEQUENCE: 36

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Arg Asp Phe Pro Glu Glu Val Ala
        35                  40

<210> SEQ ID NO 37
<211> LENGTH: 51
<212> TYPE: PRT
<213> ORGANISM: Artificial
<220> FEATURE:
<223> OTHER INFORMATION: Description of sequence: sequence derived from
      GLP-1-IP2-fragment (murine)

<400> SEQUENCE: 37

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Arg Asp Phe Pro Glu Glu Val Ala Ile Ala Glu Glu Leu Gly Arg Arg
        35                  40                  45

His Ala Cys
```

<210> SEQ ID NO 38
<211> LENGTH: 46
<212> TYPE: PRT
<213> ORGANISM: Artificial
<220> FEATURE:
<223> OTHER INFORMATION: Description of sequence: sequence derived from
      GLP-1-IP2-fragment (human)

<400> SEQUENCE: 38

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Ala
            20                  25                  30

Ala Asp Phe Pro Glu Glu Val Ala Ile Val Glu Glu Leu Gly
        35                  40                  45

<210> SEQ ID NO 39
<211> LENGTH: 46
<212> TYPE: PRT
<213> ORGANISM: Artificial
<220> FEATURE:
<223> OTHER INFORMATION: Description of sequence: sequence derived from
      GLP-1-IP2-fragment (human)

<400> SEQUENCE: 39

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Arg Asp Phe Ala Glu Glu Val Ala Ile Val Glu Glu Leu Gly
        35                  40                  45

<210> SEQ ID NO 40
<211> LENGTH: 46
<212> TYPE: PRT
<213> ORGANISM: Artificial
<220> FEATURE:
<223> OTHER INFORMATION: Description of sequence: sequence derived from
      GLP-1-IP2-fragment (human)

<400> SEQUENCE: 40

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Arg Asp Ala Ala Ala Ala Val Ala Ile Val Glu Glu Leu Gly
        35                  40                  45

<210> SEQ ID NO 41
<211> LENGTH: 46
<212> TYPE: PRT
<213> ORGANISM: Artificial
<220> FEATURE:
<223> OTHER INFORMATION: Description of sequence: sequence derived from
      GLP-1-IP2-fragment (human)

<400> SEQUENCE: 41

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Ala
            20                  25                  30

```
Ala Asp Ala Ala Ala Ala Val Ala Ile Val Ala Ala Leu Gly
        35                  40                  45

<210> SEQ ID NO 42
<211> LENGTH: 51
<212> TYPE: PRT
<213> ORGANISM: Artificial
<220> FEATURE:
<223> OTHER INFORMATION: Description of sequence: sequence derived from
      GLP-1-IP2-fragment (human)

<400> SEQUENCE: 42

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Arg Asp Phe Pro Glu Glu Val Ala Ile Val Glu Glu Leu Gly Arg Arg
        35                  40                  45

His Ala Cys
    50

<210> SEQ ID NO 43
<211> LENGTH: 31
<212> TYPE: PRT
<213> ORGANISM: Artificial
<220> FEATURE:
<223> OTHER INFORMATION: Description of sequence: sequence according to
      formula (I) (see description, p. 1)
<220> FEATURE:
<221> NAME/KEY: misc_feature
<222> LOCATION: (31)..(31)
<223> OTHER INFORMATION: Xaa = NH2, when sequence is GLP-1(7-36) amide,
      or Xaa = Gly-OH, when sequence is GLP-1(7-37) amide,

<400> SEQUENCE: 43

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 44
<211> LENGTH: 31
<212> TYPE: PRT
<213> ORGANISM: Artificial
<220> FEATURE:
<223> OTHER INFORMATION: Description of sequence:  sequence according to
      formula (II) (see description, p. 13)
<220> FEATURE:
<221> NAME/KEY: misc_feature
<222> LOCATION: (1)..(1)
<223> OTHER INFORMATION: Xaa is L-histidine, D-histidine, desamino-
      histidine, 2-amino-histidine, 3-hydroxy-histidine, homohistidine,
      N-acetyl-histidine, a-fluoromethyl-histidine, a-methyl-histidine,
      3-pyridylalanine, 2-pyridylalanine or 4-pyridylalanine;
<220> FEATURE:
<221> NAME/KEY: misc_feature
<222> LOCATION: (2)..(2)
<223> OTHER INFORMATION: Xaa is Ala, Gly, Val, Leu, Ile, Lys, or Aib;
<220> FEATURE:
<221> NAME/KEY: misc_feature
<222> LOCATION: (2)..(2)
<223> OTHER INFORMATION: Xaa is alternatively (1-aminocyclopropyl)
      carboxylic acid, (1-aminocyclobutyl) carboxylic acid, (1-
      aminocyclopentyl) carboxylic acid, (1-aminocyclohexyl) carboxylic
      acid, (1-aminocycloheptyl) carboxylic acid, or (1-aminocyclooctyl)
      carboxylic acid,
<220> FEATURE:
<221> NAME/KEY: misc_feature
<222> LOCATION: (10)..(10)
<223> OTHER INFORMATION: Xaa is Val or Leu; Xaa is is Ser, Lys or Arg;
```

```
<220> FEATURE:
<221> NAME/KEY: misc_feature
<222> LOCATION: (12)..(12)
<223> OTHER INFORMATION: Xaa is Ser, Lys or Arg;
<220> FEATURE:
<221> NAME/KEY: misc_feature
<222> LOCATION: (13)..(13)
<223> OTHER INFORMATION: Xaa is Tyr or Gln
<220> FEATURE:
<221> NAME/KEY: misc_feature
<222> LOCATION: (14)..(14)
<223> OTHER INFORMATION: Xaa is Leu or Met;
<220> FEATURE:
<221> NAME/KEY: misc_feature
<222> LOCATION: (16)..(16)
<223> OTHER INFORMATION: Xaa is Gly, Glu or Aib;
<220> FEATURE:
<221> NAME/KEY: misc_feature
<222> LOCATION: (17)..(17)
<223> OTHER INFORMATION: Xaa is Gln, Glu, Lys or Arg;
<220> FEATURE:
<221> NAME/KEY: misc_feature
<222> LOCATION: (19)..(19)
<223> OTHER INFORMATION: Xaa is Ala or Val;
<220> FEATURE:
<221> NAME/KEY: misc_feature
<222> LOCATION: (20)..(20)
<223> OTHER INFORMATION: Xaa is Lys, Glu or Arg;
<220> FEATURE:
<221> NAME/KEY: misc_feature
<222> LOCATION: (21)..(21)
<223> OTHER INFORMATION: Xaa is Glu or Leu;
<220> FEATURE:
<221> NAME/KEY: misc_feature
<222> LOCATION: (24)..(24)
<223> OTHER INFORMATION: Xaa is Ala, Glu or Arg;
<220> FEATURE:
<221> NAME/KEY: misc_feature
<222> LOCATION: (27)..(27)
<223> OTHER INFORMATION: Xaa is Val or Lys;
<220> FEATURE:
<221> NAME/KEY: misc_feature
<222> LOCATION: (28)..(28)
<223> OTHER INFORMATION: Xaa is Lys, Glu, Asn or Arg;
<220> FEATURE:
<221> NAME/KEY: misc_feature
<222> LOCATION: (29)..(29)
<223> OTHER INFORMATION: Xaa is Gly or Aib;
<220> FEATURE:
<221> NAME/KEY: misc_feature
<222> LOCATION: (30)..(30)
<223> OTHER INFORMATION: Xaa is Arg, Gly or Lys or amide or absent;
<220> FEATURE:
<221> NAME/KEY: misc_feature
<222> LOCATION: (31)..(31)
<223> OTHER INFORMATION: Xaa is Gly, Ala, Glu, Pro, Lys, amide or is
      absent;

<400> SEQUENCE: 44

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Trp Leu Xaa Xaa Xaa Xaa Xaa
            20                  25                  30

<210> SEQ ID NO 45
<211> LENGTH: 31
<212> TYPE: PRT
<213> ORGANISM: Artificial
<220> FEATURE:
<223> OTHER INFORMATION: Description of sequence: sequence according to
      formula (III) (see description, p. 13)
<220> FEATURE:
<221> NAME/KEY: misc_feature
<222> LOCATION: (1)..(1)
<223> OTHER INFORMATION: Xaa is L-histidine, D-histidine, desamino-
      histidine, 2-amino-histidine, -hydroxy-histidine, homohistidine,
```

```
      N-acetyl-histidine, a-fluoromethyl-histidine, a-methyl-histidine,
      3-pyridylalanine, 2-pyridylalanine or 4-pyridylalanine;
<220> FEATURE:
<221> NAME/KEY: misc_feature
<222> LOCATION: (2)..(2)
<223> OTHER INFORMATION: Xaa is Ala, Gly, Val, Leu, Ile, Lys or Aib;
<220> FEATURE:
<221> NAME/KEY: misc_feature
<222> LOCATION: (2)..(2)
<223> OTHER INFORMATION: Xaa is alternatively (1-aminocyclopropyl)
      carboxylic acid, (1- aminocyclobutyl) carboxylic acid, (1-
      aminocyclopentyl) carboxylic acid, (1-aminocyclohexyl) carboxylic
      acid, (1-aminocycloheptyl) carboxylic acid, or (1-aminocyclooctyl)
      carboxylic acid;
<220> FEATURE:
<221> NAME/KEY: misc_feature
<222> LOCATION: (12)..(12)
<223> OTHER INFORMATION: Xaa is Ala, Gly, Val, Leu, Ile, Lys or Aib;
<220> FEATURE:
<221> NAME/KEY: misc_feature
<222> LOCATION: (12)..(12)
<223> OTHER INFORMATION: Xaa is alternatively (1-aminocyclopropyl)
      carboxylic acid, (1- aminocyclobutyl) carboxylic acid, (1-
      aminocyclopentyl) carboxylic acid, (1-aminocyclohexyl) carboxylic
      acid, (1-aminocycloheptyl) carboxylic acid, or (1-aminocyclooctyl)
      carboxylic acid;
<220> FEATURE:
<221> NAME/KEY: misc_feature
<222> LOCATION: (16)..(16)
<223> OTHER INFORMATION: Xaa is Gly, Glu or Aib;
<220> FEATURE:
<221> NAME/KEY: misc_feature
<222> LOCATION: (17)..(17)
<223> OTHER INFORMATION: Xaa is Gln, Glu, Lys or Arg;
<220> FEATURE:
<221> NAME/KEY: misc_feature
<222> LOCATION: (20)..(20)
<223> OTHER INFORMATION: Xaa is Lys, Glu or Arg;
<220> FEATURE:
<221> NAME/KEY: misc_feature
<222> LOCATION: (24)..(24)
<223> OTHER INFORMATION: Xaa is Ala, Glu or Arg;
<220> FEATURE:
<221> NAME/KEY: misc_feature
<222> LOCATION: (28)..(28)
<223> OTHER INFORMATION: Xaa is Lys, Glu or Arg;
<220> FEATURE:
<221> NAME/KEY: misc_feature
<222> LOCATION: (29)..(29)
<223> OTHER INFORMATION: Xaa is Gly or Aib;
<220> FEATURE:
<221> NAME/KEY: misc_feature
<222> LOCATION: (30)..(30)
<223> OTHER INFORMATION: Xaa is Arg or Lys, amide or is absent;
<220> FEATURE:
<221> NAME/KEY: misc_feature
<222> LOCATION: (31)..(31)
<223> OTHER INFORMATION: Xaa is Gly, Ala, Glu or Lys, amide or is
      absent,

<400> SEQUENCE: 45

Xaa Xaa Glu Gly Thr Phe Thr Ser Asp Val Ser Xaa Tyr Leu Glu Xaa
1               5                   10                  15

Xaa Ala Ala Xaa Glu Phe Ile Xaa Trp Leu Val Xaa Xaa Xaa Xaa
                20                  25                  30
```

GLP-1 FUSION PEPTIDES

CROSS-REFERENCE TO RELATED APPLICATIONS

The present application is a continuation of U.S. patent application Ser. No. 11/991,562, filed Apr. 9, 2009 now U.S. Pat. No. 8,431,533, which is a U.S. National Phase of PCT International Application No. PCT/EP2006/009226, filed Sep. 22, 2006, which claims priority to European Application No. 05020718.2, filed Sep. 22, 2005, the disclosures of which are herein incorporated by reference in their entirety.

STATEMENT REGARDING FEDERALLY SPONSORED RESEARCH OR DEVELOPMENT

Not Applicable.

BACKGROUND OF THE INVENTION

The present invention relates to novel GLP-1 fusion peptides which have extended C termini, are resistant to endopeptidase IV inactivation, may be expressed at high levels in trans-formed animal cells, and are e.g. useful in the treatment of type 2 diabetes.

The glucagon gene is well studied, see e.g. White, J. W. et al., 1986 Nucleic Acid Res. 14(12) 4719-4730. The preproglucagon molecule as a high molecular weight precursor molecule is synthesized in pancreatic alpha cells and in the jejunum and colon L cells. Preproglucagon is a 180 amino acid long prohormone and its sequence contains, in addition to glucagon, two sequences of related structure: glucagon-like peptide-1 (GLP-1) and glucagon-like peptide-2 (GLP-2). In the preproglucagon molecule, between GLP-1 and GLP-2 is a 17 amino acid peptide sequence (or rather a 15 amino acid sequence plus the C-terminal RR cleavage site), intervening peptide 2 (IP2). The IP2 sequence (located between GLP-1 and -2 in the precursor molecule) is normally cleaved proteolytically after aa 37 of GLP-1. The preproglucagon module is therefore cleaved into various peptides, depending on the cell, and the environment, including GLP-1 (1-37), a 37 amino acid peptide in its unprocessed form. Generally, this processing occurs in the pancreas and the intestine. The GLP-1 (1-37) sequence can be further proteolytically processed into active GLP-1 (7-37), the 31 amino acid processed form, or GLP-1 (7-36) amide. Accordingly, the designation GLP-1(7-37) designates that the fragment in question comprises the amino acid residues from (and including) number 7 to (and including) number 37 when counted from the N-terminal end of the parent peptide, GLP-1. The amino acid sequence of GLP-1(7-36)amide and of GLP-1(7-37) is given in formula I (SEQ ID No.: 43): His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-X (I), which shows GLP-1(7-36)amide, when X is NH2, and GLP-1(7-37), when X is Gly-OH.

GLP-1 is a gut hormone and is the most potent endogenous insulinotropic agent with actions that include stimulating adenylate cyclase and protein kinase activity in the beta-cell. Physiologically, together with gastric inhibitory polypeptide from the upper gut, it functions as an incretin hormone lowering the blood glucose level. Accordingly, GLP-1, secreted in response to food intake, has e.g. multiple effects on the stomach, liver, pancreas and brain that work in concert to regulate blood sugar. Consequently, Glucagon-like peptide GLP-1(7-36) amide, and its non-amidated analogue GLP-1 (7-37) have attracted considerable interest because of their potent actions on carbohydrate metabolism and its potential applicability to the treatment of diabetes, including type 2 diabetes. Type 2 diabetes is characterized by insulin resistance, since cells do not respond appropriately when insulin is present. This is a more complex problem than type 1 diabetes. Type 2 diabetes may go unnoticed for years in a patient before diagnosis, since the symptoms are typically milder (no ketoacidosis) and can be sporadic. However, severe complications can result from unnoticed type 2 diabetes, including renal failure, and coronary heart disease. This leads to increased morbidity and mortality.

GLP-1 (7-36) amide or GLP-1(7-37) is short-lived in serum. The peptide is cleaved by dipeptidyl peptidase IV (DPP-IV) between residues 8 and 9. The cleaved peptide is inactive. Thus GLP-1, administered exogenously, is extremely short-lived and has limited utility in therapeutic applications.

Various attempts have been made to synthesise stabilised (against DPP-IV) analogues of naturally occurring GLP-1 (GLP-1(7-37)). In particular, the 8. residue, which in vivo is Ala, was replaced by another residue, for instance, Gly, Ser or Thr (Burcelin, R., et al. (1999) Metabolism 48, 252-258). The Gly8 or G8 analogue has been extensively tested, both as synthesised molecule, and produced by cell lines genetically engineered to secrete the mutant polypeptide (Burcelin, R., et al (1999) Annals of the New York Academy of Sciences 875: 277-285). Various other modifications have been introduced into GLP-1(7-37) to enhance its in vivo stability without compromising its biological activity. However, all of these approaches did not achieve any significant therapeutic significance due to considerable problems involved.

In WO/9953064, Thorens, B. discloses a strategy for creating a multimeric GLP-1 expression cassette which can be incorporated into a variety of cell types which are publicly available immortalised cell lines and dividing primary cell cultures. Examples include EGFresponsive neurospheres, bFGF-responsive neural progenitor stem cells from the CNS of mammals, while the worked example uses baby hamster kidney, BHK cells. The implanted transfected cells were said to have been used to treat successfully diabetic mice, allowing glucose control equivalent substantially to non-diabetic controls. However, this techniques does not comply with the requirements of a treatment to be administered routinely to diabetes patients.

Another approach to stabilize the glucose level exogeneously is based on a new class of medicines known as incretin mimetics under investigation for the treatment of type 2 diabetes. Exenatide (Byetta®) is a synthetic version of a natural compound found in the saliva of the Gila monster lizard. In clinical trials, an incretin mimetic (exenatide) has demonstrated reductions in blood sugar and improvements in markers of beta cell function. However, Exenatide exhibits only certain effects of human incretin hormone glucagon-like peptide-1 (GLP-1).

In summary, at present there is no efficient diabetes type 2 therapy available, which allows to lower the blood glucose level on the basis of GLP-1, in other words to provide a therapy which reflects the entire spectrum of beneficial effects known for GLP-1, e.g. its activity in physiological concentrations to powerfully reduce the rate of entry of nutrients into the circulation by a reduction of gastric emptying rate in obese subjects or its insulin stimulating activity. Therefore, it is an object of the present invention to provide GLP-1 based peptide molecules which are biologically active and resistant towards proteolytic degradation.

BRIEF SUMMARY OF THE INVENTION

The present invention relates to a fusion peptide comprising as component (I) N-terminally a GLP-1(7-35, 7-36 or 7-37) sequence and as component (II) C-terminally a peptide sequence of at least 9 amino acids or a functional fragment, variant or derivative thereof.

The present invention is based on the finding that the resulting inventive peptide is protected against the proteolytic degradation in vivo, mainly due to proteolytic endopeptidase IV activity. The inventive peptide having at least two components (I) and (II) exhibits GLP-1's biologically activity and, simultaneously, confers stability to the GLP-1 as its component (I) by a C-terminal elongation.

BRIEF DESCRIPTION OF THE DRAWINGS

The patent or application file contains at least one drawing executed in color. Copies of this patent or patent application with colored drawings will be provided by the Office upon request and payment of the necessary fee.

FIG. 1f illustrates a construct formed from the HincII/XbaI fragment of construct shown in FIG. 1b repetitively cloned into the SfoI/XbaI site of the construct shown in FIG. 1d. FIG. 1h is SEQ ID No.:16, FIG. 1k is SEQ ID No.: 14. FIG. 1l is SEQ ID No.: 18. FIG. 1m is SEQ ID No.: 20.

FIGS. 4 (HEK293 cells) and 5 (hTERT-MSC cells).

(FIG. 12A (GLP-1), FIG. 12B (CMl), FIG. 12C (CM3) and FIG. 12D (CM3-ANA01)).

FIG. 13A shows the effect of a treatment with saline (A), CM1 (B), CM3-ANA01 (C) or exendin (D) on the body weight of db/db mice. The mean values of 12 animals per group are plotted. FIG. 13B shows the effect of a treatment with saline (A), CM1 (B), CM3-ANA01 (C) or exendin (D) on the body weight of db/db mice.

In FIG. 16A absolute blood glucose levels during an i.p. glucose tolerance test (IPGTT) after 8 weeks of treatment with saline (A), CM1 (B), CM3-ANA01 (C) or exendin (D) is shown (mean values of each group (n=12)). Another presentation of the data presented by FIG. 16A of the blood glucose tolerance test is given in FIG. 16B.

DETAILED DESCRIPTION OF THE INVENTION

Figure 1:
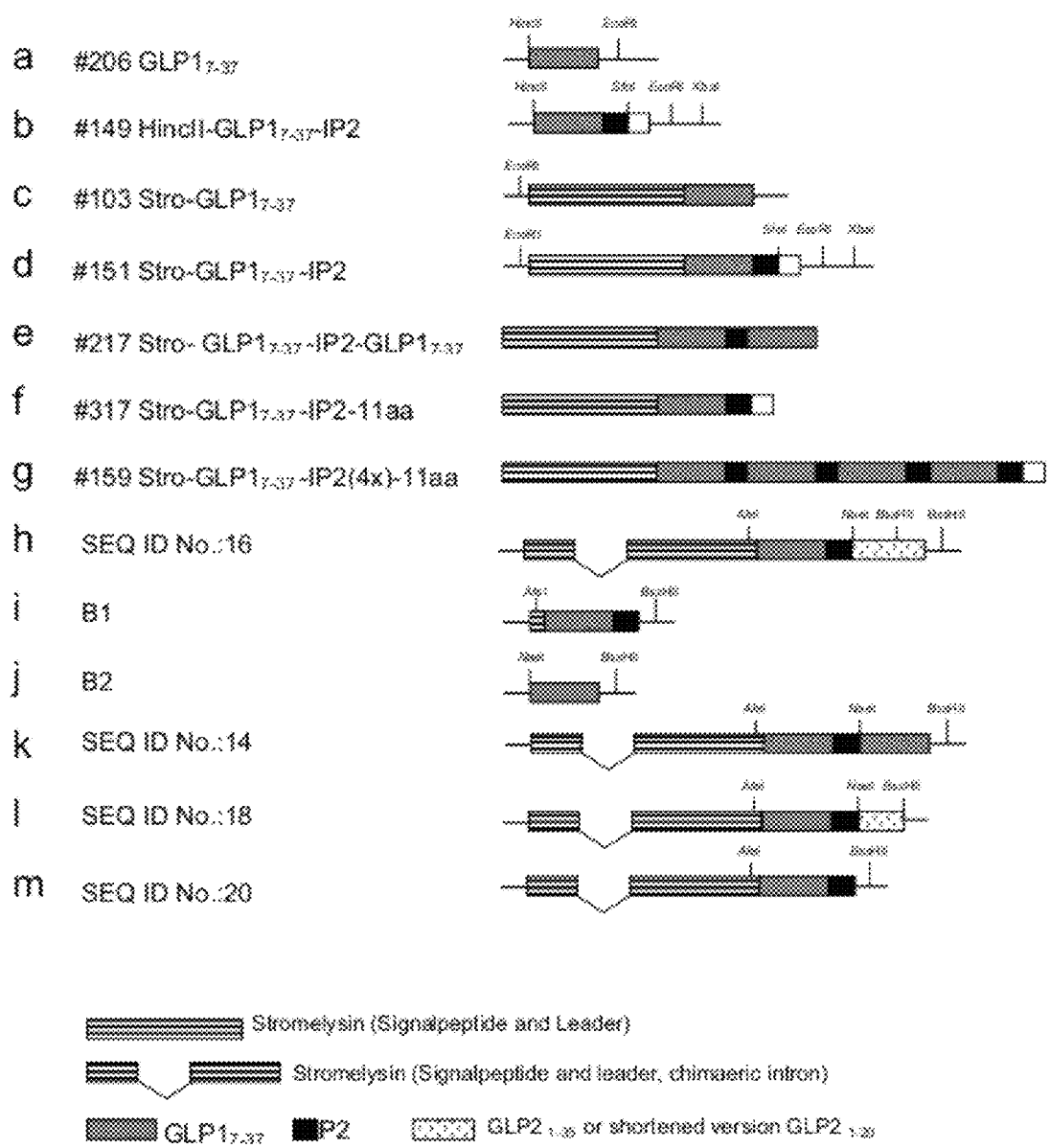
FIG. 1a illustrates the coding sequence fur GLP-1(7-37) cDNA was synthesized synthetically, in a sequence including HincII and EcoRI sites.
FIG. 1b illustrates a synthesised synthesized cDNA, including the coding sequences for GLP-1(7-37), IP2 and restriction sites for SofI, EcoRI and XbaI
FIGS. 1c and 1d illustrate a construct formed using the cDNA, encoding stromelysin signal and leader sequence was reverse transcriptase PCR amplified from human RNA. and used with the construct of FIG. 1a or FIG. 1b to form the construct shown in FIG. 1c and FIG. 1d, respectively.
FIG. 1e illustrates a construct formed from the HinCII/EcoRI fragment of the FIG. 1a construct is cloned into the SfoI site of the sequence of FIG. 1d.
FIG. 1f illustrates a construct formed from the EcoRI fragment of FIG. 1d cloned into the EcoRI site of an eukaryotic expression plasmid.
FIG. 1h illustrates a synthesized, codon optimized sequence encoding the stromelysin leader and signal sequences interrupted by a shortened endogenous intron sequence, fused to sequences encoding human GLP-1 (7-37), IP2 and GLP-2(1-35). The DNA sequence of the construct
FIGS. 1i and 1j are synthesized sequences.
FIG. 1k is a construct formed by cloning the NaeI/BssHII fragment of FIG. 1j into the NaeI/BssHII linearised sequence of FIG. 1h. The DNA sequence of the construct
FIG. 1l is a construct formed by BssHII digest and relegation of the sequence of FIG. 1h. The DNA sequence of the construct
FIG. 1m is a construct formed by cloning the AfeI/BssHII fragment of the sequence of FIG. 1i into the AfeI/BssHII linearised sequence of FIG. 1h. The DNA sequence of the construct

The present invention relates to a fusion peptide comprising as component (I) N-terminally a GLP-1(7-35, 7-36 or 7-37) sequence and as component (II) C-terminally a peptide sequence of at least 9 amino acids or a functional fragment, variant or derivative thereof.

The present invention is based on the finding that the resulting inventive peptide is protected against the proteolytic degradation in vivo, mainly due to proteolytic endopeptidase IV activity. The inventive peptide having at least two components (I) and (II) exhibits GLP-1's biologically activity and, simultaneously, confers stability to the GLP-1 as its component (I) by a C-terminal elongation.

The term "inventive peptide" as used herein is a fusion peptide as defined herein, a variant, an analog, a fragment or a derivative thereof, including combinations e.g. a derivatized fragment, analog or variant of a fusion peptide. The term "GLP-1 peptide" as used herein means GLP-1(7-35, 36 or 37), whereas "modified GLP-1 peptide" is intended to mean any GLP-1 analogue, a GLP-1 derivative, a GLP-1 variant or GLP-1 fragment, including a derivatized fragment, analog or variant of GLP-1(7-35, 36 or 37), which may occur in either component (I) and (III) of the inventive peptide. The term "GLP-2 peptide" as used herein means GLP-2 (1-33, 34, or 35), whereas "modified GLP-2 peptide" is intended to mean any GLP-2 analogue, fragment or variant, a GLP-2 derivative or a derivative of a GLP-2 analogue, including a derivatized fragment, analog or variant of GLP-2(1-33, 34 or 35). Variants, analogs, fragments and derivatives are categorized as modifications of the unmodified sequence, e.g. GLP-1(7-35, 36 or 37) or GLP-2(1-33, 34 or 35). Within the meaning of the present invention any variant, analog, fragment or derivative has to be functional, e.g. has to exert the same or a similar biological effects as the unmodified GLP-1 peptide.

Preferably, the inventive peptide is a fusion peptide or a variant, analog, fragment or derivative thereof, wherein component (I) contains a sequence having at least 80%, more preferably at least 85% and even more preferably at least 90% sequence homology with SEQ ID No.: 1. SEQ ID No.1 represents the native amino acid sequence of GLP-1(7-37) (length of 31 amino acids), which is strictly conserved among mammalians.

The second component (component (II)) of the fusion peptide according to the invention (or more generally any inventive peptide including analogs, fragments, variants or derivatives of fusion peptides) typically contains a sequence length of at least nine amino acids, which may or may not form a R-turn like structure. A R-turn structure is a typical secondary structure element of proteins or peptides. It is typically formed by four amino acids, which revert the direction of the peptide's or protein's backbone chain direction. The amino acid sequence of component (II) contains at least nine amino acids and, preferably, contains at least one proline or alanine residue in its sequence. Proline residues are common amino acids within the R turn forming tetrameric amino acid sequence. The proline residue is commonly is typically located at position 2 or 3, preferably 2, of the tetrameric R-turn sequence occurring in component (II) of the fusion peptide.

An inventive fusion may typically have in its component (II) sequence length of 9 to 30, preferably 9 to 20, and most preferably 9 to 15 amino acids. Generally spoken, shorter sequences in component (II) may be preferred due to their superior binding activity to the GLP receptor over longer sequences. The sequence of component (II), even though it is not a prerequisite, may preferably be neutral or may have a negative charge at pH7.

A fusion peptide according to the invention is preferred, if its component (II) contains a sequence motif selected from the group consisting of VAIA (SEQ ID NO: 46), IAEE (SEQ ID NO: 47), PEEV (SEQ ID NO: 48), AEEV (SEQ ID NO: 49), EELG (SEQ ID NO: 50), AAAA SEQ ID NO: 51), AA VA (SEQ ID NO: 52), AALG (SEQ ID NO: 53), DFPE (SEQ ID NO: 54), AADX, AXDX, and XADX, wherein X represents any amino acid (naturally occurring or a modified non-natural amino acid). These tetrameric motifs may be located anywhere in the sequence of component (II). In a particularly preferred embodiment, the inventive fusion peptide component (II) is a peptide sequence being linked to the C-terminus of component (I) by its N-terminal sequence motif selected from the group consisting of AA, XA, AX, RR, RX, and XR, wherein X represents any amino acid (naturally occurring or a modified non-natural amino acid).

A preferred motif of component (II) in an inventive fusion peptide contains the sequence motif SEQ ID No.: 25 (DFPE-EVA) or contains a sequence having at least 80% sequence homology with the sequence motif DFPEEVA (SEQ ID NO: 25}, which corresponds to a partial sequence of human or murine IP-2.

Particularly preferred is a fusion peptide, wherein component (II) is a peptide sequence containing a sequence according to SEQ ID No.: 22 (RRDFPEEVAI) or SEQ ID No.: 26 (AADFPEEVAI) (all peptide sequences given in the one-letter-code) or a sequence having at least 80% sequence homology with SEQ ID No.: 22 or with SEQ ID No.: 26. SEQ ID No.: 22 is a partial sequence of the full-length (human or murine) IP-2 (intervening peptide 2) sequence, which contains the N-terminal 10 amino acids of the 15 amino acid long full-length IP-2 sequence. SEQ ID No.: 26 is derived from SEQ ID No.: 22 by substitution of the N-terminal (RR) residues by (AA). IP-2 is a preferred example of a β-turn containing peptide sequence. Accordingly, other stronger preferred sequences being contained in component (II) are longer partial amino acid sequences of IP-2, such as the N-terminal 14 amino acid sequence occurring in humans (SEQ ID No.: 23 (RRDFPEEVAIVEEL)) or its murine counterpart (SEQ ID No. 24 (RRDFPEEVAIAEEL)) or a sequence having at least 80% sequence homology with SEQ ID Nos.: 23 or 24. Most preferred as elements being contained in component (II) of the fusion peptide are full-length IP-2 sequences having all 15 amino acids of the natural occurring IP-2 sequence (SEQ ID No.: 2 (RRDFPEEVAIVEELG), human, or SEQ ID No. 3 (RRDFPEEVAIAEELG), murine) or a sequence having at least 80% sequence homology with SEQ ID Nos.: 2 or 3. Within the scope of the present invention are also all mammalian isoforms of IP2 (natural variants of IP2 among mammalians). All sequences mentioned in this paragraph may also be provided with the N-terminal motif (AA), (AX) or (XA) instead of the naturally occurring (RR), e.g. SEQ ID No.: 27 (AADFPEEVAIVEEL), SEQ ID No.: 28 (AADFPEEVAIAEEL), SEQ ID No.: 29 (AADFPEEVAIVEELG), and SEQ ID NO.: 30 (AADFPEEVAIAEELG). More than one copy of a sequence being included into component (II) may be provided, e.g. 2, 3 or even more copies of IP2 or a fragment, variant or analog or derivative of IP2.

Accordingly, an inventive peptide is preferred containing a sequences according to SEQ ID No.: 8 (HAEGTFTSDVSSYLEGQAAKEFIAWLVKGRGRRDFPEEVAIAEELG), i.e. GLP-1(7-37) linked without any linker sequence via its C-terminus to murine IP2 or according to SEQ ID No.: 12 (HAEGTFTSDVSSYLEGQAAKEFI-AWLVKGRGRRDFPEEVAIVEELG), i.e. GLP-1(7-37) linked without any linker sequence via its C-terminus to human IP2. Further preferred inventive variants of the inventive peptides of SEQ ID No.:8 and SEQ ID No.: 12 are SEQ ID No.: 31 (HAEGTFTSDVSSYLEGQAAKEFI-AWLVKGRGAADFPEEVAIAEELG), SEQ ID No.: 32 (HAEGTFTSDVSSYLEGQAAKEFI-AWLVKGRGRRDFAEEVAIAEELG), SEQ ID No.: 33 (HAEGTFTSDVSSYLEGQAAKEFI-AWLVKGRGRRDAAAAVAIAEELG), SEQ ID No.: 34 (HAEGTFTSDVSSYLEGQAAKEFI-AWLVKGRGAADAAAAVAIAAALG), SEQ ID No.: 35 (HAEGTFTSDVSSYLEGQAAKEFI-AWLVKGRGRRDFP), SEQ ID No.: 36 (HAEGTFTSDVSSYLEGQAAKEFIAWLVKGRGRRDFPEEVA), SEQ ID No.: 37 (HAEGTFTSDVSSYLEGQAAKEFI-AWLVKGRGRRDFPEEVAIAEELGRRHAC), SEQ ID No.: 38 (HAEGTFTSDVSSYLEGQAAKEFI-AWLVKGRGAADFPEEVAIVEELG), SEQ ID No.: 39 (HAEGTFTSDVSSYLEGQAAKEFI-AWLVKGRGRRDFAEEVAIVEELG), SEQ ID No.: 40 (HAEGTFTSDVSSYLEGQAAKEFI-AWLVKGRGRRDAAAAVAIVEELG), SEQ ID No.: 41 (HAEGTFTSDVSSYLEGQAAKEFI-AWLVKGRGAADAAAAVAIVAALG), SEQ ID No.: 42 (HAEGTFTSDVSSYLEGQAAKEFI-AWLVKGRGRRDFPEEVAIVEELGRRHAC), i.e. GLP-1 (7-37) linked without any linker sequence via its C-terminus to specific analogs or variants of the IP2 sequence. Variants, analogs or fragments thereof having a sequence homology of at least 80% with SEQ ID Nos: 8 and 12 or derivatives thereof are encompassed as well and preferred.

Without being bound to any theory, it is concluded by the inventors of the present invention that the instability of GLP-1(7-35, 36 or 37), if administered to any patient in need thereof, is due to its unprotected 3-dimensional structure. Proteases may cleave the GLP-1(7-35, 36 or 37) peptide and abolish its physiological activity rapidly in vivo. By linking a peptide sequence to the C-Terminus of GLP-1(7-35, 36 or 37) its structure gains stability towards enzymatic degradation. Gain in stability appears to be enhanced, if the additional C-terminal peptide sequence (being contained in component (II) of the fusion peptide according to the invention) folds back due to the presence of a R-turn structural element formed by its primary structure and providing rigidity to component (II). However, a R-turn structure in component (II) of the inventive peptide does not appear to be a prerequisite for stabilizing the GLP-1 sequence of component (I) towards enzymatic degradation. The inventive peptide, by virtue of its C-terminal peptide extension, e.g. containing a R-turn structural element, is found to have improved resistance to DPP-IV inactivation. The C-terminal peptide is either not cleaved from the GLP-1(7-35, 36 or 37) sequence prior to acting on its receptor in target cells or it may be cleaved enzymatically to form GLP-1(7-35, 36 or 37) in vivo. Irrespective of the exact form of the inventive peptide bound at the site of the GLP-1 receptor, an inventive peptide exerts its function as an active insulinotropic compound.

Peptide sequences, which are considered to be suitable for being contained in component (II) due to a primary structure forming a R-turn element may readily be identified by adequate e.g. spectroscopic methods, e.g. circular dichroism, or other methods known to the skilled person.

Component (II) and component (I) may be directly linked or linked via a linker sequence. Preferably, both components are directly linked with each other. In case they are linked via a linker (or spacer), the linker is preferably a peptide linker or an organic linker. A peptide linker typically has a length of 1 to 10 amino acids, preferably 1 to 5, even more preferably 1 to 3 amino acids, in some cases the linker sequence may be even longer comprising 11 to 50 amino acids. A peptide linker may be composed of various amino acid sequences. Preferably, a peptide linker will introduce some structural flexibility between components to be linked. Structural flexibility is achieved e.g. by having a peptide linker containing various glycine or proline residues, preferably at least 30%, more preferably at least 40% and even more preferably at least 60% proline and glycine residues within the linker sequence. Irrespective of the specific sequence the peptide linker may preferably be immunologically inactive.

In a preferred embodiment of the present invention, an inventive peptide, i.e. a fusion peptide or its analogs, fragment, variants or derivatives, contains a third component (component (III)) which is either linked to the C-terminus of component (II) and/or to the N-terminus of component (I). Preferably, component (III) is located at the C-terminus of component (II). Irrespective of whether component (III) is linked to N-terminus of component (I) (by its C-terminus) or to the C-terminus of component (II) (by its N-terminus), the coupling may be direct or indirect via a linker sequence. With regard to the linker sequence it is referred to the above disclosure for a linker connecting component (I) and component (II). Generally, component (III) comprises at least four amino acid residues, preferably at least 10 additional amino acid residues, more preferably at least 20, or at least 30. In functional terms, component (III) is provided to further enhance the stability of an inventive peptide. Component (III) is expected not to interfere with the biological function of the inventive peptide which is app. comparable to the biological activity of GLP-1(7-37).

Preferably, component (III) of the inventive peptide comprises at least 4, preferably at least 10, more preferably at least 20 additional amino acid residues of the N-terminal sequence of an isoform of GLP-2 of any mammalian organism (other naturally occurring variant of GLP-2 among mammalian), e.g. murine or human isoforms as shown in SEQ ID Nos: 4 and 5. GLP-2 occurs in pro-glucagon and is also involved in carbohydrate metabolism. As with the biologically active sequence included in component (I) (GLP-1 peptide), component (III) may also comprise analogs, variants or derivatives of naturally occurring forms of GLP-2. Alternatively, component (III) may also comprise at least 4, preferably at least 10, more preferably at least 20 additional amino acid residues of the N-terminal sequence of GLP-1(7-37), correspondingly including all mammalian isoforms or—as disclosed herein—all functional variants, analogs or derivatives thereof. Generally speaking, component (III) may contain any form of a GLP-1 peptide or a modified GLP-1 peptide, which is disclosed herein as suitable for component (I) of the inventive peptide. In a further alternative, component (III) may also contain chimeric forms of GLP-1(7-37) and GLP-2. A chimeric form may be produced by coupling GLP-1(7-37) and GLP-2 (or fragments, analogs, variants or derivatives of both) with each other and by subsequently introducing this chimeric form as component (III) into the inventive peptide. Preferably, the chimeric form is composed of a partial sequence of GLP-1(7-37) and a partial sequence of GLP-2 linked together. E.g. the chimeric form may include the N-terminal 5 to 30 amino acids of GLP-1 and the C-terminal 5 to 30 amino acids of GLP-2 or vice versa, e.g amino acids 7 or 8 to 22, 23, 24, 25, 26, 27, or 28 of GLP-1(7-37) and amino acid sequence from position 15, 16, 17, 18, 19, 20, 21, 22, 23 or 24 to e.g. the C-terminus of GLP-2.

If modifications of naturally occurring forms of GLP-2 or GLP-1(7-37), respectively, are used as component (III), component (III) preferably contains the sequence of SEQ ID Nos.: 4 or 5 or SEQ ID No.: 1, respectively, or a sequence having at least 80% sequence homology with SEQ ID Nos.: 4 or 5 or SEQ ID No.: 1. Derivatives of these preferred sequences, e.g. due to side chain modifications or peptide backbone modifications etc. (as disclosed herein pertaining to "derivatives"), are also encompassed as component (III) by the present invention.

In another embodiment, component (III) may contain a plurality of sequences as described above. E.g. component (III) may contain at least two, preferably 2, 3, or 4 copies of GLP-1(7-37) and/or GLP-2 or at least two copies of sequences having at least 80% sequence homology with SEQ ID Nos: 1, 4 or 5. Also component (III) may contain more than copy of a chimeric version of GLP-1(7-37) or GLP-2, as disclosed above, e.g. eventually forming a combination of chimeric version(s) together with GLP-1(7-37) and/or GLP-2 or its modifications with at least 80% sequence homology. Within the scope of the present invention are also two or more, preferably two component (III), which may e.g. be (1) linked by its N-terminus to the C-terminus of component (II) and (2) linked by its C-terminus to the N-terminus of component (I) via a linker or directly. If two components (III) are provided, these may be identical or different.

Accordingly, inventive fusion peptides containing three components (I), (II) and (III) are particularly preferred. Four specific embodiments containing all of these components are selected from a group consisting of: SEQ ID No. 6 (N-GLP-1(7-37)-IP2(murine)-RR-GLP-1(7-37)-C, also designated murine CM1 herein), SEQ ID No. 7 (N-GLP-1(7-37)-IP2(murine)-RR-GLP2-C, also designated murine CM2 herein), SEQ ID No. 10 (N-GLP-1(7-37)-IP2(human)-RR-GLP-1(7-37)-C, also designated human CM1), and SEQ ID No. 11 (N-GLP-1(7-37)-IP2(human)RR-GLP-2-C), also designated human CM2 herein) or a sequence having at least 80% sequence homology with SEQ ID Nos.: 6, 7, 10, or 11 or a derivative thereof. All sequences 6, 7, 10 and 11 contain an RR-Linker (two arginine residues) at the C-terminus of IP2 (component (II)), which may alternatively also be discarded. Component (I) in each of the embodiments according to SEQ ID Nos:6, 7, 10 or 11 is GLP-1(7-37), whereas component (III) (in each of these embodiments linked to the C-terminus of component (II)) is either GLP-1(7-37) or GLP-2.

The inventive peptides may occur in various modified forms. These modified forms are disclosed in the following and described in more detail.

The term "salts" herein refers to both salts of carboxy groups and to acid addition salts of amino groups of the fusion peptides described above or analogs, fragments, derivatives or variants thereof. Salts of a carboxy group may be formed by means known in the art and include inorganic salts, for example, sodium, calcium, ammonium, ferric or zinc salts, and the like, and salts with organic bases as those formed, for example, with amines, such ethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the inventive peptides relevant to the present invention, i.e. the ability to reduce the rate of entry of nutrients into the circulation. As disclosed below, the salt peptide forms may be contained in a pharmaceutical formulation.

A "fragment" of a fusion peptide according to the present invention refers to any subset of the molecules, that is, a shorter peptide which retains the desired biological activity. Fragments may readily be prepared by removing amino acids from either end of the molecule and testing the resultant for its properties as a incretin. Proteases for removing one amino acid at a time from either the N-terminal and/or the C-terminal of a polypeptide are known, and so determining fragments which retain the desired biological activity involves only routine experimentation. Conclusively, fragments may be due to deletions of amino acids at the peptide termini and/or of amino acids positioned within the peptide sequence.

Additionally, the inventive peptide which has anti-diabetes type 2 activity, be it a fusion peptide itself, an analog or variant, salt, functional derivative and/or fragment thereof, can also contain additional amino acid residues flanking the inventive peptide. As long as the resultant molecule retains its resistancy or stability towards proteases and its ability to act as incretin, one can determine whether any such flanking residues affect the basic and novel characteristics of the core peptide, e.g. by its effects on pancreas cells, by routine experimentation. The term "consisting essentially of", when referring to a specified sequence, means that additional flanking residues can be present which do not affect the basic and novel characteristic of the specified inventive peptide. This term does not comprehend substitutions, deletions or additions within the specified sequence.

A "variant" according to the present invention refers to a molecule which is substantially similar to either the entire inventive peptide defined above or a fragment thereof. Variant peptides may be conveniently prepared by direct chemical synthesis of the variant peptide, using methods well known in the art. Of course, such variant of an inventive peptide would have similar anti-diabetic, e.g. insulin stimulating activity as the corresponding naturally-occurring GLP-1 peptide.

Alternatively, amino acid sequence variants of the peptides defined above can be prepared by mutations in the DNAs which encode the synthesized derivatives. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure.

An "analog" of the peptides defined above, according to the present invention, refers to a non-natural molecule which is substantially similar to either the entire molecule or to an active fragment thereof. Such analog would exhibit the same activity as the corresponding naturally-occurring GLP-1 peptide.

The types of substitutions which may be made in the inventive peptide, according to the present invention, may be based on analysis of the frequencies of amino acid changes between a homologous protein/peptide of different species. Based upon such analysis, conservative substitutions may be defined herein as exchanges within one of the following five groups:

I. Small, aliphatic, non-polar or slightly polar residues: Ala, Ser, Thr, Pro, Gly; II. Polar, negatively-charged residues and their amides: Asp, Asn, Glu, Gln; Ill. Polar, positively-charged residues: His, Arg, Lys; IV. Large, aliphatic non-polar residues: Met, Leu, Ile, Val, Cys; V. Large aromatic residues: Phe, Try, Trp.

Within the foregoing groups, the following substitutions are considered to be "highly conservative": Asp/Glu; His/Arg/Lys; Phe/Tyr/Trp; Met/Leu/Ile/Val. Semi-conservative substitutions are defined to be exchanges between two of groups (I)-(IV) above which are limited to supergroup (A), comprising(I), (II), and(III) above, or to supergroup (B), comprising (IV) and (V) above. Substitutions are not limited to the genetically encoded or even the naturally-occurring amino acids.

In general, analogs or variants of the inventive peptide may also contain amino acid substitutions, made e.g. with the intention of improving solubility (replacement of hydrophobic amino acids with hydrophilic amino acids). In one embodiment of variants/analogs of the GLP-1 peptide of the inventive peptide (occurring in component (I) and/or (III) of the inventive peptide) the (modified) GLP-1 peptide is characterized by one or more substitution(s) at positions 7, 8, 11, 12, 16, 22, 23, 24, 25, 27, 30, 33, 34, 35, 36, or 37 of the GLP-1 peptide. As an example for the following nomenclature [Arg34-GLP-1 (7-37)] designates a GLP-1 analogue wherein the naturally occurring lysine at position 34 has been substituted with arginine.

Specifically, component (I) and/or (III) of an inventive peptide may comprise variants and analogs of GLP-1(7-35, 36 or 37) including, for example, Gln9-GLP-1 (7-37), D-Gln9-GLP-1(7-37), acetyl-Lys9-GLP-1 (7-37), Thr16-Lys18-GLP-1 (7-37), and Lys18-GLP-1 (7-37), Arg34-GLP-1 (7-37), Lys38-Arg26-GLP-1 (7-38)-OH, Lys36-Arg26-GLP-1 (7-36), Arg26,34-Lys38-GLP-1 (7-38), Arg26, 34-Lys38-GLP-1(7-38), Arg26,34-Lys38-GLP-1 (7-38), Arg26,34-Lys38-GLP-1 (7-38), Arg26,34-Lys38-GLP-1 (7-38), Arg26-Lys38-GLP-1(7-38), Arg26-Lys38-GLP-1(7-38), Arg26-Lys38-GLP-1 (7-38), Arg34-Lys38-GLP-1 (7-38), Ala37-Lys38-GLP-1 (7-38), and Lys37-GLP-1 (7-37).

In another embodiment of the invention the inventive peptide contains as component (I) or (III) a modified GLP-1 peptide comprising the amino acid sequence of the following formula II (SEQ ID No.: 44):

```
Xaa7-Xaa8-Glu-Gly-Thr-Phe-Thr-Ser-Asp-Xaa16-Ser-Xaa18-Xaa19-Xaa20-Glu-Xaa22-
Xaa23-Ala-Xaa25-Xaa26-Xaa27-Phe-Ile-Xaa3o-Trp-Leu-Xaa33-Xaa34-Xaa35-Xaa36-Xaa37,
``` wherein Xaa7 is L-histidine, D-histidine, desamino-histidine, 2-amino-histidine, 3-hydroxyhistidine, homohistidine, N-acetyl-histidine, a-fluoromethyl-histidine, a-methyl-histidine, 3-pyridylalanine, 2-pyridylalanine or 4-pyridylalanine; Xaa8 is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl)carboxylic acid, or (1-aminocyclooctyl) carboxylic acid, whereby Gly is particularly preferred;

Xaa16 is Val or Leu; Xaa18 is Ser, Lys or Arg; Xaa19 is Tyr or Gin; Xaa20 is Leu or Met; Xaa22 is Gly, Glu or Aib; Xaa23 is Gin, Glu, Lys or Arg; Xaa25 is Ala or Val; Xaa26 is Lys, Glu or Arg; Xaa27 is Glu or Leu; Xaa30 is Ala, Glu or Arg; Xaa33 is Val or Lys; Xaa34 is Lys, Glu, Asn or Arg; Xaa35 is Gly or Aib; Xaa36 is Arg, Gly or Lys or amide or absent; Xaa37 is Gly, Ala, Glu, Pro, Lys, amide or is absent.

In another embodiment of the invention component (I) and/or (III) of the inventive peptide contains a modified GLP-1 peptide comprising the amino acid sequence of the following formula III (SEQ ID No.: 45):

```
Xaa7-Xaa8-Glu-Gly-Thr-Phe-Thr-Ser-Asp-Val-Ser-Xaa18-Tyr-Leu-Glu-Xaa22-Xaa23-
Ala-Ala-Xaa26-Glu-Phe-Ile-Xaa30-Trp-Leu-Val-Xaa34-Xaa35-Xaa36-Xaa37,
``` wherein Xaa7 is L-histidine, D-histidine, desamino-histidine, 2-amino-histidine, 3-hydroxyhistidine, homohistidine, N-acetyl-histidine, a-fluoromethyl-histidine, a-methyl-histidine, 3-pyridylalanine, 2-pyridylalanine or 4-pyridylalanine; Xaa8 is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid; Xaa18 is Ser, Lys or Arg; Xaa22 is Gly, Glu or Aib; Xaa23 is Gln, Glu, Lys or Arg; Xaa26 is Lys, Glu or Arg; Xaa30 is Ala, Glu or Arg; Xaa34 is Lys, Glu or Arg; Xaa35 is Gly or Aib; Xaa36 is Arg or Lys, amide or is absent; Xaa37 is Gly, Ala, Glu or Lys, amide or is absent.

In a particular preferred embodiment of the invention component (I) and/or (III) of the inventive peptide contain a (modified) GLP-1 peptide, which is selected from GLP-1 (7-35), GLP-1 (7-36), GLP-1 (7-36)-amide, GLP-1 (7-37) or an variant, analogue or derivative thereof. Also preferred are inventive peptides comprising in their components (I) and/or (III) a modified GLP-1 peptide having a Aib residue in position 8 or an amino acid residue in position 7 of said GLP-1 peptide, which is selected from the group consisting of D-histidine, desamino-histidine, 2-amino-histidine, 3-hydroxy-histidine, homohistidine, N-acetyl-histidine, a-fluoromethyl-histidine, a-methyl-histidine, 3-pyridylalanine, 2-pyridylalanine and 4-pyridylalanine.

Examples of production of amino acid substitutions in proteins which can be used for obtaining analogs for use in the present invention include any known method steps, such as presented in U.S. Pat. Nos. RE 33,653; 4,959,314; 4,588,585 and 4,737,462, to Mark et al; U.S. Pat. No. 5,116,943 to Koths et al; U.S. Pat. No. 4,965,195 to Namen et al; and U.S. Pat. No. 5,017,691 to Lee, et al, and lysine substituted proteins presented in U.S. Pat. No. 4,904,584 (Shaw et al).

Preferably, the variant or analog, as defined above and contained in component (I), (II) and/or (III), will have a core sequence, which is the same as that of the "native" sequence, e.g. GLP-1(7-37) or GLP-2 or biologically active fragment thereof or any IP2 isoform, which has an amino acid sequence having at least 70% identity to the native amino acid sequence and retains the biological activity thereof. More preferably, such a sequence has at least 80% identity, at least 90% identity, or most preferably at least 95% identity to the native sequence. Where a particular peptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide, which is 50% identical to the reference polypeptide over its entire length. Of course, other polypeptides will meet the same criteria. The term "sequence identity" as used herein means that the sequences are compared as follows. The sequences are aligned using Version 9 of the Genetic Computing Group's GAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence.

Derivatives of a fusion peptide or an analog, fragment or variant thereof are also encompassed by the present invention. The term "derivatives" of an inventive peptide is intended to include only those modified inventive peptides that do not change one amino acid to another of the twenty commonly-occurring natural amino acids. Correspondingly, a genetically encoded amino acid may be modified by reacting it with an organic derivatizing agent that is capable of reacting with selected side chains of residues or amino or carboxy groups of terminal residues (preferably by covalent modification) or by introducing non-natural amino acids (manufactured by chemical synthesis, i.e. D-isomers of the amino acids encoded by the genetic code, Aib (a-aminoisobutyric acid), Abu (a-aminobutyric acid), Tle (tert-butylglycine), p-alanine, 3-aminomethyl benzoic acid, anthranilic acid) or natural amino acids which are not encoded by the genetic code, e.g. hydroxyproline, γ-carboxyglutamate, ornithine, phosphoserine, D-alanine and D-glutamine or by a modification of the peptide backbone by alternative peptide backbone arrangements.

In the following preferred modifications of amino acids of the inventive peptide (which—as defined above—also comprises variants, analogues or fragments of the fusion peptide) are disclosed, which may occur in an inventive peptide at any site (any amino acid), e.g. positioned in component (I), (II) and/or (III).

Cysteinyl residues, if present in any form of an inventive peptide, e.g. an analogue of an inventive peptide, most commonly are reacted with alpha-haloacetates (and corresponding amines), such as chloroacetic acid or chloroacetamide, to give carboxylmethyl orcarboxyamidomethyl derivatives. Cysteinyl residues also are derivatized by reaction with bromotrifluoroacetone, alpha-bromo-beta-(5-imidazoyl)propionic acid, chloroacetyl phosphate, N-alkylmaleimides, 3-nitro-2-pyridyl disulfide, methyl-2-pyridyl disulfide, pchloromercuri benzoate, 2-chloromercuri-4-nitrophenol, orchloro-7-nitrobenzo-2-oxa-1,3-diazole.

Histidyl residues in an inventive peptide may be derivatized by reaction with diethylprocarbonate at pH 5.5-7.0 because this agent is relatively specific for the histidyl side chain. Parabromophenacyl bromide is also useful; the reaction is preferably performed in 0.1 M sodium cacodylate at pH 6.0. In particular, the N-terminal histidine residue (His7) of GLP-1(7-37) as contained in component (I) and/or (III) of the inventive peptide is very important to the insulinotropic activity of GLP-1 peptides as shown by Suzuki et. al. (Diabetes Res.; Clinical Practice 5 (Supp. 1): S30 (1988)). Correspondingly, the inventive peptide may be modified at His 7 of its GLP-1 as part of component (I) and/or (III) by alkyl or acyl (C1-C6) groups, or replacement of His with functionally-equivalent C5-C6 ring structures. A preferred modification is the introduction of a hydrophobic moiety at the amino terminus of His7 or its histidyl side chain.

Lysinyl and amino terminal residues of an inventive peptide may e.g. be reacted with succinic or other carboxylic acid anhydrides. Derivatization with these agents has the effect of reversing the charge of the lysinyl residues. By acyl (C12-C18) modifications of the epsilon-amino group of lysine residue(s) in the inventive peptide, their half-life in circulation is increased. Arginyl residues may e.g. be modified by reaction with one or several conventional reagents, among them phenylglyoxal; and ninhydrin. Derivatization of arginine residues requires that the reaction be performed in alkaline conditions because of the high pKa of the guanidine functional group. Furthermore, these reagents may react with the groups of lysine, as well as the arginine epsilon-amino group.

The specific modification of tyrosyl residues per se has been studied extensively. Most commonly, N-acetylimidazole and tetranitromethane may be used to form O-acetyl tyrosyl species and e-nitro derivatives, respectively.

Carboxyl side groups (aspartyl or glutamyl) may be selectively modified by reaction with carbodiimides (R'N—C—N—R') such as 1-cyclohexyl-3-[2-morpholinyl-(4-ethyl)] carbodiimide or 1-ethyl-3-(4-azonia-4,4-di methyl pentyl) carbodiimide.

Furthermore, aspartyl and glutamyl residues may be converted to asparaginyl and glutaminyl residues by reaction with ammonium ions.

Glutaminyl and asparaginyl residues may be deamidated to the corresponding glutamyl and aspartyl residues. Alternatively, these residues may be deamidated under mildly acidic conditions. Either form of these residues falls within the scope of this invention. Deamidated inventive peptides may undergo an altered susceptibility to proteolysis with protease or peptidase enzymes, suggesting that deamidation may have physiological significance in directing proteolytic cleavage of an inventive peptide. It is noted that biosynthetic inventive peptides may degrade under certain storage conditions, resulting in deamidation at one more positions in the inventive peptide. Methionine residues in the inventive peptides may be susceptible to oxidation, primarily to the sulfoxide. As the other derivatives mentioned above, both desamide inventive peptides and/or sulfoxide inventive peptides may be used to exhibit full biological activity.

Other suitable reagents for derivatizing alpha-amino acid-containing residues include imidoesters such as methyl picolinimidate; pyridoxal phosphate; pyridoxal; chloroborohydride; trinitrobenzenesulfonic acid; O-methyliosurea; 2,4-pentanedione; and transaminase-catalyzed reaction with glyoxylate.

The terminal amino acid residues of an inventive peptide with their carboxyl (C-terminus) and their amine (N-terminus) groups (as well as carboxyl or amide amino acid side chain groups, see above) may be present in their protected (e.g. the C terminus by an amide group) and/or unprotected form, using appropriate amino or carboxyl protecting groups. Also, acid-addition salts of the inventive peptide may be provided. Common acid addition salts are hydrohalic acid salts, i.e., HBr, HI, or more preferably, HCl.

PEGylation of terminal or side chain carboxyl groups or the epsilon-amino group of lysine occurring in the inventive peptide, confers resistance to oxidation and is also within the scope of the present invention Other modifications resulting in derivatives of inventive peptides are based on carbohydrates and/or lipids which may be covalently coupled to the inventive peptide. It is preferred to couple lipids and/or carbohydrates to serine, threonine, asparagine, glutamine or tyrosine or glutamate or aspartate via their reactive side chain moieties. Alternatively, carbohydrates and/or lipids may also be linked to the terminal moieties of the inventive peptide. Furthermore, an inventive peptide may be coupled to a functionally different peptide or protein moiety, which may also stabilize the inventive peptide and/or may serve to improve the transport properties of an inventive peptide in body fluids, in particular blood. Suitable peptides or proteins may e.g. be selected from Albumin, Transferrin etc., which are directly coupled (as component IV) to the inventive peptide or via a peptide or organic linker sequence. Preferably, these peptides or protein are linked to one of the termini of the inventive peptide.

In order to circumvent the problem of degradation of the inventive peptide another embodiment of the present invention provides a retro-inverso isomer of the inventive peptide composed of D amino acids or at least partially composed of D amino acids. The term "retro-inverso isomer" refers to an isomer of a linear peptide in which the direction of the sequence is reversed and the chirality of each amino acid residue is inverted (see, e.g., Jameson et al., Nature, 368, 744-746 (1994); Brady et al., Nature, 368, 692-693 (1994)). With respect to the parent peptide, the retro-inverso peptide is assembled in reverse order of amino acids, typically with F-moc amino acid derivatives. Typically, the crude peptides may be purified by reversed phase HPLC.

Other modifications, which may be introduced into the inventive peptides relate to modifications of the peptide backbone. Preferably, the modified inventive peptides are scaffold mimetics. Their backbone is different from the natural occurring backbone, while their side-chain structures are identical with the inventive peptides or their fragments, variants, derivatives or analogs. In general, scaffold mimetics exhibit a modification of one or more of the backbone chain members (NH, CH, CO), either as substitution (preferably) or as an insertion. Substituents are e.g. (I) —O—, —S—, or —CH$_2$— instead of —NH—; (II) —N—, C-Alkyl-, or —BH— instead of —CHR— and (III) —CS—, —CH$_2$—, —SO$_n$—, —P=O(OH)—, or —B(OH)— instead of —CO—. A peptide mimetic of an inventive peptide may be a combination of each of these modifications. In particular, modifications of each the groups I, II and III may be combined. In a peptide mimetic each backbone chain member may be modified or, alternatively, only a certain number of chain members may be exchanged for a non-naturally occurring moiety. Preferably, all backbone chain members of an inventive peptide of either —NH—, —CHR— or CO are exchanged for another non-naturally occurring group. In case the amide bond (—NH—CO—) of the inventive peptide backbone is substituted (in the entire molecule or at least in one single position), preferable substitution moieties are bioisosteric, e.g. retro-inverse amide bonds (—CO—NH—), hydroxyl ethylene (—CH(OH)—CH2-), alkene (CH2=CH—), carba (CH2-CH2-) and/or —P=O(OH)—CH2-). Alternatively, backbone chain elongation by insertions may occur in a scaffold mimetic of the inventive peptide, e.g. by moieties flanking the C-alpha atom. On either side of the C-alpha atom e.g. —O—, —S—, —CH—, —NH— may be inserted.

Particularly preferred are oligocarbamate peptide backbone structure of the inventive peptides. The amide bond is replaced by a carbamate moiety. The monomeric N-protected amino alkyl carbonates are accessible via the corresponding amino acids or amino alcohols. They are converted into active esters, e.g. p-nitro phenyl ester by using the F-moc moiety or a photo sensitive nitroatryloxycarbonyl group by solid phase synthesis.

Inventive peptides are protected against proteolytic cleavage as outlined above. They are in particular protected against dipeptidyl aminopeptidase-4 (DPP-IV). The term "DPP-IV protected" as used herein refers to a peptide according to claim 1. Inventive peptides as well as their derivatives, analogs, fragments and variants render GLP-1(7-35, 36 or 37) as part of component (I) and/or (III) of the inventive peptide resistant to the plasma peptidase (DPP-IV).

Resistance of a peptide to degradation by dipeptidyl aminopeptidase IV is determined e.g. by the following degradation assay: Aliquots of the peptides are incubated at 37 C with an aliquot of purified dipeptidyl aminopeptidase IV for 4-22 hours in an appropriate buffer at pH 7-8 (buffer not being albumin). Enzymatic reactions are terminated by the addition of trifluoroacetic acid, and the peptide degradation products are separated and quantified using HPLC or LC-MS analysis. One method for performing this analysis is: The mixtures are applied onto a Zorbax300SB-C18 (30 nm pores, 5 µm particles) 150×2.1 mm column and eluted at a flow rate of 0.5 ml/min with a linear gradient of acetonitrile in 0.1% trifluoroacetic acid (0%-100% acetonitrile over 30 min). Peptides and their degradation products may be monitored by their absorbance at 214 nm (peptide bonds) or 280 nm (aromatic amino acids), and are quantified by integration of their peak areas. The degradation pattern can be determined by using LC-MS where MS spectra of the separated peak can be determined. Percentage intact/degraded compound at a given time is used for estimation of the peptides DPP-IV stability.

An inventive peptide is defined as DPP-IV stabilised when it is 10 times more stable than the GLP-1 (7-37) based on percentage intact compound at a given time. Thus, a DPP-IV stabilised inventive peptide is preferably at least 10, more preferably at least 20 times more stable than GLP-1 (7-37) as such. Stability may be assessed by any method known to the skilled person, e.g. by adding DPP-IV to a solution of the peptide to be tested and by determining the degradation of the peptide, e.g. over time, by e.g. a spectroscopic method, Western-Blot analysis, antibody screening etc. In parallel, an inventive peptide is defined as a compound, which exerts the effect of GLP-1(7-37) by e.g. binding to its native receptor (GLP-1 receptor). Preferably, an inventive peptide has a binding affinity to the GLP-1 receptor, which corresponds to at least 10%, preferably at least 50% of the binding affinity of the naturally occurring GLP-1 peptide. The binding affinity may be determined by any suitable method, e.g. surface plasmon resonance etc. Moreover, it is preferred, if the inventive peptide evokes formation of intracellular cAMP by its binding to its extracellular receptor, which transmits the signal into the cell.

The peptides of the invention may be produced synthetically, using solid phase peptide synthesis techniques, similar to the manner of production of GLP-1 (7-36) amide and GLP-1 (7-37) in the art and can be purified afterwards on a laboratory scale e.g. by a single purification step on a reversed-phase HPLC column or suitable chromatography methods.

However, it is preferably formed in engineered cells, either in microbial cells or in animal cell lines to produce the inventive peptide. The inventive peptide may be isolated from the cells from which it is expressed, for instance using conventional separation techniques. Thus cells may be grown under appropriate conditions, for instance including support and nutrients, in vitro, and secreted protein, i.e. the inventive peptide, is recovered from the extracellular medium. The sequences engineered into cells thus preferably include leader sequences and signal peptide sequences directing secretion of the inventive peptide. The cells preferably express protease capable of cleaving the leader and signal sequences, either endogenously or by engineered gene sequences. In an alternative, the engineered gene sequences encoding an inventive peptide do not include such leader and signal peptide sequences, whereby the intracellularly expressed inventive peptide will not be secreted, and is recovered from cells by processes involving cell lysis. In such methods the coding sequences may include purification tags allowing efficient extraction of the product peptide from the medium, which tags may be cleaved to release isolated inventive peptide.

The invention further provides a nucleic acid, which codes for the inventive peptide, be it a fusion peptide or a fragment, analog or variant thereof. Any nucleic acid coding for an inventive peptides is encompassed by the present invention. Due to degeneracy of the genetic code a plurality of nucleic acid sequences may code for an inventive peptide. A nucleic acid molecule within the scope of the present invention may also contain the nucleic acid coding for the inventive peptide and, additionally, further (functional) nucleotide sequences. In a preferred embodiment of the present invention such a nucleic acid molecule may code (a) for the entire GLP-1 aa sequence (GLP-1(1-37) or the functional GLP-1(7-35, 36 or 37) sequence, (b) a cleavage sequence at the N-terminus of the GLP-1 sequence according to (a) for any protease, upstream from (b) may code for a leader sequence. In another preferred embodiment, upstream from the nucleic acid sequence coding for (b) the nucleic acid molecule may additionally comprise (c) a sequence coding for a signal peptide. Alternatively, the inventive nucleic acid molecule may have sequence (c) fused upstream from (a) without any sequence coding for a leader sequence (b) in between. Preferably, the leader sequence and signal peptide sequence are heterologous to preproglucagon.

The invention further provides a vector comprising an inventive nucleic acid (molecule) and other functional components for expression of the inventive nucleic acid (molecule). Typically, the inventive nucleic acid (molecule) will be fused to a promoter sequence and, eventually combined with other regulator sequences, e.g. an enhancer sequence. For replication, the plasmid may contain an origin of replication. In order to select cells transfected with the inventive vector, one or more antibiotic resistance gene(s) (e.g. kanamycin, ampicillin) may be provided in the vector. The vector may be a plasmid that includes bacterial original promoter, and antibiotic resistance genes and origin promoter, and antibiotic resistance genes for replication and expression in mammalian cells. The invention further provides a host cell comprising exogenously introduced DNA of the invention capable of translating the said precursor protein. The host cell may be either a prokaryotic host cell or an eukaryotic host cell, e.g. a mammalian cell.

According to a further aspect of the invention there is provided a method of treatment of an animal, preferably a human being, by administration of an inventive peptide comprising components (I) and (II) and eventually component (III). It is also provided corresponding use of such inventive peptides in the manufacture of a product for the treatment or prevention of a disease or condition associated with glucose metabolism. Non-limiting examples of glucose disorder include: diabetes mellitus type I or type II (NIDDM), or insulin resistance, weight disorders and diseases or conditions associated thereto, wherein such weight disorders or associated conditions include obesity, overweight-associated conditions, satiety deregulation, reduced plasma insulin levels, increased blood glucose levels, or reduced pancreatic beta cell mass. Preferably, use of inventive peptides for the manufacture of a medicament for the treatment of type 2 diabetes (NIDDM) is disclosed herewith. As a consequence, the present invention relates to a use of the inventive peptide e.g. for lowering weight of a subject, for reducing satiety of a subject, for post-prandially increasing plasma insulin levels in a subject, for reducing fasting blood glucose level in a subject, for increasing pancreatic beta cell mass in a subject or for treating diabetes type I or II in a subject.

Patients with other diseases or disorders may be treated by inventive peptides, i.e. fusion peptides or its analogs, fragments, variants or derivatives, as well. Inventive peptides may be used for the preparation of a medicament for the treatment of neurodegenerative disorders and diseases or conditions associated thereto and for the treatment of disorders and diseases or conditions associated to apoptosis. The use of the inventive peptide for treating these disorders results from the following: GLP-1 receptors, which are coupled to the cyclic AMP second messenger pathway, are expressed throughout the brains of rodents and humans. The chemoarchitecture of receptor distribution in the brain does not only correlate with a central role for GLP-1 in the regulation of food intake and response to aversive stress. It was also shown that GLP-1 binding at its GLP-1 receptor exerts neurotrophic properties, and offer protection against glutamate-induced apoptosis and oxidative injury in cultured neuronal cells. Furthermore, GLP-1 was shown to modify processing of the amyloid R-protein precursor in cell culture and dose-dependently reduces amyloid R-peptide levels in the brain in vivo. GLP-1 is therefore also known as regulator of the central nervous system. Inventive peptides mimicking the biological activity of physiologically active GLP-1 have therapeutic relevance to the treatment of e.g. Alzheimer's disease (AD) and other central and peripheral neurodegenerative conditions (e.g. amyotrophic lateral sclerosis (ALS), Alexander disease, Alper's disease, Ataxia telangiectasia, Canavan disease, Cockayne syndrome, Creutzfeldt-Jakob disease, Multiple Sclerosis, Sandhoff disease, Pick's disease, Spinocerebellar Ataxia, Schilder's disease and Parkinson's disease).

Moreover, it was shown that physiologically active GLP-1 exerts anti-apoptotic action on various cells, e.g. GLP-1 is beneficial to the preservation of mass and function of freshly isolated human islets or other cell types. Insofar, the biologically active inventive peptide may be used to treat disorders, which are caused by cell or tissue apoptosis.

The use of an inventive peptide may be for the manufacture of a composition which is administered exogenously, and comprises the isolated inventive peptide. The resulting composition may be used as well for the treatment of the above disorders. The disorders disclosed herein may also be treated by inventive host cells, nucleic acid (molecules) or vectors or, rather, inventive host cells, nucleic acid (molecules) or vectors may be used for the preparation of a medicament for the treatment of these disorders.

Preparation of Formulations which Contain Inventive Peptide Sequences as Active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such formulations are prepared as injectables either as liquid solutions or suspensions, preferably containing water (aqueous formulation) or may be emulsified. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

For intravenous, cutaneous or subcutaneous injection, or injection at the site of affliction, the active ingredient will be in the form of a parenterally acceptable aqueous solution which is pyrogen-free and has suitable pH, isotonicity and stability. Liquid pharmaceutical compositions generally include a liquid vehicle such as water. Preferably, the liquid vehicle will include a physiological saline solution, dextrose ethanol or other saccharide solution or glycols such as ethylene glycol, propylene glycol or polyethylene glycol or combinations thereof may be included. Further examples are other isotonic vehicles such as Ringer's Injection or Lactated Ringer's Injection.

If the invention relates to a pharmaceutical formulation comprising an aqueous solution of a compound according to the present invention, and a buffer, wherein said compound is present in a concentration from 0.1 mg/ml or above, and wherein said formulation has a pH from about 2.0 to about 10.0, preferably from about 7.0 to about 8.5. Preferably, the pH of the formulation is at least 1 pH unit from the isoelectric point of the compound according to the present invention, even more preferable the pH of the formulation is at least 2 pH unit from the isoelectric point of the compound according to the present invention.

Solid forms suitable for solution in, or suspension in, liquid prior to injection may also be prepared. The pharmaceutical formulation may be a freeze-dried formulation, whereto the physician or the patient adds solvents and/or diluents prior to use. In other words, the formulation once prepared, is not immediately administered to a subject. Rather, following preparation, it is packaged for storage in a frozen state, or in a dried form for later reconstitution into a liquid form or other form suitable for administration to a subject. In another embodiment the pharmaceutical formulation is a dried formulation (e.g. freeze-dried or spray-dried) ready for use without any prior dissolution. By "dried form" is intended the liquid pharmaceutical composition or formulation is dried either by freeze drying (i.e. lyophilization; see, for example, Williams and Polli (1984) J. Parenteral Sci. Technol. 38: 48-59), spray drying (see Masters (1991) in Spray-Drying Handbook (5th ed; Longman Scientific and Technical, Essez, U. K.), pp. 491-676; Broadhead et al. (1992) Drug Devel. Ind. Pharm. 18: 1169-1206; and Mumenthaler et al. (1994) Pharm. Res. 11: 12-20), or air drying (Carpenter and Crowe (1988) Cryobiology 25: 459-470; and Roser (1991) Biopharm. 4: 47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

It is possible that other ingredients may be present in the peptide pharmaceutical formulation of the present invention. Such additional ingredients may include wetting agents, emulsifiers, antioxidants, bulking agents, pH buffering agents (e.g. phosphate or citrate or maleate buffers), preservatives, surfactants, stabilizers, tonicity modifiers, cheating agents, metal ions, oleaginous vehicles, proteins (e.g. human serum albumin, gelatin or proteins) and/or a zwitterion (e.g. an amino acid such as betaine, taurine, arginine, glycine, lysine and histidine).

With regard to stabilizers for inventive formulations these may preferably be selected from the group of high molecular weight polymers or low molecular compounds. In a further embodiment of the invention the stabilizer is selected from polyethylene glycol (e.g. PEG 3350), polyvinylalcohol (PVA), polyvinylpyrrolidone, carboxy-hydroxycellulose or derivates thereof (e.g. HPC, HPC-SL, HPC-L and HPMC), cyclodextrins, sulphur-containing substances as mono-thioglycerol, thioglycolic acid and 2-methylthioethanol, and different salts (e.g. sodium chloride). Each one of these specific stabilizers constitutes an alternative embodiment of the invention. The pharmaceutical compositions may also comprise additional stabilizing agents, which further enhance stability of a therapeutical active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

With regard to surfactants for inventive formulations these may preferably be selected from a detergent, ethoxylated castor oil, polyglycolyzed glycerides, acetylated monoglycerides, sorbitan fatty acid esters, polyoxypropylene-polyoxyethylene block polymers (e.g. poloxamers such as Pluronie F68, poloxamer 188 and 407, TritonX-100), polyoxyethylene sorbitan fatty acid esters, starshaped PEO, polyoxyethylene and polyethylene derivatives such as alkylated and alkoxylated derivatives (tweens, e.g. Tween-20, Tween-40, Tween-80 and Brij-35), polyoxyethylenehydroxystearate, monoglycerides or ethoxylated derivatives thereof, diglycerides or polyoxyethylene derivatives thereof, alcohols, glycerol, lecitins and phospholipids (e.g. phosphatidyl serine, phosphatidyl choline, phosphatidyl ethanolamine, phosphatidyl inositol, diphosphatidyl glycerol and sphingomyelin), derivates of phospholipids (e.g. dipalmitoyl phosphatidic acid) and lysophospholipids (e.g. palmitoyllysophosphatidyl-L-serine and 1-acylsn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (e.g. cephalins), glyceroglycolipids (e.g. galactopyransoide), sphingoglycolipids (e.g. ceramides, gangliosides), dodecylphosphocholine, hen egg lysolecithin, fusidic acid derivatives (e.g. sodium tauro-dihydrofusidate etc.), long-chain fatty acids and salts thereof C6-C12 (e.g. oleic acid and caprylic acid), acylcarnitines and derivatives, N'X-acylated derivatives of lysine, arginine or histidine, or side-chain acylated derivatives of lysine or arginine N-acylated derivatives of dipeptides comprising any combination of lysine, arginine or histidine and a neutral or acidic amino acid, N-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propane-sulfonate, cationic surfactants (quaternary ammonium bases) (e.g. cetyltrimethylammonium bromide, cetylpyridinium chloride), non-ionic surfactants (e.g. Dodecyl-D-glucopyranoside), poloxamines (e.g. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention. The use of a surfactant in pharmaceutical compositions is well-known to the skilled person. For convenience reference is made to Remington: The Science and Practice of Pharmacy, 19$^{th}$ edition, 1995.

With regard to pharmaceutically acceptable preservative these may preferably be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, ethanol, chlorobutanol, and thiomerosal, bronopol, benzoic acid, imidurea, chlorhexidine, sodium dehydroacetate, chlorocresol, ethyl p-hydroxybenzoate, benzethonium chloride, chlorphenesine (3p-chlorphenoxypropane-1,2-diol) or mixtures thereof.

With regard to isotonic agents these may preferably be selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol)polyethyleneglycol (e.g. PEG400), or mixtures thereof. Any sugar such as mono-, di-, or polysaccharides, or water-solubleglucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galacititol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention.

With regard to cheating agents these may preferably be selected from salts of ethylenediaminetetraacetic acid (EDTA), citric acid, and aspartic acid, and mixtures thereof.

With regard to buffers these are preferably selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethane, hepes, bicine, tricine, malic acid, succinate, maleic acid, fumaric acid, tartaric acid, aspartic acid or mixtures thereof. Each one of these specific buffers constitutes an alternative embodiment of the invention.

The use of all of the afore-mentioned additives in pharmaceutical compositions containing the inventive therapeutic peptide is well-known to the skilled person, in particular with regard to concentration ranges of the same. For convenience reference is made to Remington: The Science and Practice of Pharmacy, 19$^{th}$ edition, 1995.

The formulations containing the inventive peptide are conventionally administered parenterally, by injection, for example, either subcutaneously, intradermally, subdermally or intramuscularly. A composition for parenteral administration of the inventive peptide may, for example, be prepared as described in WO 03/002136.

Additional formulations which are suitable for other modes of administration include suppositories and, in some cases, oral, buccal, sublingual, intraperitoneal, intravaginal, anal and intracranial formulations. For suppositories, traditional binders and carriers may include, for example, polyalkalene glycols or triglycerides; such suppositories may be formed from mixtures containing the active ingredient in the range of 0.5% to 10%, preferably 12%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10-95% of active ingredient, preferably 25-70%.

As mentioned above, additional pharmaceutical methods may be employed to control the duration of action. Controlled release preparations may be achieved by the use of polymers to complex or absorb a peptide of the present invention. The controlled delivery of the active ingredient (peptide) may be exercised by selecting appropriate macromolecules (for example, polyesters, polyamino acids, polyvinylpyrrolidone, ethylene vinylacetate copolymers, methylcellulose, carboxymethylcellulose, and protamine sulfate), the concentration of the macromolecules as well as the methods of incorporation. Such teachings are disclosed in Remington's Pharmaceutical Sciences (see above). Another possible method to control the duration of action by controlled release preparations, is to incorporate a peptide of the present invention into particles of a polymeric material such as polyesters, polyamino acids, hydrogels, poly(lactic acid) or ethylene vinylacetate copolymers.

The inventive peptides may be formulated as neutral or salt forms. A peptide of the present invention may be sufficiently acidic or sufficiently basic to react with any of a number of organic and inorganic bases, and organic and inorganic acids, to form an (addition) salt, e.g. formed with the free amino groups of the peptide. Acids commonly employed to form acid addition salts are inorganic acids such as hydrochloric acid, hydrobromic acid, hydroiodic acid, sulfuric acid, phosphoric acid, and the like, and organic acids such tartaric, asp-toluenesulfonic acid, methanesulfonic acid, oxalic acid, mandelic, p-bromophenyl-sulfonic acid, carbonic acid, succinic acid, citric acid, benzoic acid. Examples of such salts include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleat, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenyl butyrate, citrate, lactate, gammahydroxybutyrate, glycolat, tartrate, methanesulfonate, propanesulfonate, Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Acid addition salts, carboxylate salts, lower alkyl esters, and amides of the inventive peptides may be formulated according to WO 91/11457 (1991); EP 0 733 644 (1996); and U.S. Pat. No. 5,512,549 (1996).

Formulations containing the inventive peptide sequences are administered in a manner compatible with the dosage formulation, and in such amount as will be therapeutically effective. The quantity to be administered depends on the subject to be treated, including, e.g., the severity of the patient's disease. Suitable dosage ranges are e.g. of the order of several hundred micrograms active ingredient per therapeutic dose with a preferred range from about 0.1 µg to 2000 µg (even though higher amounts in the 1-10 mg range are contemplated), such as in the range from about 0.5 µg to 1000 preferably in the range from 1 µg to 500 µg and especially in the range from about 10 µg to 100 µg.

Formulations containing the inventive peptides plus e.g. additional excipients, e.g., glycine and mannitol or other additives, may be marketed in a lyophilized form as vials. A companion diluent vial is provided, allowing the patient to reconstitute the product to the desired concentration prior to administration of the dose. Inventive formulations can also be marketed in other well known manners, such as prefilled syringes, etc.

The invention is illustrated further in the accompanying examples.

EXAMPLES

Example 1

Creation of Genetic Constructs

The coding sequence for GLP-1(7-37) cDNA was synthesized synthetically, in a sequence including HincII and EcoRI sites as indicated in FIG. 1a. Separately the cDNA illustrated in FIG. 1b was synthesized, including the coding sequences for GLP-1(7-37), IP2 and restriction sites for SfoI, EcoRI and XbaI, as illustrated in FIG. 1b. To direct GLP-1 to the secretory pathway, the heterologous signal sequence of stromelysin 3 (Acc. No. NM_005940) was used. Therefore the cDNA, encoding stromelysin signal and leader sequence was reverse transcriptase PCR amplified from human RNA, and used with the construct of FIG. 1a or FIG. 1b to form the construct shown in FIG. 1c and FIG. 1d, respectively.

The HincII/EcoRI fragment of the FIG. 1a construct is cloned into the SfoI site of the sequence of FIG. 1d to form the construct FIG. 1e. Similarly, the EcoRI fragment of FIG. 1d is cloned into the EcoRI site of an eukaryotic expression plasmid, to produce the construct shown in FIG. 1f. To form the construct shown in FIG. 1g, the HincII/XbaI fragment of the construct shown in FIG. 1b is repetitively cloned into the SfoI/XbaI site of the construct shown in FIG. 1d. FIG. 1h shows a synthesized, codon optimized sequence encoding the stromelysin leader and signal sequences interrupted by a shortened endogenous intron sequence, fused to sequences encoding human GLP-1(7-37), IP2 and GLP-2(1-35). The DNA sequence of the construct FIG. 1h is SEQ ID No.:16, while SEQ ID No.:15 also shows the sequence of the translated peptide.

Also synthesized are the sequences in FIGS. 1i and 1j. These are then used to form the construct in FIG. 1k, by cloning the NaeI/BssHII fragment of FIG. 1j into the NaeI/BssHII linearised sequence of FIG. 1h. The DNA sequence of the construct FIG. 1k is SEQ ID No.: 14, while SEQ ID No.:13 also shows the sequence of the translated peptide. The construct of FIG. 1l is formed by BssHII digest and relegation of the sequence of FIG. 1h. The DNA sequence of the construct FIG. 1l is SEQ ID No.: 18, while SEQ ID No.:17 also shows the sequence of the translated peptide. The construct of FIG. 1m is formed by cloning the AfeI/BssHII fragment of the sequence of FIG. 1i into the AfeI/BssHII linearised sequence of FIG. 1h. The DNA sequence of the construct FIG. 1m is SEQ ID No.: 20, while SEQ ID No.:19 also shows the sequence of the translated peptide.

The above constructs may be made by a person skilled in the art using routine techniques.

Example 2

Transfection, Clonal Selection and GLP-1 Expression of Mammalian Cells

Source of the cells: HEK293 (human embryonic kidney cell line, # ACC 305, DSMZ Cell Culture Collection, Germany), AtT20 (Mouse LAF1 pituitary gland tumor cell line, #87021902, European Cell Culture Collection, UK), hTERT-MSC cells are generated by Prof. Kassem, University Hospital of Odense, Denmark.

For transfection of $10^6$ cells 0, 5-2 µg plasmid DNA with different GLP-1 constructs was used. The constructs were generated as described in Example 1. HEK293 cells were transfected by standard calcium phosphate co-precipitation method as described in Current Protocols in Molecular Biology (Ausubel et al. 1994ff Harvard Medical School Vol2., Unit 9.1). AtT20 cells were transfected using FuGene (Roche) as described in current Protocols in Molecular Biology (Ausubel et. al. 1994ff, Harvard Medical School Vol 2., Unit 9.4). Transfection of hTERT-MSC cells was performed using the Nucleofector technology (Amaxa), a non-viral method which is based on the combination of electrical parameters and cell-type specific solutions. Using the Nucleofector device (program C17) and the Nucleofector solution VPE-1001 transfection efficiencies >60% have been achieved. 48 hours after transfection selection of cell clones with stable integration of DNA into the chromosome was performed by adding the selective agent blasticidin (2 μg/ml) into the culture medium. 12-15 days later, stable transfected cell clones could be isolated and expanded for characterisation.

Figure 2:
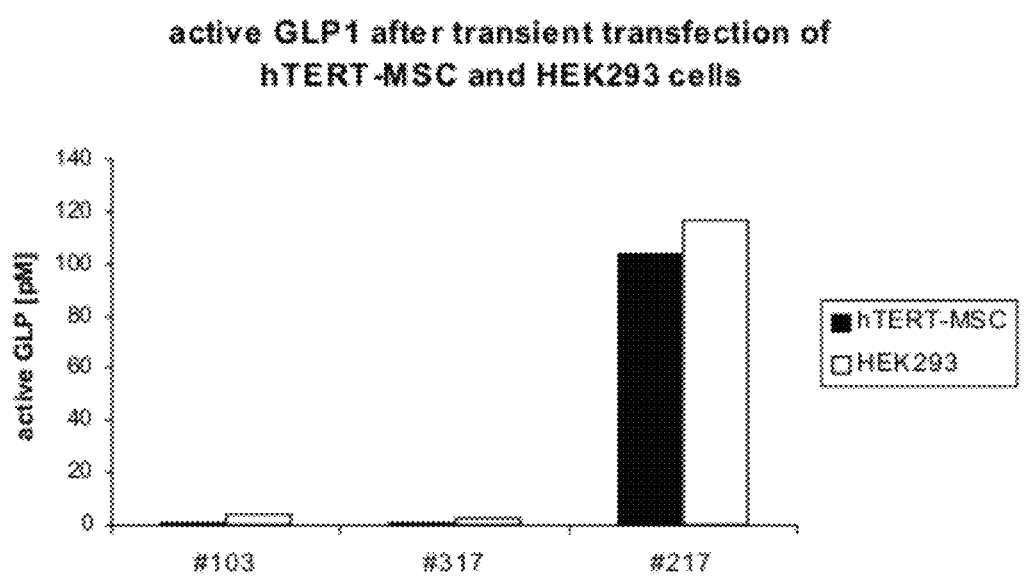
FIG. 2 illustrates a summary of results of Transient expression of different GLP-1 constructs measured in hTERT-MSC and HEK293 cells. Whereas only marginal active GLP-1 level can be found in the monomeric GLP-I constructs #103 and #317 (having just one copy of GLP-1 (7-37) an enormous gain in expression can be found in the dimeric GLP-1 construct #217 (having GLP-1(7-37) as component (I) and as component (III)) both in hTERT-MSC and in HEK293 cells.

Transient expression of different GLP-1 constructs was measured in hTERT-MSC and HEK293 cells. Whereas only marginal active GLP-1 level can be found in the monomeric GLP-1 constructs #103 and #317 (having just one copy of GLP-1(7-37)) an enormous gain in expression can be found in the dimeric GLP-1 construct #217 (having GLP-1(7-37) as component (I) and as component (III)) both in hTERT-MSC and in HEK293 cells. Results are summarized in FIG. 2. An elongation of the construct to the GLP-1 construct #159 (having four IP2 copies as component (II)) results in no further significant increase (not shown). After transfection of hTERT-MSC cells with different constructs clones were selected, which stably express GLP-1. The expression levels are shown in Table 1.

TABLE 1

| construct | cell clone | active GLP per $10^6$ cells and hour [pmol] |
|---|---|---|
| #103 GLP1$_{(7-37)}$ | 49TM113/13 | 0.4 |
| #317 GLP1$_{(7-37)}$-IP2-11aa | 71TM169/1 | 0.3 |
| #217 GLP1$_{(7-37)}$-IP2-GLP1$_{(7-37)}$ | 79TM217/13 | 2.7 |

Example 3

Western Blot Analysis of GLP-1 Peptides, Secreted from Mammalian Cells

Cell culture supernatant from GLP-1 secreting cells was separated in a 10%-20% gradient SDS PAGE (120V, 90 minutes) and transferred to a PVDF membrane (Immobilon-P Membrane 0.45 μm Millipore IPVH 00010) by semi-dry blotting (2.0 mA/cm2, 60 minutes). After methanol fixation and blocking (3% (w:v) BSA, 0.1% (v:v) Tween-20 in TBS) the membrane was immunoblotted with 1 μg/ml anti-GLP-1 antibody (HYB 147-12, Antibodyshop) at 4° C. o/n. After washing and incubation with 0.02 μg/ml detection antibody (Anti Mouse IgG, HRP conjugated, Perkin Elmer PC 2855-1197) at RT for 4 hours, chemiluminescence detection reveals the location of the protein.

Figure 3:
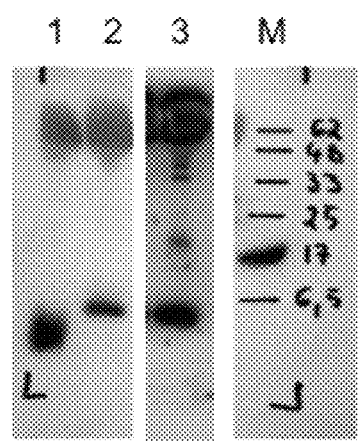
FIG. 3 illustrates Western Blot Analysis. (1: 100 ng synthetic GLP-1 (7-37) dissolved in supernatant of mock transfected hTERT-MSC cells, 2: supernatant of hTERT-MSC cells (clone 79TM217/13) secreting dimeric GLP-1 from construct #217, 3: supernatant of AtT20 cells (clone 81-A-217/3) secreting dimeric GLP-1 from construct #217; M: prestained protein marker [kDa]). The results show that inventive peptides containing GLP-1(7-37) and a C-terminal appendix (2 and 3 in FIG. 3) are secreted from the transfected cell lines and can be detected using an anti-GLP-1 antibody, which binds to the mid-molecular epitopes of GLP-1 (7-37).

Western Blot Analysis is shown in FIG. 3 (1: 100 ng synthetic GLP-1(7-37) dissolved in supernatant of mock transfected hTERT-MSC cells, 2: supernatant of hTERT-MSC cells (clone 79TM217/13) secreting dimeric GLP-1 from construct #217, 3: supernatant of AtT20 cells (clone 81-A-217/3) secreting dimeric GLP-1 from construct #217; M: prestained protein marker [kDa]). The results show that inventive peptides containing GLP-1(7-37) and a C-terminal appendix (2 and 3 in FIG. 3) are secreted from the transfected cell lines and can be detected using an anti-GLP-1 antibody, which binds to the mid-molecular epitopes of GLP-1(7-37).

Example 4

In Vitro Plasma Stability of GLP-1 Peptides Secreted from Human Cells

HEK293 and hTERT-MSC cells were transiently transfected with constructs, encoding the heterologous stromelysin signal sequence, which is linked to GLP-1 variants encoding the following peptides:
1: GLP-1(7-37)
2: GLP-1(7-37)-IP2-extended with 11 AA
3: GLP1(7-37)-IP2-GLP1(7-37)
Cell culture supernatant, containing GLP-1 peptides secreted from cells or synthetic GLP-1(7-37) (Bachem) was incubated with human lymphocyte enriched plasma containing dipeptidylpeptidase activity at 37° C. and 5% $CO_2$, for 3 or 4 hours. Synthetic GLP-1(7-37) in supernatant from mock transfected cells was used as a positive control for DPP-IV activity, which was shown to be inhibited by addition of an DPP-IV inhibitor (#DPP4, Biotrend). Active GLP was measured using the GLP-1 (Active) ELISA (#EGLP-35K, Biotrend), using an antibody which binds to the N-terminal epitope of GLP-1(7-37) discriminating the DPP-IV degraded, inactive GLP-1(9-37) peptide.

Figure 4:
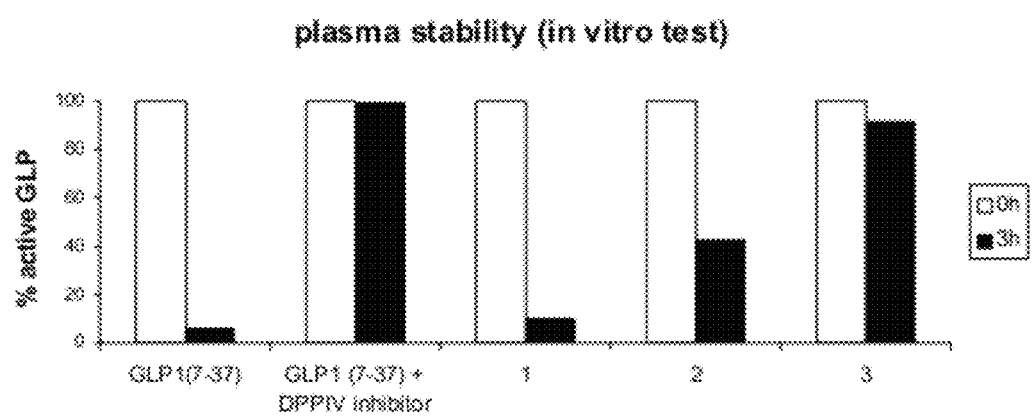
FIGS. 4 and 5 illustrate Cell culture supernatant, containing GLP-I peptides secreted from cells or synthdic GLP-1(7-37) (Bachem) was incubated with human lymphocyte enriched plasma containing dipeptidylpeptidase activity at 37° C., and 5% $CO_2$, for 3 or 4 hours. Synthetic GLP-1(7-37) in supernatant from mock transfectcd cells was used as a positive control for DPP-IV activity, which was shown to be inhibited by addition of an DPP-IV inhibitor (#DPP4, Biotrend). Active GLP was measured using the GLP-1 (Active) ELISA (#EGLP-35K, Biotrend), using an antibody which binds to the N-terminal epitope of GLP-1 (7-37) discriminating the DPP-IV degraded) inactive GLP-1 (9-37) peptide.
Figure 5:
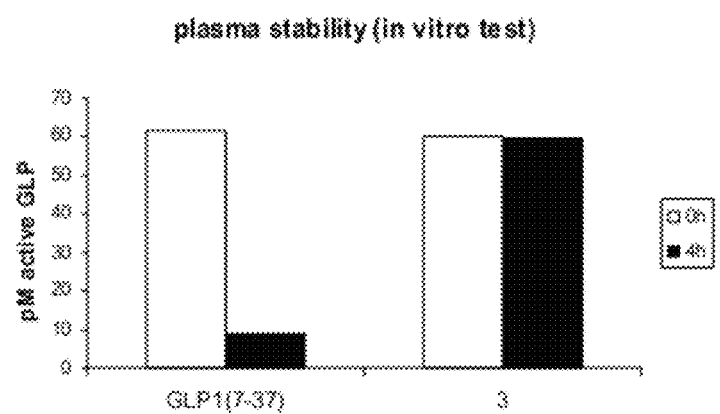

The results are shown in FIGS. 4 (HEK293 cells) and 5 (hTERT-MSC cells). HEK293 and hTERT-MSC cells are both effective hosts for the gene construct. The numbering of the results for the transfected cells of types 1 to 3 is as with Example 3 (1: 100 ng synthetic GLP-1(7-37) dissolved in supernatant of mock transfected hTERT-MSC cells, 2: supernatant of hTERT-MSC cells (clone 79TM217/13) secreting dimeric GLP-1 from construct #217, 3: supernatant of AtT20 cells (clone 81-A-21713) secreting dimeric GLP-1 from construct #217). While construct 1 produces wild type GLP-1 which is inactivated by DPP-IV in a similar way to synthetic GLP-1, the inventive C-terminally elongated GLP-1 forms (2 and 3 in FIG. 4, 3 in FIG. 5) are more resistant to degradation and maintain at least 40% activity. The C-terminal extended GLP-1 peptides are significantly stabilised in human plasma in vitro. The peptide with the dimeric GLP-1 sequence (3) is nearly fully stabilised to DPP-IV degradation in vitro.

Example 5

Western Blot Analysis of GLP-1 Peptides

Figure 6:
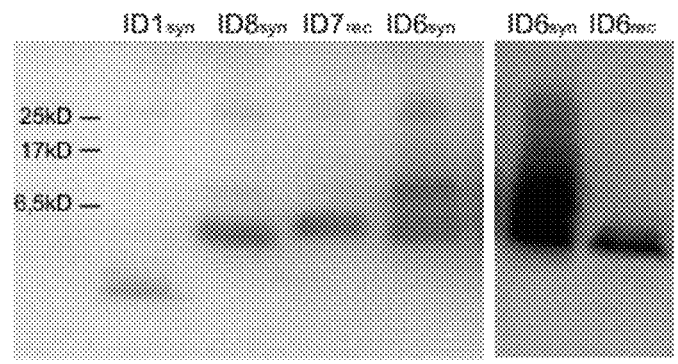
FIG. 6 illustrates a Western Blot for the peptides indicated.

Various GLP-1 peptides were produced synthetically by solid phase (syn) or recombinant using $E.\ coli$ (rec). GLP-1 peptides (31 ng SEQ ID No:1 and 10 ng of each SEQ ID No:6, SEQ ID No:7, SEQ ID No:8) were separated in a 10%-20% gradient SDS PAGE (120V, 90 minutes) and transferred to a PVDF membrane (Immobilon-P Membran 0.45 μm Millipore IPVH 00010) by semi-dry blotting (2.0 mA/cm$^2$, 60 minutes). After methanol fixation and blocking (3% (w:v) BSA, 0.1% (v:v) Tween-20 in TBS) the membrane was immunoblotted with 1 μg/ml anti-GLP-1 antibody (HYB 147-12, Antibodyshop) at 4° C. o/n. After washing and incubation with 0.02 μg/ml detection antibody (Anti Mouse IgG, HRP conjugated, Perkin Elmer PC 2855-1197) at RT for 4 hours, chemiluminescence detection reveals the location of the protein. FIG. 6 shows a Western Blot for the peptides indicated. The following values can be given: SEQ ID No.: 1 (ID1syn) corresponds to GLP-1(7-37), 31 aa, 3.3 kD; SEQ ID No.:8 (ID8 syn, CM3) corresponds to GLP-1(7-37)-IP2, 46 aa, 5.1 kD; SEQ ID No.: 7 (ID7rec, CM2) corresponds to GLP-1(7-37)-IP2-RR-GLP2, 83 aa, 9.4 kD; SEQ ID No.: 6 (ID6syn, CM1) corresponds to GLP-1(7-37)-IP2-RR-GLP1 (7-37), 79 aa, 8.7 kD.

Example 6

In Vitro Human Plasma Stability of GLP-1$^{CM}$ Peptides

Synthetic GLP-1 peptides (SEQ ID No:1$_{syn}$, SEQ ID No:6$_{syn}$, SEQ ID No:7$_{rec}$, SEQ ID No:8$_{syn}$) were incubated at concentrations of 20 ng/ml with human plasma at 37° C. and 5% $CO_2$ for 3 hours. Dipeptidylpeptidase activity of the plasma was inhibited by an DPP-IV inhibitor (#DPP4, Biotrend). Active GLP was measured using the GLP-1 (Active) ELISA (#EGLP-35K, Biotrend).

Figure 7:
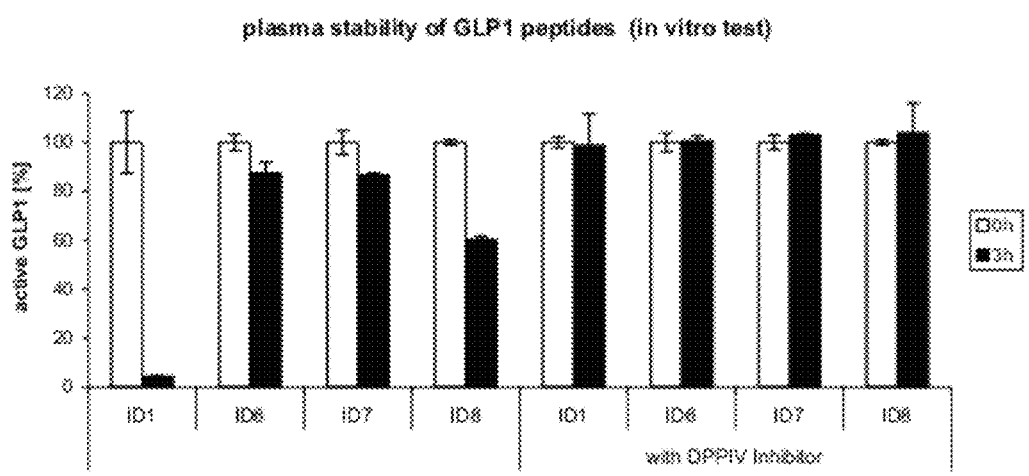
FIG. 7 illustrates in contrast to the native GLP-I.sub(3-37) (SEQ ID No: I) the inventive C-terminal elongated GLP-1 peptides SEQ ID No:6, SEQ ID No:7, and SEQ ID No:8 are significantly stabilized in human plasma in vitro. As control (on the right hand side) the results obtained for experiments with addition of DPP-IV are shown. GLP-1 activity is completely maintained in these control experiments.

In contrast to the native GLP-1$_{(7-37)}$ (SEQ ID No:1) the inventive C-terminal elongated GLP-1 peptides SEQ ID No:6, SEQ ID No:7, and SEQ ID No:8 are significantly stabilized in human plasma in vitro (FIG. 7). As control (on the right hand side) the results obtained for experiments with addition of DPP-IV are shown. GLP-1 activity is completely maintained in these control experiments.

Example 7

Bioassay In Vitro

Cyclic AMP Production

RIN-5F cells (rat islet cell tumor; ECACC No. 95090402) were grown in 24-well plates for 4 days reaching 70% confluence. Cells were washed twice with DMEM (E15-009, PAA) before addition of 0.5 ml DMEM (E15-009, PAA) supplemented with 1% HSA (Aventis), 0.2 mM IBMX (858455, Sigma) and the test peptides. After a 20 minute incubation at 25° C., cells were washed twice with ice cold PBS. Cellular cAMP was extracted by addition of 0.1 N HCl containing 0.5% Triton X-100. Cyclic AMP was quantified using the cAMP (low pH) EIA (Cat. DE0355, R&D). For stimulation $3*10^{-8}$ M SEQ ID No:1, SEQ ID No:6$_{syn}$, SEQ ID No:6$_{rec}$, SEQ ID No:7$_{rec}$, SEQ ID No:8$_{syn}$ have been used.

Figure 8:
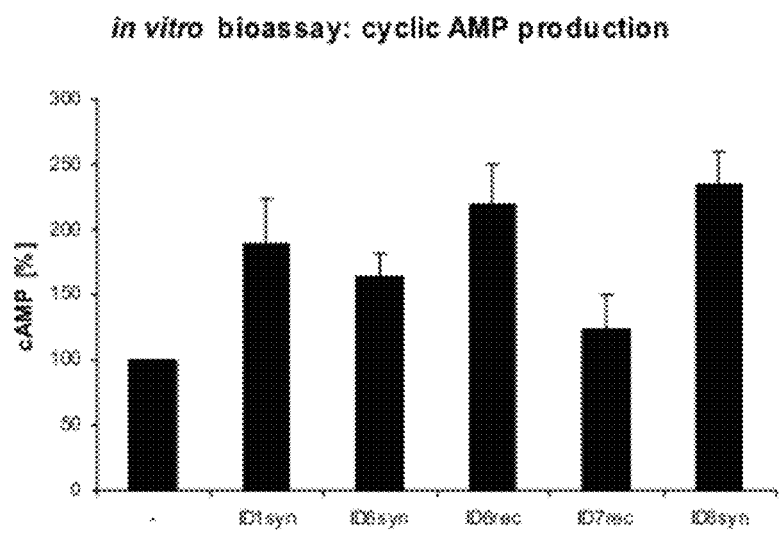
FIG. 8 illustrates the results of RIN-5F cells (rat islet cell tumor; ECACC No. 95090402) were grown in 24-well plates for 4 days reaching 70% confluence. Cells were washed twice with DMEM (E15-009, PAA) before addition of 0.5 ml DMEM (EIS-009, PAA) supplemented with 1% HSA (Aventis), 0.2 mM IBMX (858455, Sigma) and the test peptides. After a 20 minute incubation at 25° C., cells were washed twice with ice cold PBS. Cellular cAMP was extracted by addition of 0.1 N HCl containing 0.5% Triton X-100. Cyclic AMP was quantified using the cAMP (low pH) EIA (Cat DE0355, R&D). For stimulation $3 \times 10^{-8}$ M SEQ ID No: 1, SEQ ID No:$6_{syn}$, SEQ ID No:$6_{rec}$, SEQ ID No:$7_{rec}$, SEQ ID No:$8_{syn}$ have been used.

Results are shown in FIG. 8. 100% cAMP production corresponds to the basal production in the absence of GLP-1. GLP-1 binds to G protein-coupled receptors and stimulates cAMP production. All molecules tested increase the cellular cAMP production.

Example 8

In Vivo Bioactivity 11-week-old type II diabetic mice (C57BL/Ks-Lepr$^{db/db}$, Harlan) were treated with 5 µg peptide by subcutaneous injection twice a day at 9 a.m. and 5 p.m. (n=5 per group). Blood glucose was measured before (day 0) and after treatment with GLP$^{CM}$ peptides (Day 2, 4, 7, 10) at 10 a.m. after an overnight fastening period. Data were presented in relation to blood glucose levels measured at day 0.

Figure 9:
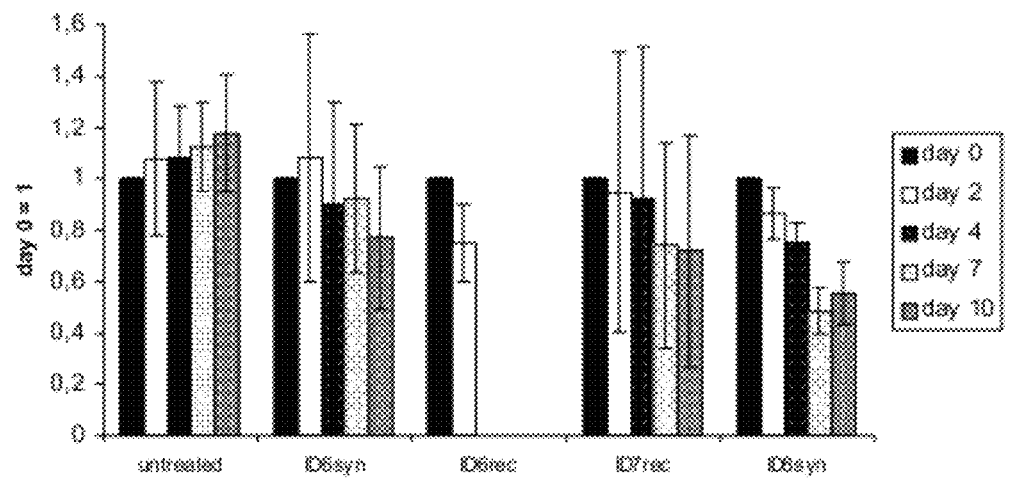
FIG. 9 illustrates (y-axis) the relative effect of the treatment is shown. Blood glucose at day=0 was set to 1. Untreated animals undergo continuous increase in blood glucose level over time, whereas animals treated with inventive peptides display grosso modo a continuous decrease of the blood glucose level over time.

All inventive peptides tested (SEQ ID No.:6 (synthetic or recombinant) and SEQ ID No.:7 (synthetic or recombinant)) have an anti-hyperglycemia effect. Best results were obtained with recombinant SEQ ID No.:6 (CM1) and synthetic SEQ ID No.:8 (CM3). In FIG. 9 (y-axis) the relative effect of the treatment is shown. Blood glucose at day=0 was set to 1. Untreated animals undergo continuous increase in blood glucose level over time, whereas animals treated with inventive peptides display grosso modo a continuous decrease of the blood glucose level over time.

Example 9

Measurement of In Vitro Plasma Stability of GLP1$^{CM}$ Peptides

Kinetic Test Method

Aliquots of 1 µM peptide in incubation buffer (50 mM Triethanolamin-HCl (pH 7.8), 0.2% HSA) from CM3, Alanin substituted CM3 analogs (CM3-ANA01, CM3-ANA02, CM3-ANA03, CM3-ANA04), C-terminally shortened CM3 analogs (CM3-ANA06, CM3-ANA07) or C-terminally elongated CM3 analogs (CM3-ANA09) were incubated with 10% human plasma at 37° C. and 5% $CO_2$ for 0, 3, 6 and 9 hours. Dipeptidylpeptidase activity was stopped by addition of DPPIV inhibitor (#DPP, Biotrend) and active GLP-1 levels determined using the GLP-1 (active) ELISA (#EGLP-35K, Linco). Results are from triplicates in at least two independent experiments.

Inventive peptides having at least nine amino acids added to the C-terminus of GLP-1 are CM3 (murine, GLP-1(7-37)-IP2) and derivatives thereof with modified sequences in component (II) (IP2), i.e. CM3-ANA01, CM3-ANA01, CM3-ANA02, CM3-ANA03, CM3-ANA04, CM3-ANA05, CM3-ANA07, CM3-ANA07. Peptides GLP-1 and CM3-ANA06 reflect control or reference substances.

Figure 10:
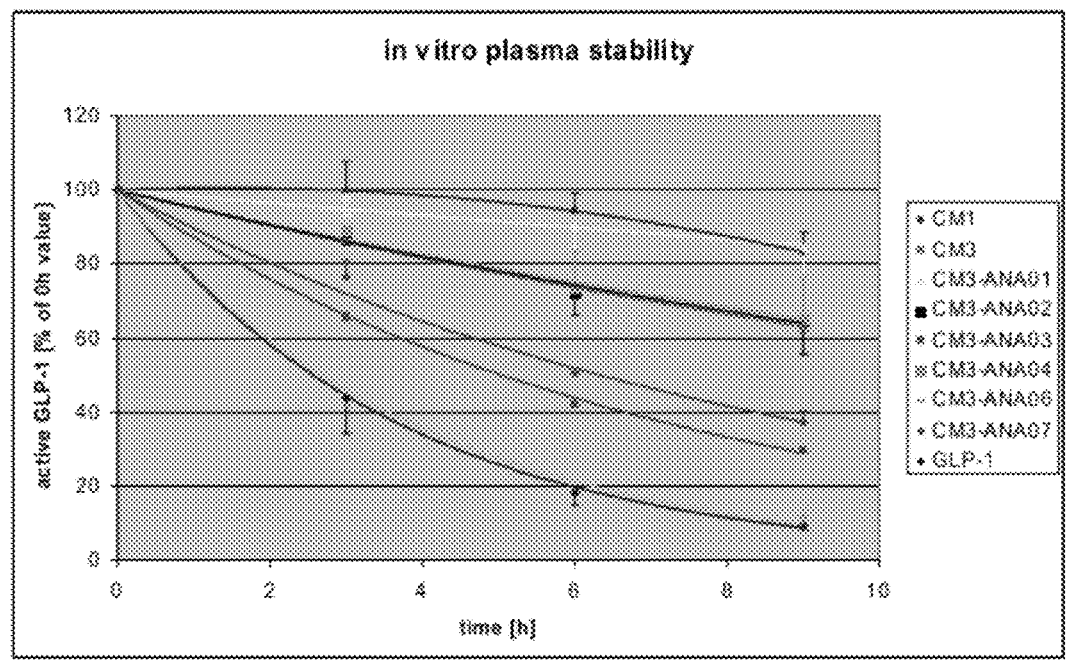
FIG. 10 illustrates the active portion of active GLP-1 as a % of the 0 h value (0 h=100%).

FIG. 10 shows the active portion of active GLP-1 as a % of the 0 h value (0 h=100%). It is clearly seen that GLP-1 has the worst plasma stability with only 9% left after 9 h plasma exposure. CM3-ANA01 shows the best stability values with 84% material left after 9 h. Inventive peptides have a remainder of at least 30% after 9 h, whereas peptides with shorter extensions do not reach these values. From the kinetics, a time can be determined, which is needed to degrade active GLP-1 to 80% of the 0 h value (DT$_{80}$: 80% degradation time) for the substances tested.

Sequences listed by increasing DT$_{80}$ values:

| Peptide | SEQ ID Nos | Sequence | DT$_{80}$ (h) | 9h value (%) |
|---|---|---|---|---|
| GLP-1 | 1 | HAEGTFTSDVSSYLEGQAAKEFIAWLVKGRG | 0.8 | 9 |
| CM3-ANA06 | 35 | HAEGTFTSDVSSYLEGQAAKEFIAWLVKGRGRRDFP | 0.9 | 11 |
| CM3-ANA03 | 33 | HAEGTFTSDVSSYLEGQAAKEFIAWLVKGRGRRDAAAAVAIAEELG | 1.6 | 30 |
| CM3-ANA07 | 36 | HAEGTFTSDVSSYLEGQAAKEFIAWLVKGRGRRDFPEEVA | 2.0 | 37 |
| CM3-ANA09 | 37 | HAEGTFTSDVSSYLEGQAAKEFIAWLVKGRGRRDFPEEVAIAEELGRRHAC | 4.2 | 60 |
| CM3 | 8 | HAEGTFTSDVSSYLEGQAAKEFIAWLVKGRGRRDFPEEVAIAEELG | 4.4 | 63 |
| CM3-ANA02 | 32 | HAEGTFTSDVSSYLEGQAAKEFIAWLVKGRGRRDFAEEVAIAEELG | 4.5 | 65 |

-continued

| Peptide | SEQ ID Nos | Sequence | $DT_{80}$ (h) | 9h value (%) |
|---|---|---|---|---|
| CM3-ANA04 | 34 | HAEGTFTSDVSSYLEGQAAKEFIAWLVKGRGAADAAAAVAIAAALG | 4.7 | 65 |
| CM3-ANA01 | 31 | HAEGTFTSDVSSYLEGQAAKEFIAWLVKGRGAADFPEEVAIAEELG | 12.5 | 84 |

The inventive substances show a considerably longer in vitro plasma stability as compared to the reference substances. Without being bound to any theory, the C-terminal elongation of GLP-1 introduces a steric hindrance, preventing these analogs to enter the active site of the DPPIV, and thus escape degradation, whereas shorter reference substances do not show this protecting effect for GLP-1 stability. This hypothesis is supported by the continuously increasing stability of cumulative C-terminal elongations of the peptides CM3-ANA06 (36aa), CM3-ANA07 (40aa) and CM3 (46aa). Nevertheless this phenomenon is not only dependent on the pure number of amino acids, which has been shown by Alanin substitutions in the IP2 region of CM3. The CM3-ANA03 peptide, which has the same number of amino acids like CM3, has a strongly reduced stability compared to CM3. On the other hand CM3-ANA01, which also consists of 46 amino acids, has a higher plasma stability than CM3. This may indicate that beside the number of amino acids, additional steric effects may influence the stability. Particularly preferred are peptides having an elongation comprising IP2 at the C-terminus of GLP-1 or an elongation having a certain degree of homology with IP2, which may result from a specific conformation, which hinders the N-terminal region from entering the active site of DPP-IV.

Example 10

In Vivo Study

Immunogenicity

To elucidate potential immunogenicity of test substance CM1 a mouse study was performed at Parabioscience (Groningen, Germany). The trial was done in BALB/c mice receiving 5 repeated injections (70 μg peptide/dose, i.v.) over 22d (n=5).

Figure 11:
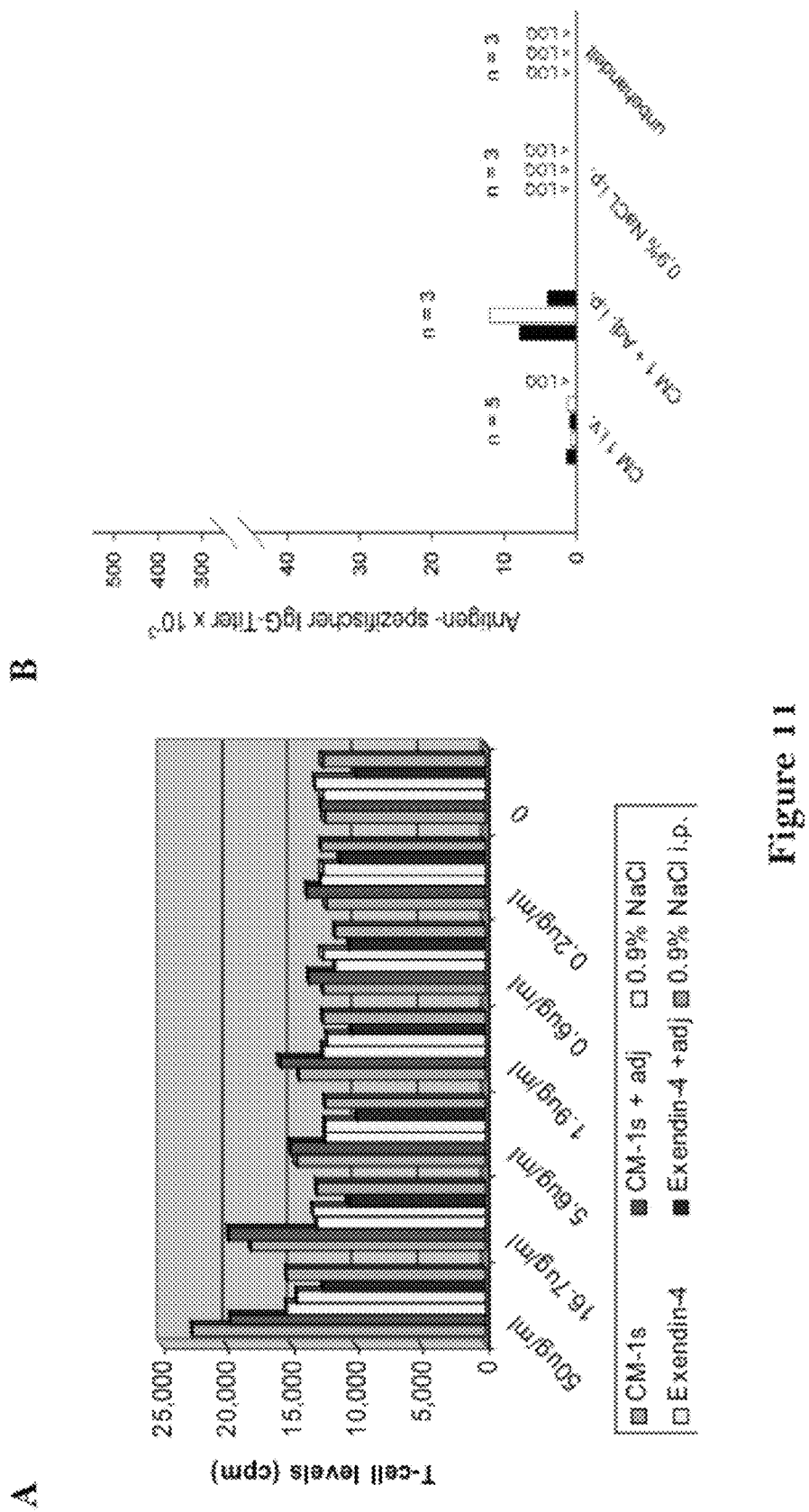
FIG. 11 illustrates studies for evaluation of potential immunogenic effects of CM1syn. On the left hand side (FIG. 11A)) results of a T-cell recall response assay are shown. Spleens of the treated and control mice were explanted, T-cells isolated and stimulated with increasing amounts of antigene. Proliferative recall response is measured. On the right hand side (FIG. 11B), the antigen specific IgG antibody titer in the immune sera of the animals was determined.

$CM1_{syn}$ induced no toxicity and only a minimal T-cell antibody response and antibody titer as shown in the following figure. An immunologic effect of by-products (purity of the peptide only 95%) cannot be excluded. FIG. 11 shows studies for evaluation of potential immunogenic effects of CM1syn. On the left hand side (FIG. 11A), results of a T-cell recall response assay are shown. Spleens of the treated and control mice were explanted, T-cells isolated and stimulated with increasing amounts of antigene. Proliferative recall response is measured. On the right hand side (FIG. 11B), the antigen specific IgG antibody titer in the immune sera of the animals was determined.

Example 11

Dose-Efficacy Study in Diabetic Mice

After a two-hour fastening period diabetic C57BL/KsJ@Rj-db (db/db) mice were treated with five different concentrations of GLP-1, CM1, CM3, CM3-ANA01 and exendin-4. A sixth group was treated with saline only. 7 animals were treated per group. Blood glucose was determined from tail bleeds directly before, 1 hour and 4 hours after injection.

Figure 12:
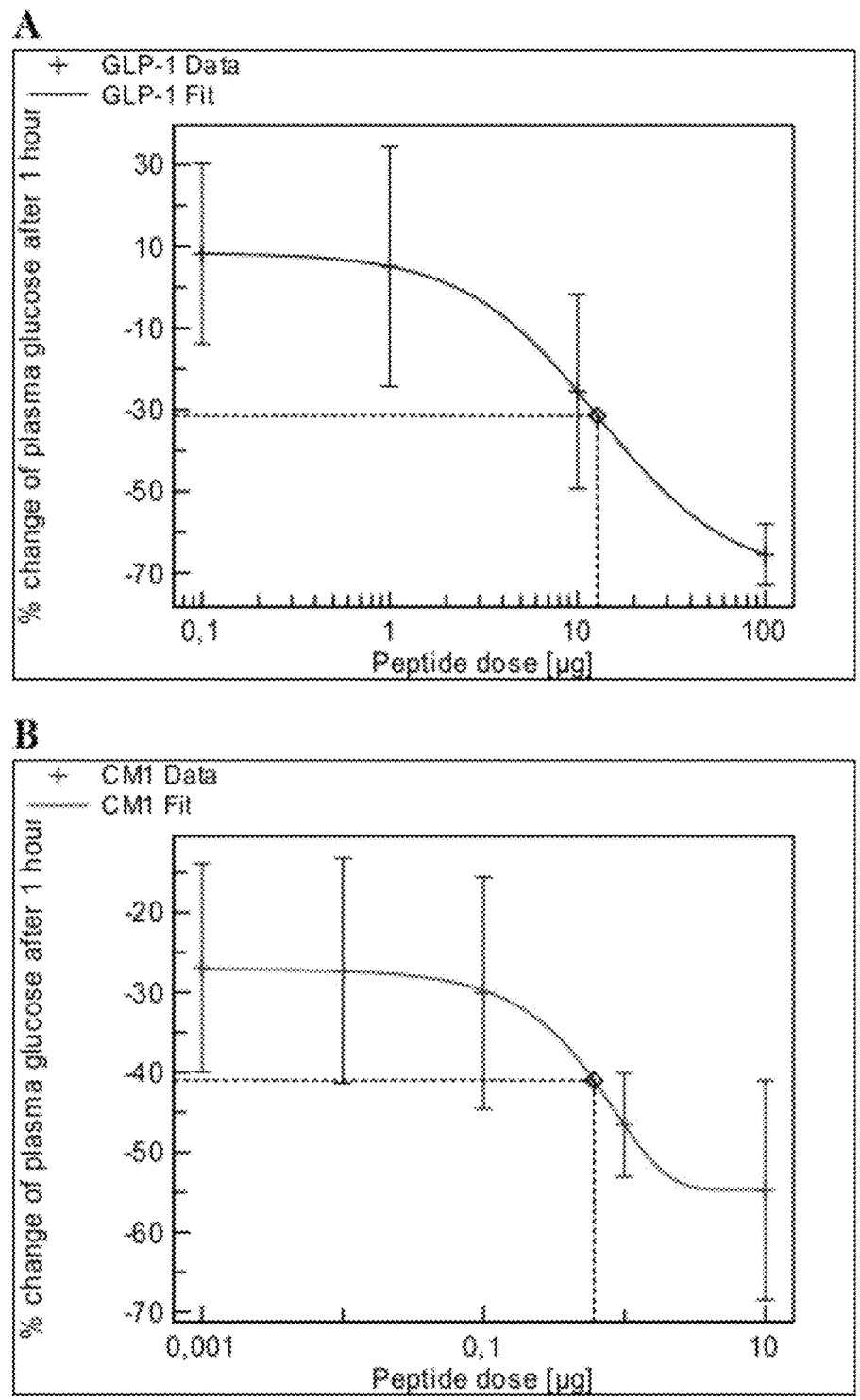
FIG. 12 illustrates results of two-hour fasting period diabetic C57BL/KsJ@Rj-db (db/db) mice were treated with five different concentrations of GLP-1, CM1, CM3, CM3-ANA01 and exendin-4. A sixth group was treated with saline only. 7 animals were treated per group. Blood glucose was determined from tail bleeds directly before, 1 hour and 4 hours after injection.
Figure 12:
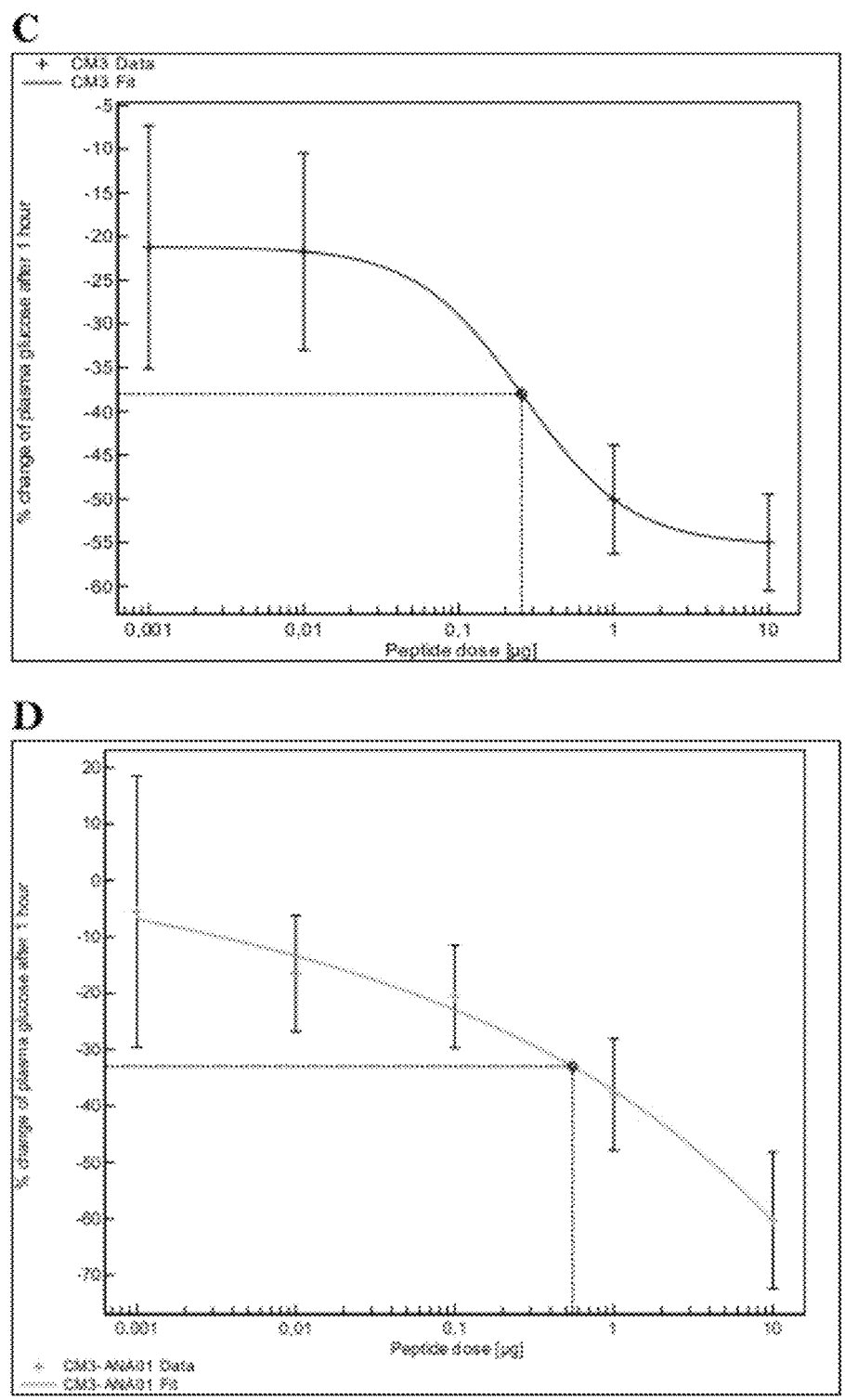

The results are shown in dose-response curves according to FIG. 12 (FIG. 12A (GLP-1), FIG. 12B (CM1), FIG. 12C (CM3) and FIG. 12D (CM3-ANA01)). For every test substance a graph was prepared with the percentage difference of the blood glucose in relation to the start value for the different concentrations. The $ED_{50}$ value for the different test substances was determined by preparing a dose response curve with the values of the 1 h measurements as a percentage reduction in comparison to the basal value. To evaluate the $ED_{50}$ value for GLP-1, CM3-ANA01, $CM3_{rec}$ and Exendin-4 the Morgan-Mercer-Flodin (MMF) model was used, for CM1 the Richards model was used. Both models are sigmoidal fit models suitable for dose response evaluation. For every peptide the plasma glucose $ED_{50}$ values (single s.c. dose in μg/mouse) have been determined from the percentage decrease of blood glucose. They are summarized in table 1.

TABLE 1

| Peptide | $ED_{50}$ [μg/mouse] |
|---|---|
| $GLP-1_{(7-37)}$ | 12.76 |
| CM1 | 0.61 |
| CM3 | 0.25 |
| CM3-ANA01 | 0.55 |
| exendin-4 | 0.03 |

Deduced from the $ED_{50}$ values, the GLP-1 analogs CM1, CM3 and CM3-ANA01 reveal a more than 20 fold better in vivo bioactivity, which is most likely a result of the enhanced plasma stability.

All peptides tested lead to a significant decrease of blood glucose levels in hyperglycaemic db/db mice at least for the highest concentrations. The fall in plasma glucose after a single s.c. injection of 1.1-3.0 nmol peptide (versus control) is summarized in table 2. Table 2 exhibits the glucose lowering effects of the test substances (versus control). The fall in plasma glucose and the corresponding significance levels are given for the time period 1 hour (@1 h) and 4 hours (@4 h) after peptide injection. Differences have been observed in the long-term efficacy of the peptides. Only exendin-4 and CM3 revealed a significant decrease of the blood glucose levels after 4 hours.

TABLE 2

| Peptide | concentration | fall in plasma glucose | p value (independent t-test) |
|---|---|---|---|
| $GLP-1_{(7-37)}$ | 3.0 nmol | 15% ± 24% @1 h | not significant |
|  | 3.0 nmol | 0% @4 h | not significant |
| CM1 | 1.1 nmol | 50% ± 14% @1 h | p < 0.0001 |
|  | 1.1 nmol | 0% @4 h | not significant |
| CM3 | 2.0 nmol | 46% ± 6% @1 h | p < 0.01 |
|  | 2.0 nmol | 21% ± 10% @4 h | p < 0.05 |

TABLE 2-continued

| Peptide | concentration | fall in plasma glucose | p value (independent t-test) |
|---|---|---|---|
| CM3-ANA01 | 2.0 nmol | 62% ± 12% @1 h | p < 0.001 |
|  | 2.0 nmol | 18% ± 11% @4 h | not significant |
| exendin-4 | 2.4 nmol | 32% ± 14% @1 h | p < 0.01 |
|  | 2.4 nmol | 29% ± 9% @4 h | p < 0.01 |

Example 12

Long-Term Treatment of db/db Mice

Four groups with n=12 C57BL/KsJ@Rj-db (db/db) mice have been investigated:
Group A treatment with vehicle (0.9% saline) once daily
Group B treatment with 24 nmol/kg test substance 1: CM1rec once daily
Group C treatment with 24 nmol/kg test substance 2: CM3-ANA01 once daily
Group D treatment with 24 nmol/kg reference substance exendin-4 (known in the art and approved (however, exendin-4 is not an GLP-1 analog)) once daily Peptides or vehicle will be given once daily (group A-D) between 2:00-3:00 p.m. subcutaneously in the skin fold of the back. The regimen was continued for 18 weeks. From week 12 to 18 treatment was done twice a day in 6 of 12 animals per group.

Various parameters of the mice were investigated, i.e. health status (1), body weight (2), food consumption (3), blood glucose (4), glucose tolerance test (5), insulin data (6), glycosylated hemoglobin (7), pathology (8), and restimulation of T cells (9).

Health status (1) was good in all groups, no side effects of the treatment have been seen.

Figure 13:
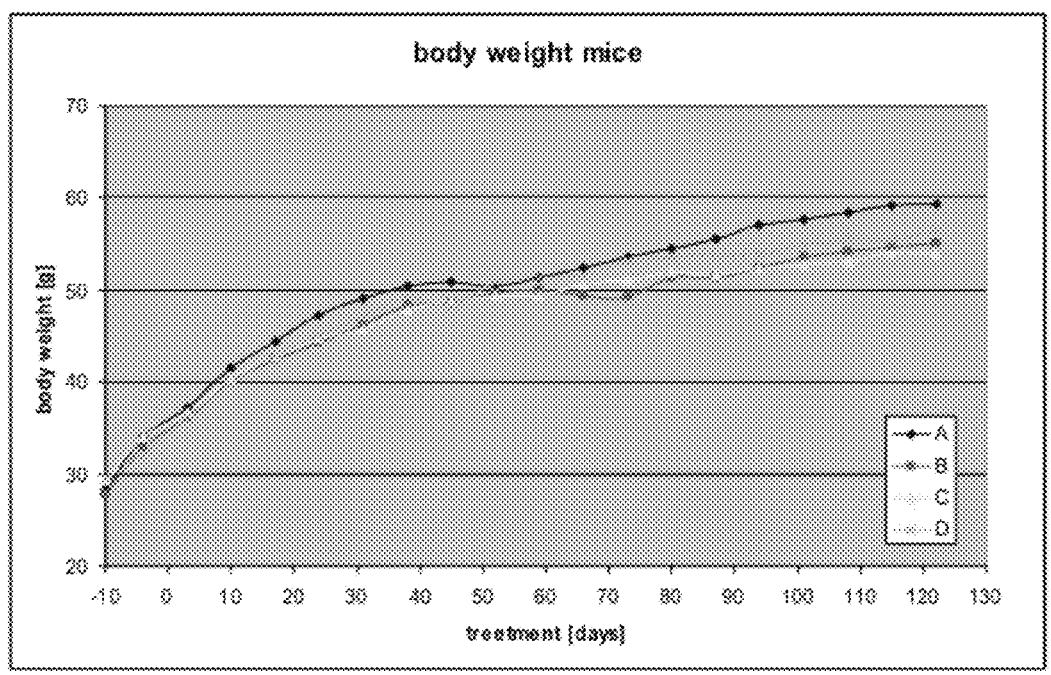
FIG. 13 illustrates relative body weight increase is significantly lower in the CM3-ANA01 group.
Figure 13:
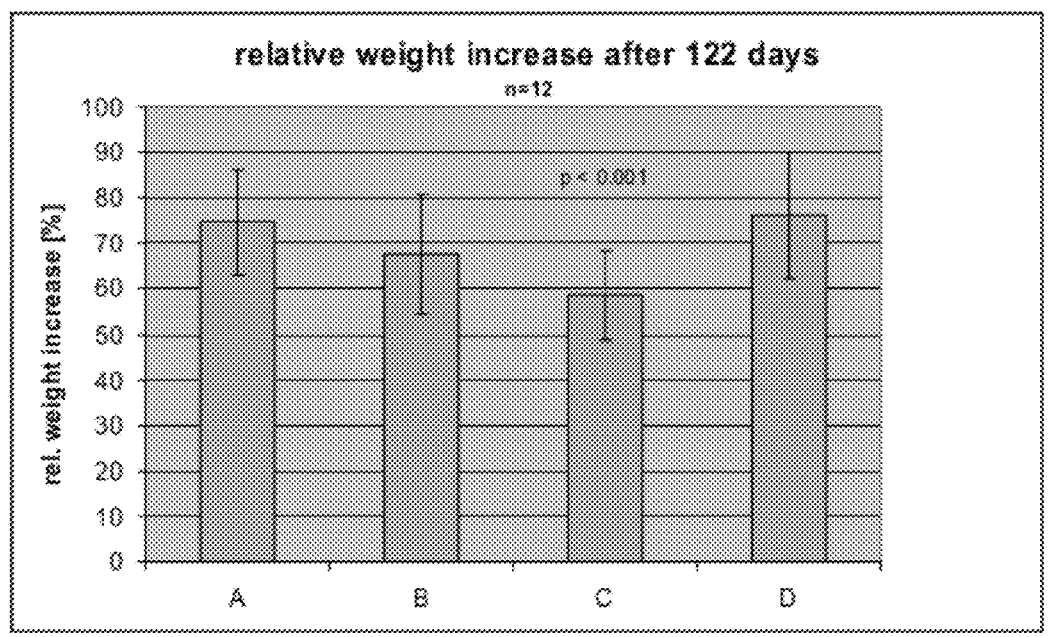

Body weight (2) was lower in all treated groups after 18 weeks of treatment (FIG. 13). Relative body weight increase is significantly lower in the CM3-ANA01 group. FIG. 13A shows the effect of a treatment with saline (A), CM1 (B), CM3-ANA01 (C) or exendin (D) on the body weight of db/db mice. The mean values of 12 animals per group are plotted. FIG. 13B shows the effect of a treatment with saline (A), CM1 (B), CM3-ANA01 (C) or exendin (D) on the body weight of db/db mice. The relative body weight increase of 12 animals per group after a treatment of 122 days is plotted. Only the treatment with test substance CM3-ANA01 (group B) revealed a significantly lower weight increase (p<0.001).

Figure 14:
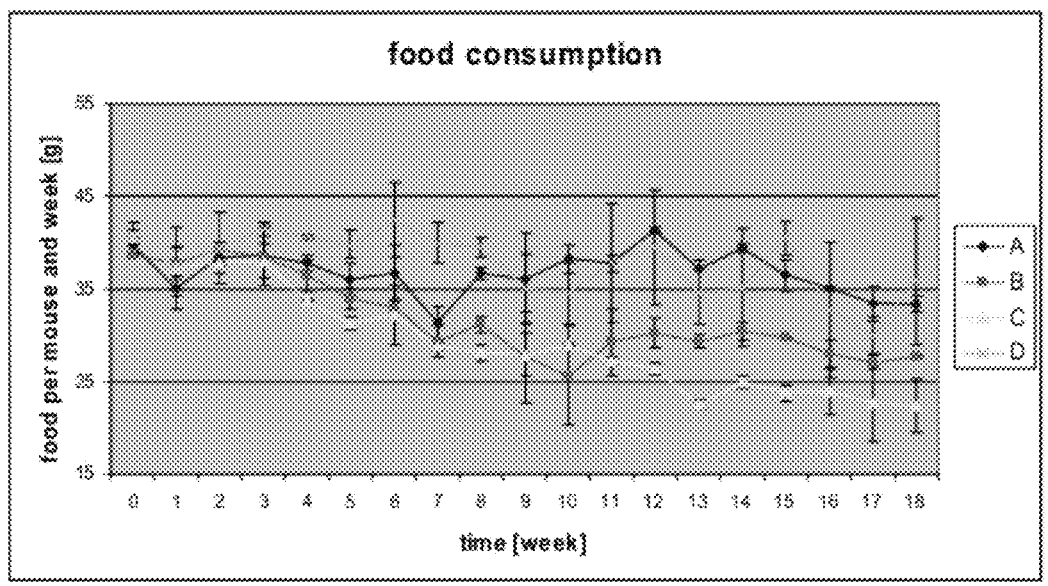
FIG. 14 illustrates the effect of a treatment with saline (A), CM1 (B), CM3-ANA01 (C) or exendin (D) on the weekly food consumption of db/db mice during a 122 day treatment period.

Food consumption (3) was significantly lower in the CM1 and CM3-ANA01 group compared to the control. FIG. 14 shows the effect of a treatment with saline (A), CM1 (B), CM3-ANA01 (C) or exendin (D) on the weekly food consumption of db/db mice during a 122 day treatment period. The relative food consumption per mouse is significantly decreased in group B and C (p<0.001).

Figure 15:
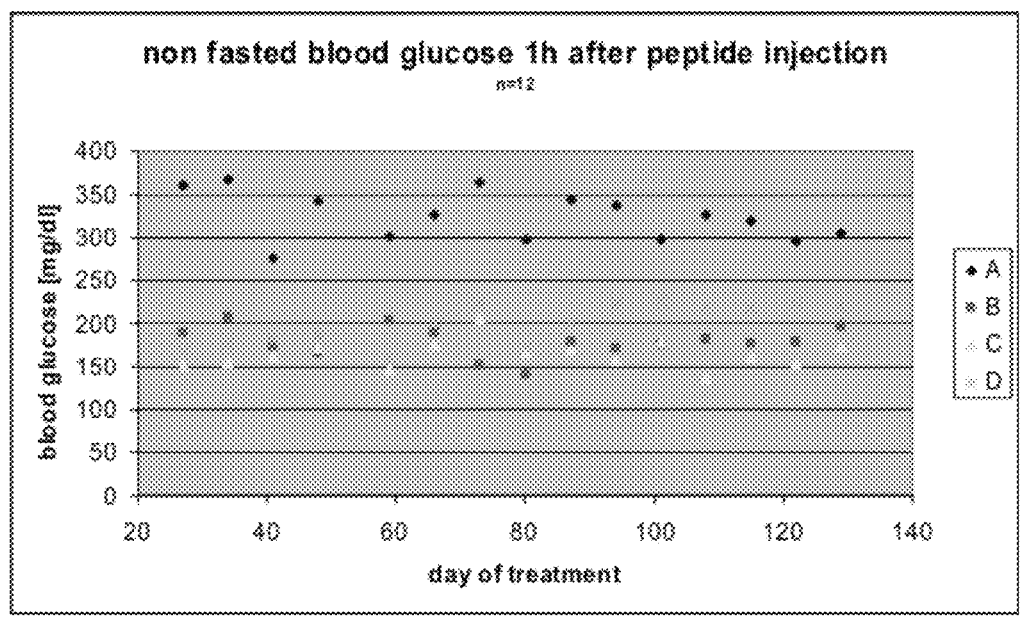
FIG. 15 illustrates the non-fasted blood glucose level (1 hour after peptide injection). 15A, i.e. the effect of a treatment with saline (A), CMI (B), CM3-ANA01 (C) or exendin (D) on the non-fasted blood glucose levels. Blood glucose was measured from a tail bleed 1 hour after s.c. injection of saline (A) or the peptides CMI (B), CM3-ANA01 (C) or exendin (D) in a concentration of 24 nmol/kg. Compared to control non fasted blood glucose level 1 h after s.c, peptide injection is reduced to 55% in group B, 51% in group C and 60% in group D (FIG. 15B).
Figure 15:
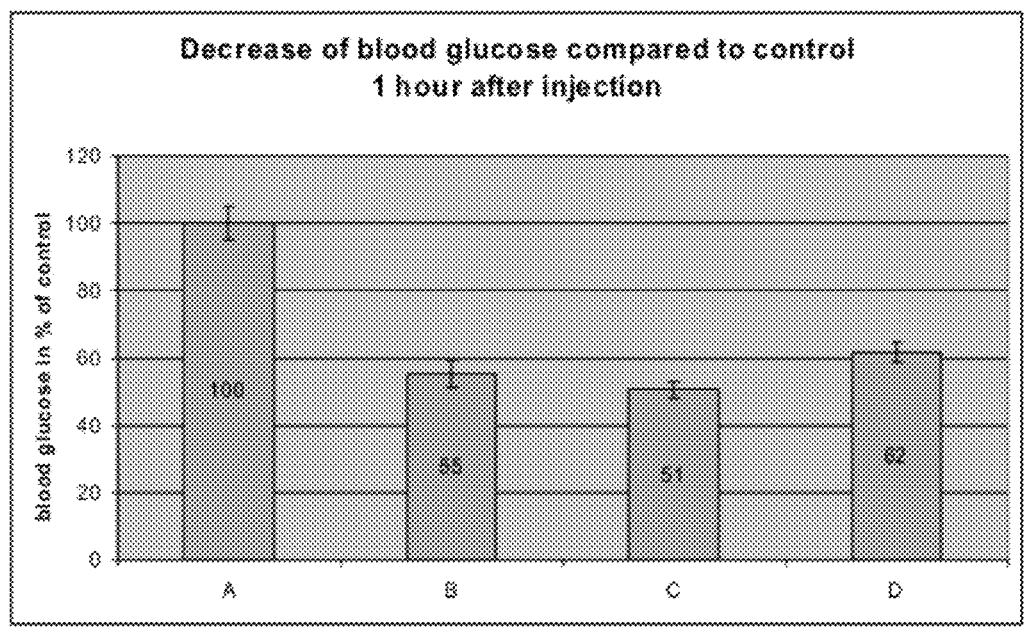
Figure 15:
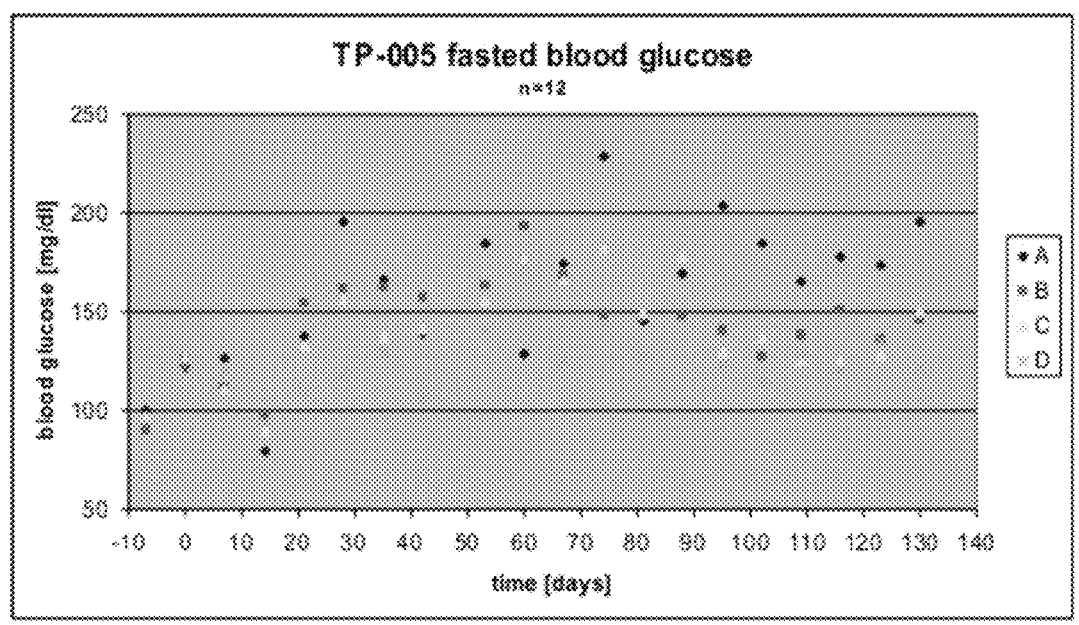

Blood glucose (4) levels were determined in a variety of situations. Non-fasted blood glucose level (1 hour after peptide injection) is shown in FIG. 15A, i.e. the effect of a treatment with saline (A), CM1 (B), CM3-ANA01 (C) or exendin (D) on the non-fasted blood glucose levels. Blood glucose was measured from a tail bleed 1 hour after s.c. injection of saline (A) or the peptides CM1 (B), CM3-ANA01 (C) or exendin (D) in a concentration of 24 nmol/kg. Compared to control non fasted blood glucose level 1 h after s.c. peptide injection is reduced to 55% in group B, 51% in group C and 60% in group D (FIG. 15B). The blood glucose decrease in the treated groups treated groups is highly significant (p<0.0001).

Fasted blood glucose level (18 hours after peptide injection) are shown in FIG. 15C, i.e. the effect of a treatment with saline (A), CM1 (B), CM3-ANA01 (C) or exendin (D) on the fasted blood glucose levels. Blood glucose was measured from a tail bleed after a 12-hour overnight fast 18 hours after s.c. injection of the test substances. Fasted blood glucose level 18 h after peptide injection is reduced in the CM1 and CM3-ANA01 group.

Figure 16:
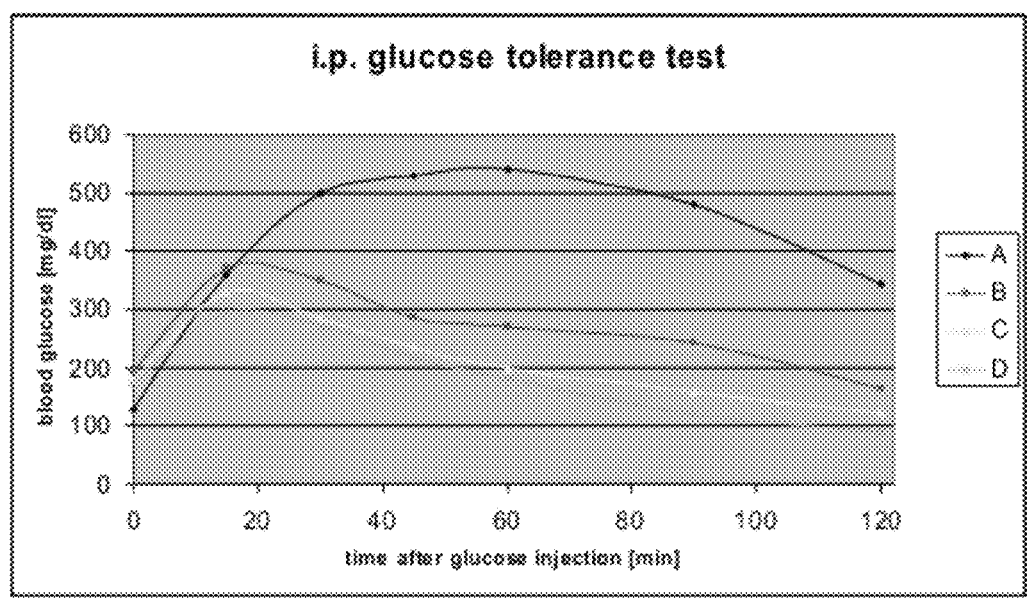
FIG. 16 illustrates blood glucose determined 15, 30, 45, 60; 90 and 120 minutes after glucose injection. A significant normalization of glucose tolerance was shown in all treated groups (FIG. 16A).
Figure 16:
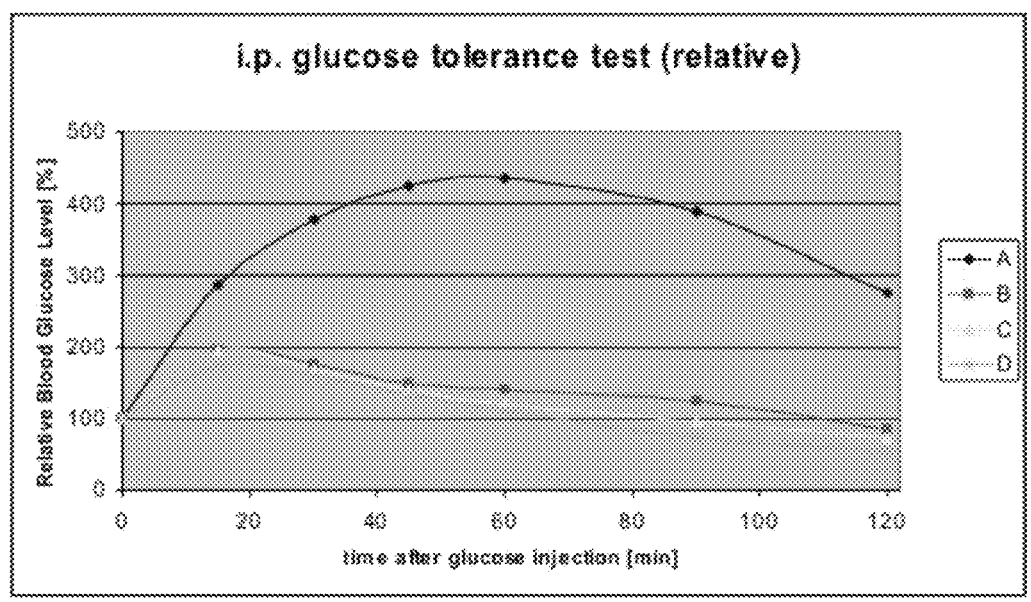

An i.p. glucose tolerance test (5) (IPGTT) was conducted after 8 weeks of treatment on mice of the groups A-D. The basal blood glucose value (0 min) of 12 hour fasted animals has been determined by tail bleed followed by an s.c. injection of the test substance and an i.p. injection of 20% glucose solution (1 g glucose per kg). Blood glucose has been further on determined 15, 30, 45, 60, 90 and 120 minutes after glucose injection. A significant normalization of glucose tolerance was shown in all treated groups (FIG. 16A). In FIG. 16A absolute blood glucose levels during an i.p. glucose tolerance test (IPGTT) after 8 weeks of treatment with saline (A), CM1 (B), CM3-ANA01 (C) or exendin (D) is shown (mean values of each group (n=12)).

Another presentation of the data presented by FIG. 16A of the blood glucose tolerance test is given in FIG. 16B. Relative blood glucose levels during an i.p. glucose tolerance test (IPGTT) after 8 weeks of treatment with saline (A), CM1 (B), CM3-ANA01 (C) or exendin (D) normalized on the starting blood glucose level (100%).

Figure 17:
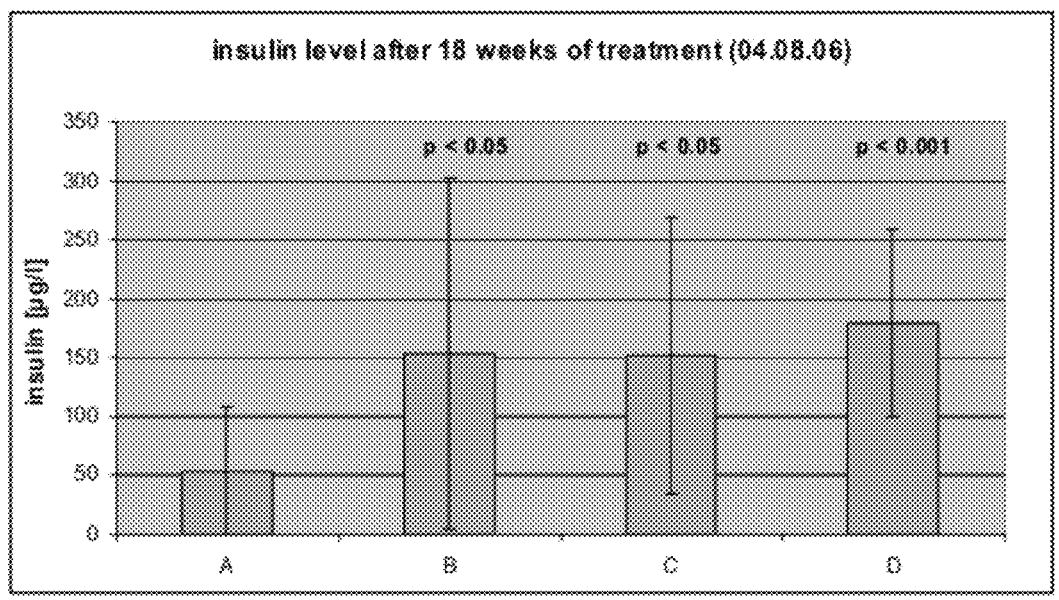
FIG. 17 illustrates the data for serum insulin levels in mice after 18 week treatment with 0.9% saline (Group A), CM1 peptide (group B), CM3-ANA01 peptide (group C) or exendin-4 (group D).

Insulin levels (6) were determined from mice after a 12 hour overnight fastening period. After 18 weeks of treatment, all mice of the treated groups produce significantly more insulin than the non-treated control. FIG. 17 presents the data for serum insulin levels in mice after 18 week treatment with 0.9% saline (Group A), CM1 peptide (group B), CM3-ANA01 peptide (group C) or exendin-4 (group D). Directly after sampling blood samples have been treated with a protease inhibitor cocktail to avoid insulin degradation. The serum was analysed for insulin with the Insulin Mouse Ultrasensitive ELISA (Cat.# EIA-3440, DRG). Significance has been determine with Student's t-test.

Glycosylated hemoglobin (7) is formed by excess plasma glucose binding to hemoglobin in red blood cells (RBC). Since RBCs have a 120-day lifespan, measurements of the glycolylated hemoglobin gives a longer-term indication of glucose control and is seen as a better indicator than plasma glucose levels. Whole blood was collected from the retro-orbital sinus and analyzed with the Enzymatic HbA1c Test Kit (#DZ121A, Diazyme) to determine the glycosylated hemoglobin levels. Using glycosylated hemoglobin as a parameter, a significant reduction in the increase was seen in all treated groups.

Figure 18:
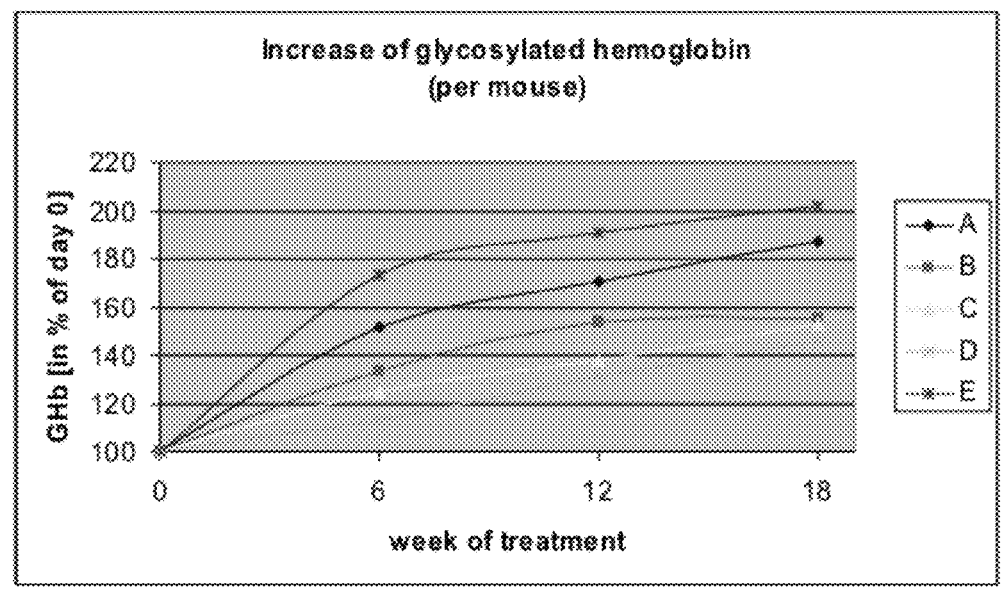
FIG. 18A illustrates the relative increase of glycosylated hemoglobin (GHb) in whole blood samples after 6, 12 and 18 weeks of treatment with saline (A), CM1 (B), CM3-ANA01 (C) or exendin (D).
FIG. 18B shows the relative increase of glycosylated hemoglobin({GHb) in whole blood samples after 18 weeks of treatment with saline (A), CM1 (B), CM3-ANA01 (C) or exendin (D).
Figure 18:
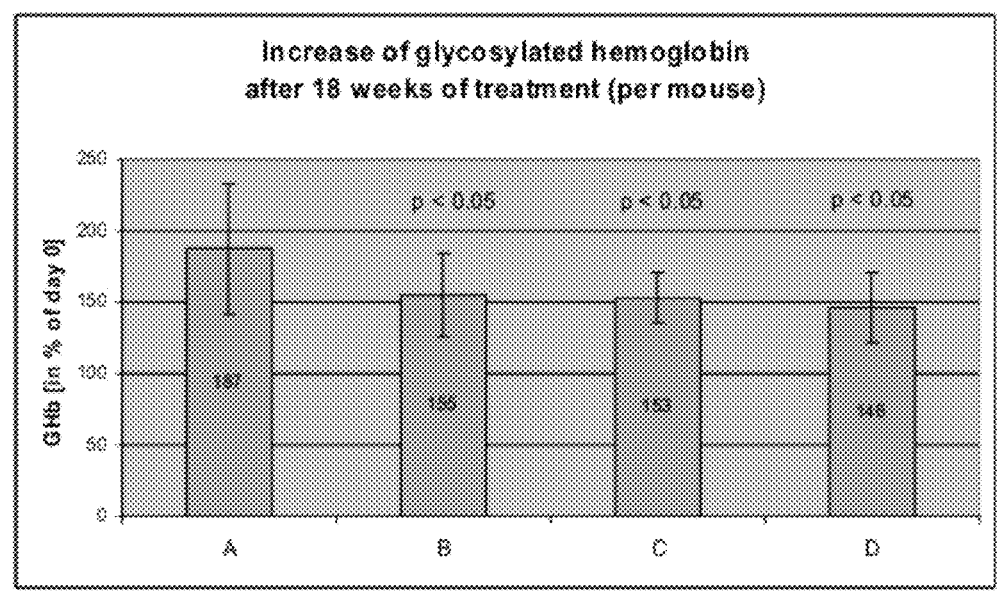

FIG. 18A shows the relative increase of glycosylated hemoglobin (GHb) in whole blood samples after 6, 12 and 18 weeks of treatment with saline (A), CM1 (B), CM3-ANA01 (C) or exendin (D). FIG. 18B shows the relative increase of glycosylated hemoglobin (GHb) in whole blood samples after 18 weeks of treatment with saline (A), CM1 (B), CM3-ANA01 (C) or exendin (D). The mean value of all animals per group (n=12) is given. The increase of the glycosylated hemoglobin levels of all treated groups are significantly lower than the control.

Figure 19:
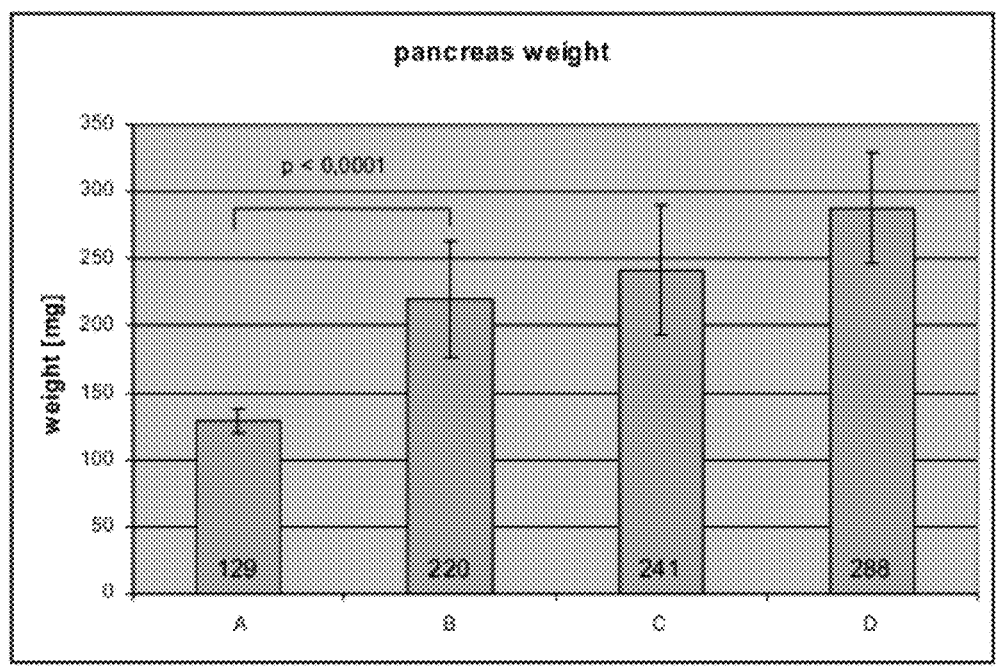
FIG. 19 illustrates the pancreas weight determined at day of scarification of the animals after 18 weeks of treatment with 0.9% saline (Group A, n=11), CM1 peptide (group B, n=12)) CM3-ANA01 peptide (group C, n=12) or exendin-4 (group D, n=12)

Pathology (8) of the mice treated was conducted. Necropsy revealed no differences in the organs of the treated groups compared to the non-treated group A, except the pancreas volume. Pancreas weight was determined and revealed to be highly significant higher in all treated groups. FIG. 19 presents the pancreas weight determined at day of scarification of the animals after 18 weeks of treatment with 0.9% saline (Group A, n=11), CM1 peptide (group B, n=12), CM3-ANA01 peptide (group C, n=12) or exendin-4 (group D, n=12).

Figure 20:
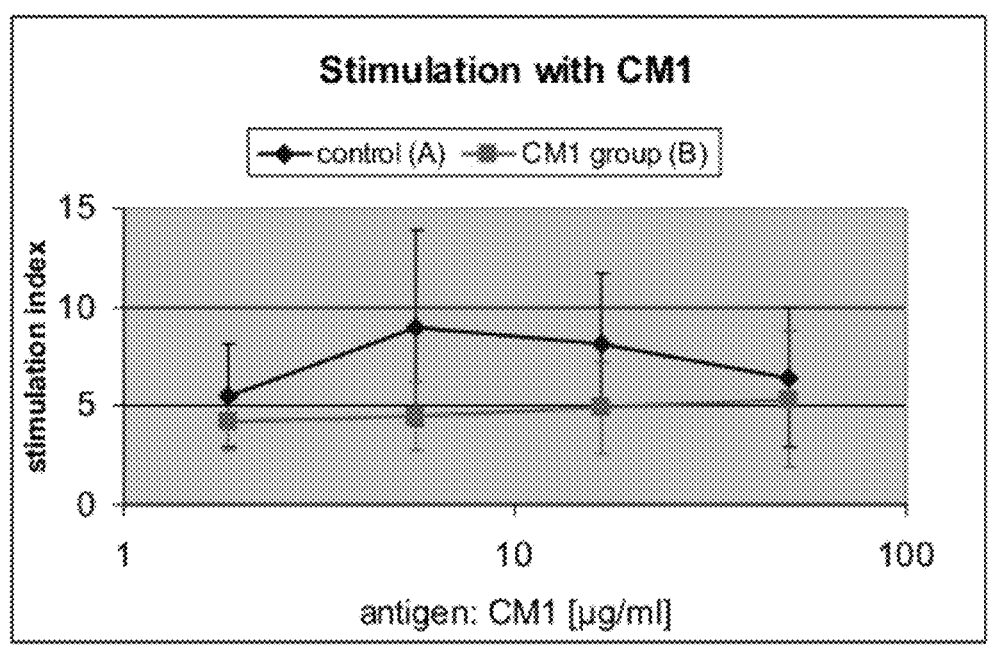
FIG. 20 illustrates the in vitro recall response of spleen cells to different concentrations of the test substances CM1 (FIG. 20A) and CM3-ANA01 (FIG. 20B) and the reference substance exendin-4 (FIG. 20C).
Figure 20:
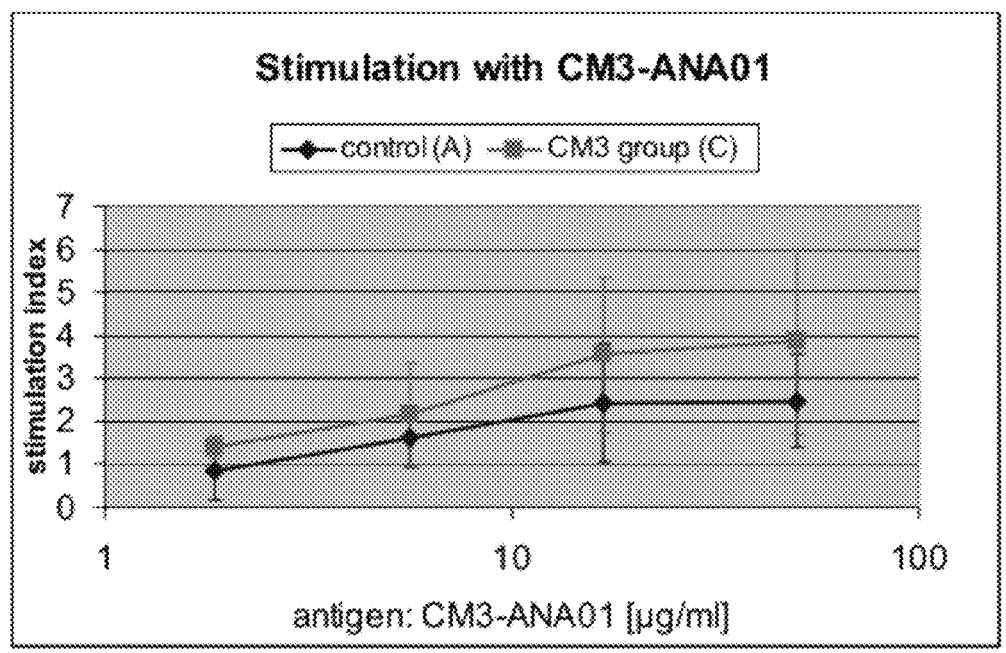
Figure 20:
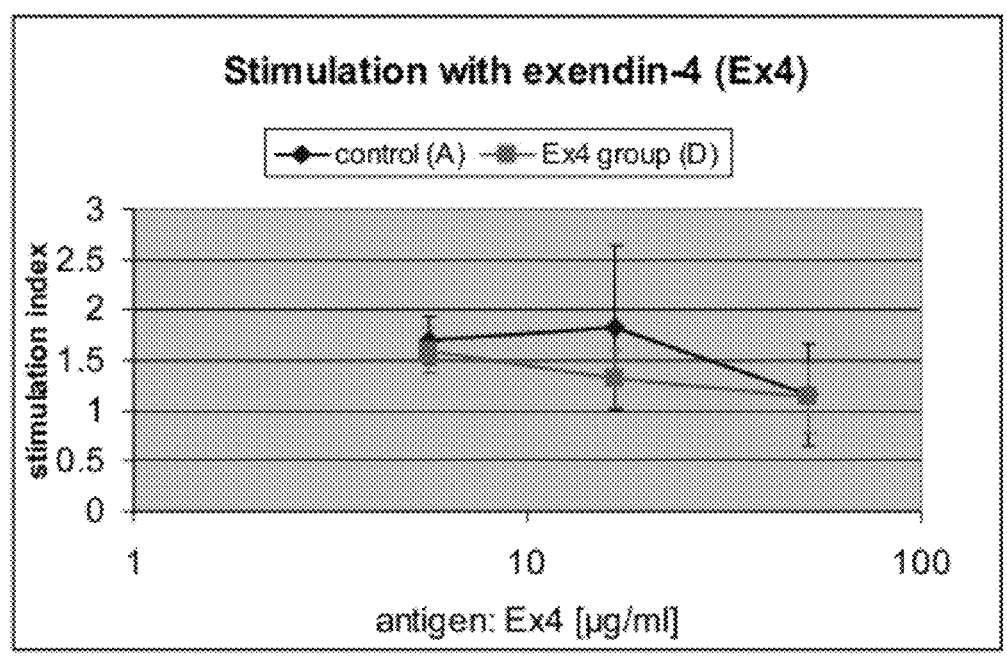

To evaluate potential immunological effects of the tested substances, type IV immunogenicity (9) was examined by T cell restimulation. Therefore, the spleen of 8 animals per group was explanted, T-cells isolated and restimulated with different concentrations of the corresponding test substance. Compared to non-treated controls no significant increase in peptide restimulated T-cell proliferation was found. FIG. 20 shows the in vitro recall response of spleen cells to different concentrations of the test substances CM1 (FIG. 20A) and CM3-ANA01 (FIG. 20B) and the reference substance exendin-4 (FIG. 20C). Using a non-radioactive cell proliferation assay (Cell Proliferation ELISA, BrdU, chemiluminescent) the in vitro recall response of spleen cells of mice of group A to D to 3-fold dilutions of the test substances CM1 and CM3-ANA01 and the reference substance exendin-4, starting at 50 µg/ml, were measured in triplicates of individual mice. The stimulation index (SI) was calculated as the quotient of the response in the presence of the respective peptide and the response in the absence of peptides. Mean values±standard deviations of the respective treated group and control group are shown (group A: n=3, group B: n=6, group C: n=7, group D: n=6). For the calculation of the mean values only mice, with a SI of more than 6.5 in the positive control cultures with 5 µg/ml Con A were analysed.

The long-term study in diabetic mice further supports the efficacy of the inventive C-terminally elongated peptides. In all parameters tested (body weight, food consumption, blood glucose levels, glycosylated hemoglobin, glucose tolerance, insulin secretion, pancreas weight) the C-terminally elongated peptides revealed a significant therapeutic effect. Taking in account the homology of the C-terminally elongated CellMed peptides with the endogenously occurring sequence it was shown that these inventive peptides are advantageous in terms of immunogenicity compared to non-mammalian exendin-4. Data from an immunogenicity study in mice support the absence of any clinically relevant immunogenicity of the CM1 peptide.

The invention claimed is:

1. A fusion peptide comprising
a component (I) N-terminally having a sequence according to formula I:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-X(I) (SEQ ID NO: 43), wherein X is NH$_2$ or Gly-OH, or a sequence having 95% sequence identity with SEQ ID NO: 43;

a component (II) C-terminally having a peptide sequence containing SEQ ID NO: 22 or sequence having 90% sequence identity with SEQ ID NO: 22 (RRDFPE-EVAI); and a component (III) C-terminally having a sequence according to formula I (SEQ ID NO: 43) or a sequence having 95% sequence identity with SEQ ID NO: 43;

and its pharmaceutically active salts.

2. The fusion peptide according to claim 1, wherein the component (II) is a peptide sequence containing a sequence selected from a group consisting of SEQ ID NO: 23 (RRDFPEEVAIVEEL) and SEQ ID NO: 24 (RRDFPEEVAIAEEL), or a sequence having at least 90% sequence identity with any of SEQ ID NO: 23 or 24.

3. The fusion peptide according to claim 1, wherein the component (II) is a peptide sequence containing a sequence selected from the group consisting of SEQ ID NO: 2 (RRDFPEEVAIVEELG), SEQ ID NO: 3 (RRDFPEEVAIAEELG), or a sequence having at least 90% sequence identity with SEQ ID NO: 2 or 3.

4. The fusion peptide according to claim 1, wherein the fusion peptide contains a sequence selected from the group consisting of:
SEQ ID NO: 8 (HAEGTFTSDVSSYLEGQAAKEFIAWLVKGRGRRDFPEEVAIAEELG),
SEQ ID NO: 12 (HAEGTFTSDVSSYLEGQAAKEFIAWLVKGRGRRDFPEEVAIVEELG),
SEQ ID NO: 32 (HAEGTFTSDVSSYLEGQAAKEFIAWLVKGRGRRDFAEEVAIAEELG),
SEQ ID NO: 36 (HAEGTFTSDVSSYLEGQAAKEFIAWLVKGRGRRDFPEEVA),
SEQ ID NO: 37 (HAEGTFTSDVSSYLEGQAAKEFIAWLVKGRGRRDFPEEVAIAEELGR RHAC),
SEQ ID NO: 39 (HAEGTFTSDVSSYLEGQAAKEFIAWLVKGRGRRDFAEEVAIVEELG), and
SEQ ID NO: 42 (HAEGTFTSDVSSYLEGQAAKEFIAWLVKGRGRRDFPEEVAIVEELGR RHAC), or a sequence having at least 95% sequence identity with SEQ ID NO: 8 or 12.

5. The fusion peptide according to claim 1, wherein the fusion peptide contains a peptide sequence selected from a group consisting of: SEQ ID NO: 6 or SEQ ID NO: 10 or a sequence having at least 95% sequence identity with SEQ ID NO: 6 or 10.

6. The fusion peptide according to claim 1, wherein the fusion peptide consists of SEQ ID NO: 6 or SEQ ID NO: 10.

7. The fusion peptide according to claim 1, wherein the N-terminal His residue of formula I of the fusion peptide is chemically modified at its $NH_2$ terminus and/or at its histidyl side chain by a hydrophobic moiety.

8. The fusion peptide according to claim 1, wherein the fusion peptide further comprises a carrier protein, comprising transferrin or albumin, as component (IV).

9. The fusion peptide according to claim 1, wherein the fusion peptide further comprises a leader or a signal peptide sequence upstream of component (I).

10. A nucleic acid encoding a fusion peptide according to claim 1.

11. A vector comprising a nucleic acid according to claim 9.

12. A pharmaceutical composition comprising the fusion peptide according to claim 1, or according to claim 6.

* * * * *